(12) United States Patent
Shouldice et al.

(10) Patent No.: US 12,303,287 B2
(45) Date of Patent: May 20, 2025

(54) APPARATUS, SYSTEM, AND METHOD FOR HEALTH AND MEDICAL SENSING

(71) Applicant: RESMED SENSOR TECHNOLOGIES LIMITED, Sandyford (IE)

(72) Inventors: Redmond Shouldice, Clonskeagh (IE); Stephen Mcmahon, Dundrum (IE); Michael Wren, Clonskeagh (IE)

(73) Assignee: ResMed Sensor Technologies Limited (IE)

( * ) Notice: Subject to any disclaimer, the term of this patent is extended or adjusted under 35 U.S.C. 154(b) by 320 days.

(21) Appl. No.: 16/767,849

(22) PCT Filed: Dec. 21, 2018

(86) PCT No.: PCT/EP2018/086762
§ 371 (c)(1),
(2) Date: May 28, 2020

(87) PCT Pub. No.: WO2019/122412
PCT Pub. Date: Jun. 27, 2019

(65) Prior Publication Data
US 2020/0367810 A1    Nov. 26, 2020

Related U.S. Application Data

(60) Provisional application No. 62/610,033, filed on Dec. 22, 2017.

(51) Int. Cl.
*A61B 5/00* (2006.01)
*A61B 5/02* (2006.01)
(Continued)

(52) U.S. Cl.
CPC .............. *A61B 5/4809* (2013.01); *A61B 5/02* (2013.01); *A61B 5/0205* (2013.01);
(Continued)

(58) Field of Classification Search
None
See application file for complete search history.

(56) References Cited

U.S. PATENT DOCUMENTS 6,661,345 B1    12/2003   Bevan et al.
RE42,471 E       6/2011   Torch
(Continued)

FOREIGN PATENT DOCUMENTS

CN    101917903 A    12/2010
CN    204306833 U     5/2015
(Continued)

OTHER PUBLICATIONS

Partial International Search Report issued on Mar. 25, 2019.
(Continued)

*Primary Examiner* — Aurelie H Tu
(74) *Attorney, Agent, or Firm* — Botos Churchill IP Law LLP

(57) ABSTRACT

Methods and devices provide physiological movement detection, such as breathing, cardiac and/or gross body motion, with active sound generation using electronic processing device(s). The processor may control producing, via a speaker coupled to the processor, a sound signal in a user's vicinity. The processor may control sensing, via a microphone coupled to the processor, a reflected sound signal. This reflected sound signal is a reflection of the sound signal from the vicinity or user. The processor may process the reflected sound, such as by a demodulation technique. The sound signal may be produced as a dual tone frequency modulation continuous wave signal. Evaluation of detected movement information may determine sleep states or scoring, fatigue indications, subject recognition, chronic disease monitoring/prediction, and other output parameters.

51 Claims, 18 Drawing Sheets

(51) Int. Cl.

| | |
|---|---|
| *A61B 5/0205* | (2006.01) |
| *A61B 5/024* | (2006.01) |
| *A61B 5/05* | (2021.01) |
| *A61B 5/11* | (2006.01) |
| *A61B 5/113* | (2006.01) |
| *A61B 8/00* | (2006.01) |
| *A61B 8/08* | (2006.01) |
| *G06F 3/16* | (2006.01) |
| *G10K 15/04* | (2006.01) |
| *G10L 25/66* | (2013.01) |
| *G16H 20/30* | (2018.01) |
| *G16H 40/40* | (2018.01) |
| *G16H 40/67* | (2018.01) |
| *G16H 50/20* | (2018.01) |
| *G16H 50/30* | (2018.01) |
| *G16H 50/50* | (2018.01) |
| *H04R 1/02* | (2006.01) |
| *H04R 1/08* | (2006.01) |
| *H04R 3/04* | (2006.01) |

(52) U.S. Cl.
CPC ............ *A61B 5/02405* (2013.01); *A61B 5/05* (2013.01); *A61B 5/1126* (2013.01); *A61B 5/113* (2013.01); *A61B 5/4812* (2013.01); *A61B 5/4818* (2013.01); *A61B 5/4833* (2013.01); *A61B 5/681* (2013.01); *A61B 5/6887* (2013.01); *A61B 5/7225* (2013.01); *A61B 5/7228* (2013.01); *A61B 5/7257* (2013.01); *A61B 5/7405* (2013.01); *A61B 8/08* (2013.01); *A61B 8/5207* (2013.01); *A61B 8/5223* (2013.01); *G06F 3/165* (2013.01); *G10K 15/04* (2013.01); *G10L 25/66* (2013.01); *G16H 20/30* (2018.01); *G16H 40/40* (2018.01); *G16H 40/67* (2018.01); *G16H 50/20* (2018.01); *G16H 50/30* (2018.01); *G16H 50/50* (2018.01); *H04R 1/028* (2013.01); *H04R 1/08* (2013.01); *H04R 3/04* (2013.01); *H04R 2499/11* (2013.01)

(56) References Cited

U.S. PATENT DOCUMENTS

| | | | |
|---|---|---|---|
| 8,562,526 B2 | 10/2013 | Heneghan et al. | |
| 8,841,994 B2 | 9/2014 | Li | |
| 8,874,301 B1 | 10/2014 | Rao et al. | |
| 9,430,938 B2 | 8/2016 | Proud | |
| 9,489,817 B2 | 11/2016 | Gui | |
| 9,500,489 B1 | 11/2016 | Ng | |
| 9,862,271 B2 | 1/2018 | Brankovic et al. | |
| 9,883,821 B2 | 2/2018 | Muehlsteff | |
| 9,993,166 B2 | 6/2018 | Johnson et al. | |
| 10,004,451 B1 | 6/2018 | Proud | |
| 10,004,873 B1 | 6/2018 | Hur et al. | |
| 10,009,581 B2 | 6/2018 | Proud | |
| 10,159,421 B2 | 12/2018 | Heneghan | |
| 2004/0039254 A1 | 2/2004 | Stivoric et al. | |
| 2004/0203616 A1 | 10/2004 | Minear et al. | |
| 2005/0073424 A1 | 4/2005 | Ruoss et al. | |
| 2008/0077015 A1* | 3/2008 | Boric-Lubecke ..... G01S 13/888 |
| | | | 600/453 |
| 2008/0183388 A1 | 7/2008 | Goodrich | |
| 2010/0240945 A1 | 9/2010 | Bikko | |
| 2011/0068935 A1 | 3/2011 | Riley et al. | |
| 2012/0150387 A1 | 6/2012 | Watson et al. | |
| 2013/0172770 A1 | 7/2013 | Muehlsteff | |
| 2013/0231579 A1 | 9/2013 | Shigeto | |
| 2013/0345921 A1 | 12/2013 | Al-Ali et al. | |
| 2014/0163343 A1 | 6/2014 | Heneghan et al. | |
| 2014/0276090 A1 | 9/2014 | Breed | |
| 2014/0276165 A1 | 9/2014 | Addison et al. | |
| 2014/0277822 A1 | 9/2014 | Nunn et al. | |
| 2015/0193193 A1 | 7/2015 | Khaira et al. | |
| 2015/0223731 A1 | 8/2015 | Sahin | |
| 2015/0325270 A1 | 11/2015 | Utsunomiya et al. | |
| 2016/0151603 A1 | 6/2016 | Shouldice et al. | |
| 2016/0357185 A1 | 12/2016 | Laur et al. | |
| 2017/0143253 A1 | 5/2017 | Krenzer et al. | |
| 2017/0180911 A1 | 6/2017 | Burton | |
| 2017/0212235 A1 | 7/2017 | Qiu et al. | |
| 2017/0232915 A1 | 8/2017 | Dufford | |
| 2017/0341658 A1 | 11/2017 | Fung et al. | |
| 2017/0347951 A1 | 12/2017 | Gollakota et al. | |
| 2018/0022358 A1 | 1/2018 | Fung et al. | |
| 2018/0157330 A1* | 6/2018 | Gu .......................... G01S 7/415 |
| 2018/0203451 A1 | 7/2018 | Cronin et al. | |
| 2018/0287651 A1* | 10/2018 | Fernando ............. H04B 1/3838 |
| 2018/0290020 A1 | 10/2018 | Mssa et al. | |
| 2019/0133511 A1 | 5/2019 | Migneco et al. | |
| 2020/0365275 A1 | 11/2020 | Barnett et al. | |
| 2021/0150873 A1* | 5/2021 | Shouldice .......... G08B 21/0469 |
| 2023/0248935 A1 | 8/2023 | Shouldice et al. | |

FOREIGN PATENT DOCUMENTS

| | | |
|---|---|---|
| CN | 106456000 A | 2/2017 |
| CN | 106913339 A | 7/2017 |
| CN | 107405081 A | 11/2017 |
| CN | 108113706 A | 6/2018 |
| DE | 10259522 A1 | 7/2004 |
| DE | 102008038022 A1 | 3/2009 |
| DE | 102015122245 A1 | 6/2017 |
| EP | 1308812 A2 | 5/2003 |
| EP | 2637385 A2 | 9/2013 |
| EP | 2638855 A1 | 9/2013 |
| FR | 3028741 A1 | 5/2016 |
| JP | 2003141676 A | 5/2003 |
| JP | 2005537721 A | 12/2005 |
| JP | 2006510880 A | 3/2006 |
| JP | 2010012018 A | 1/2010 |
| JP | 2010067164 A | 3/2010 |
| JP | 2012239748 A | 12/2012 |
| JP | 2013195351 A | 9/2013 |
| JP | 2014138661 A | 7/2014 |
| JP | 2014200681 A | 10/2014 |
| JP | 2014235078 A | 12/2014 |
| JP | 2016107095 A | 6/2016 |
| JP | 2016145028 A | 8/2016 |
| JP | 2016532481 A | 10/2016 |
| JP | 2016193020 A | 11/2016 |
| JP | 2017064338 A | 4/2017 |
| JP | 2017100039 A | 6/2017 |
| JP | 2017124058 A | 7/2017 |
| JP | 2017174397 A | 9/2017 |
| KR | 20150072821 A | 6/2015 |
| KR | 20170015214 A | 2/2017 |
| WO | 2004021134 A2 | 3/2004 |
| WO | 2004100100 A1 | 11/2004 |
| WO | 2008057883 A2 | 5/2008 |
| WO | 2007143535 A3 | 8/2008 |
| WO | 2010036700 A1 | 4/2010 |
| WO | 2010091168 A1 | 8/2010 |
| WO | 2013177621 A1 | 12/2013 |
| WO | 2014015238 A1 | 1/2014 |
| WO | 2014047310 A1 | 3/2014 |
| WO | 2015006364 A2 | 1/2015 |
| WO | 2015041892 A1 | 3/2015 |
| WO | 2015054134 A1 | 4/2015 |
| WO | 2015061848 A1 | 5/2015 |
| WO | 2015179911 A1 | 12/2015 |
| WO | 2016021235 A1 | 2/2016 |
| WO | 2016093927 A2 | 6/2016 |
| WO | 2016145483 A1 | 9/2016 |
| WO | 2016170005 A1 | 10/2016 |
| WO | 2016170011 A1 | 10/2016 |
| WO | 2016188826 A1 | 12/2016 |
| WO | 2017024085 A1 | 2/2017 |
| WO | 2017029284 A1 | 2/2017 |
| WO | 2017029317 A1 | 2/2017 |
| WO | 2017032873 A2 | 3/2017 |

(56) References Cited

FOREIGN PATENT DOCUMENTS

| WO | 2017097907 A1 | 6/2017 |
|----|---------------|--------|
| WO | 2017098609 A1 | 6/2017 |
| WO | 2017100605 A1 | 6/2017 |
| WO | 2017102614 A1 | 6/2017 |
| WO | 2017167731 A1 | 10/2017 |
| WO | 2018033574 A1 | 2/2018 |
| WO | 2018050913 A1 | 3/2018 |

OTHER PUBLICATIONS

PCT International Search Report issued in corresponding PCT application No. PCT/EP2018/086764 on May 29, 2019.
"Sleep as Android", https://sleep.urbandroid.org/ https://sleep.urbandroid.org/documentation/.
Condliffe, Jamie, "This App Lets You Control Your Phone Using Sonar", https://www.technologyreview.com/s/602834/this-app-lets-you-control-your-phone-using-sonar/, Nov. 15, 2016.
Nandakumar, Rajalakshmi, et al., "Contactless Sleep Apnea Detection on Smartphones", May 18, 2015.
Sangeetha, M., et al., "Embedded ECG Based Real Time Monitoring and Control of Driver Drowsiness Condition", http://article.sciencepublishinggroup.com/html/10.11648.j.ijsts.20150304.17.html, Jul. 2015.
Shin, Heung-Sub, "Real Time Car Driver's Condition Monitoring System", http://web.ee.nchu.edu.tw/~ljh/paper/Real Time Car Driver's Condition Monitoring System.pdf, Jul. 2010.
Wang, Xuyu, et al., "SonarBeat: Sonar Phase for Breathing Beat Monitoring with Smartphones", Department of Electrical and Computer Engineering, Auburn University, Auburn, AL 36849-5201, USA, Aug. 3, 2017.
Office Action for corresponding EP Application No. 18833058.3-1113 dated Jul. 15, 2022.
Office Action for European Patent Application No. 18833244.9, Jul. 1, 2022.
Examination Report issued in corresponding EP application No. 18833058.3 on Jan. 4, 2022.
Examination Report issued in corresponding EP application No. 18833244.9 on Jan. 3, 2022.
Final OA mailed Mar. 8, 2022 for U.S. Appl. No. 15/733,162.
Non Final Office Action mailed Sep. 21, 2021 for U.S. Appl. No. 15/733,162.
Office Action from corresponding CN Application No. 201880087497.1 dated Jan. 18, 2023.
Restriction Requirement Office Action dated Jun. 14, 2021 for U.S. Appl. No. 15/733,162.
"SleepScore", https://www.medgadget.com/2017/11/sleepscore-labs-releases-contact-free-sleep-monitoring-system.html, Nov. 15, 2017.
"SleepScore", https://www.sleepscore.com/sleepscore-high-low/, Dec. 8, 2017.
First Office Action issued in corresponding Chinese Patent Application No. 201880087490.X, mailed Dec. 5, 2022, 30 pages.
Office Action issued in corresponding Korean Patent Application No. 10-2020-7021037, mailed Feb. 28, 2023, 22 pages.
Office Action issued in corresponding Japanese Patent Application No. 2020-534935, mailed Sep. 1, 2023, 10 pages.
Office Action issued in corresponding Korean Patent Application No. 10-2020-7021041, mailed Feb. 16, 2024, 19 pages.
Extended European Search Report issued in corresponding European Patent Application No. 24159813.5, mailed May 28, 2024, 8 pages.
Notice of Allowance issued in corresponding Japanese Patent Application No. 2020-534935, mailed May 28, 2024, 8 pages.

\* cited by examiner

APPARATUS, SYSTEM, AND METHOD FOR HEALTH AND MEDICAL SENSING

1 CROSS REFERENCE TO RELATED APPLICATIONS

The present application is a national phase entry under 35 U.S.C. § 371 of International Application No. PCT/EP2018/086762 filed Dec. 21, 2018, published in English, which claims priority from U.S. Provisional Patent Application No. 62/610,033 filed Dec. 22, 2017, the disclosures of all of which are incorporated herein by reference.

2 BACKGROUND OF THE TECHNOLOGY

2.1 Field of the Technology

The present technology relates to detecting bio-motion associated with living subjects. More particularly, the present technology relates to using acoustic, radio frequency and/or infrared sensing to detect physiological characteristics such as from physiological movement such as breathing movement, cardiac movement and/or other less cyclical body movement of a living subject.

2.2 Description of the Related Art

Monitoring the breathing and body (including limb) movement of a person, for example, during sleep, can be useful in many ways. For example, such monitoring could be useful in monitoring and/or diagnosing sleep disordered breathing conditions, such as sleep apnea. Traditionally, the barrier to entry for active radio location or ranging application is that specialized hardware circuitry and antennas are required.

Smartphones and other portable and inconspicuous processing or electronic communication devices have been ubiquitous in daily life, even in developing countries where landlines are not available. It would be desirable to have a method for monitoring bio-motion (i.e., physiological movement) in an efficient, effective manner. The realization of such a system and method would address a considerable technical challenge.

3 BRIEF SUMMARY OF THE TECHNOLOGY

The present technology concerns systems, methods, and apparatus for detecting movement of a subject, for example, while the subject is asleep. Based on such movement detection, including for example breathing movement, the subject's movements, sleep related characteristics, respiratory characteristics, cardiac characteristics, sleep state and/or apnea and other sleep disordered breathing events may be detected. More particularly, an application associated with a processing device, such as a smartphone, tablet, smart speaker etc. uses the processing device sensors, such as an integrated, and/or externally connectable, speaker and microphone to detect breathing and motion. The meaning of the terms "device" and "system" are used herein in a broad sense which is not necessarily limited to a single piece of hardware. Any of these terms can encompass a single device, as well as one or more distinct devices. Some or all of these could be integrated in a single piece of equipment, or located separately and remotely from each other. The "device" or "system" is capable of transmitting and/or sensing reflected signals, such as with one or more transmitters and/or sensor(s) (i.e. speaker(s), microphone(s), infrared sensors, radio frequency transmitter/receiver etc.) being either integrated, and/or externally connectable) to detect physiological movement.

Some versions of the present technology may include a processor-readable medium, having stored thereon processor-executable instructions which, when executed by a processor, cause the processor to detect physiological parameters such as physiological movement of a user. Physiological movement may include any one or more of respiration movement, cardiac movement, limb movement, gesture movement and gross body movement. Apart from the physiological movement, which is a parameter that is derived from at least the detected reflected signal, physiological parameters may also include one or more characteristics that can be further derived from the detected physiological movement (e.g., respiratory amplitude, relative respiratory amplitude, respiratory rate and respiratory rate variability, derived from the respiratory movement signal; relative cardiac amplitude, cardiac amplitude, cardiac rate and cardiac rate variability, derived from the cardiac movement signal; etc.), as well as other characteristics (e.g., (a) presence state (present or absent); (b) sleep state, such as, awake or asleep; (c) sleep stage such as N-REM 1 (non-REM light sleep sub-stage 1), N-REM 2 (non-REM light sleep sub-stage 2), N-REM 3 (non-REM deep sleep (also referred to as slow wave sleep (SWS))), REM sleep etc.; or other sleep-related parameters such as (d) fatigue and/or (e) sleepiness; etc.). The processor-executable instructions may comprise instructions to control producing, via a speaker coupled to an electronic processing device, a sound signal in a vicinity that includes a user. The processor-executable instructions may comprise instructions to control sensing, via a microphone coupled to the electronic processing device, a sound signal reflected from the user. The processor-executable instructions may comprise instructions to process the sensed sound signal. The processor-executable instructions may comprise instructions to detect any one or more of a breathing signal, a cardiac signal and a gross body movement signal from the processed sound signal.

Some versions of the present technology may include a processor-readable medium, having stored thereon processor-executable instructions which, when executed by a processor, cause the processor to detect physiological movement of a user. The processor-executable instructions may include instructions to control producing, via a speaker coupled to an electronic processing device, a sound signal in a vicinity of the electronic processing device. The processor-executable instructions may include instructions to control sensing, via a microphone coupled to the electronic processing device, a reflected sound signal from the vicinity. The processor-executable instructions may include instructions to derive a physiological movement signal with at least a portion of the sensed reflected sound signal and a signal representative of at least a portion of the sound signal. The sound signal may include a dual tone frequency modulated continuous wave signal.

In some versions, at least a portion of the produced sound signal, such as that used for sensing, may be in an inaudible sound range. The portion of produced sound signal may be a low frequency ultrasonic acoustic signal. The processor-executable instructions to derive the physiological movement signal may be configured for demodulation of the portion of the sensed reflected sound signal with the signal representative of the portion of the sound signal. The demodulation may include a multiplication of the signal representative of the portion of the sound signal, and the portion of the sensed reflected sound signal. The demodulation to derive the physiological movement signal may include a multiplication of the portion of the sensed reflected sound signal with itself, the portion of the sensed reflected sound signal further including direct path sound from at least a portion of the sound signal. The instructions to derive the physiological movement signal may be configured to derive the physiological movement signal (a) with at least a portion of the sound signal and the portion of the sensed reflected sound signal or (b) with the portion of the sensed reflected sound signal and an associated signal that may be associated with at least a portion of the sound signal. The associated signal may be an internally generated oscillator signal or a direct path measured sound signal. The instructions to derive the physiological movement signal may be configured to multiply an oscillator signal with the portion of the sensed reflected sound signal. The derivation of the physiological movement signal may further include detection of one or more of respiration, cardiac and gross movement.

In some versions, the medium may include processor-executable instructions to filter the portion of the sensed reflected sound signal with an adaptive filter configured to change a passband of the adaptive filter based on any one of a timing of at least a portion of the produced sound signal and a timing of the portion of the sensed reflected sound signal. The medium may include processor-executable instructions to sum the sound signal and audible audio content to produce the sound signal and the audible audio content simultaneously via the speaker. The medium may further include processor-executable instructions to filter the audible audio content based on frequencies of the sound signal before summing the sound signal and audible audio content. The medium may further include processor-executable instructions to control a variation of a detection scheme of the sound signal depending on detected presence of a subject in the vicinity, wherein the instructions vary waveform parameters of at least a portion of the sound signal. The medium may further include processor-executable instructions to generate a continuous wave sound signal for motion detection, and to initiate, upon detection of user motion in the vicinity, producing the dual tone frequency modulated continuous wave signal via the speaker. The medium may further include processor-executable instructions to generate an ultra-wide band (UWB) sound signal as audible white noise, and wherein the processor-readable medium may include instructions to detect user motion with the UWB sound signal. The dual tone frequency modulated continuous wave signal may include a first sawtooth frequency change overlapped with a second sawtooth frequency change in a repeated waveform. The produced sound signal may provide a cosine-like functional time domain shape including zero crossings.

In some versions, the medium may include processor-executable instructions to evaluate the derived physiological movement signal to determine one or more physiological parameters. The medium may further include processor-executable instructions to generate an output based on an evaluation of the derived physiological movement signal. The medium may include processor-executable instructions to process the physiological movement signal to output data. The output or generated output may represent or comprise: (a) output data comprising, representing or indicating any one of more of: a human presence state; presence or absence of motion in the physiological movement signal; a sleep state; sleep walking; a breathing characteristic; a cardiac characteristic; a gross body movement characteristic; a sleep characteristic; an event of sleep disordered breathing; an event of periodic breathing; a respiratory condition; a fatigue condition; a wellness score; a chronic disease condition; a sleepiness condition; and a fatigue condition; or (b) initiating an event based on any of the above type of output data. The initiated event may include setting or turning a device, or a process associated with the device, on or off; and/or introducing an adjustment to the operation of a device, or a process associated with the device. The device may be a respiratory therapy device, and/or the process may be associated with a respiratory therapy device. The medium may include processor-executable instructions to evaluate an audible verbal command sensed via the microphone and to provide the output via the speaker in response to the audible verbal command. The medium may further include processor-executable instructions to demodulate at least a portion of the sound signal and the portion of the sensed reflected sound signal to produce quadrature baseband motion signals. The medium may include processor-executable instructions to process the quadrature baseband motion signals by one or more filters to isolate a frequency range attributable to one or more of respiration movement, gross body movement and cardiac movement. The medium may include processor-executable instructions to bin search in fast Fourier transform windows derived with the physiological movement signal to select a range associated with user motion.

In some versions, the medium may include processor-executable instructions to detect and recognize an audible sound of a respiratory pressure therapy device sensed by the microphone. The medium may further include processor-executable instructions to detect user presence from the physiological movement signal and activate a process of a respiratory therapy device based on detected presence and a sleep time. The medium may further include processor-executable instructions to detect user sleep from the physiological movement signal and activate a process of a respiratory therapy device based on the detected user sleep. The medium may include processor-executable instructions to detect user sleep from the physiological movement signal and deactivate a heat appliance based on detected user sleep. The medium may further include processor-executable instructions to detect a cardiac variability and correlate the cardiac variability with respect to a present and absent respiratory therapy. The medium may further include processor-executable instructions to play an audible query through the speaker in response to an analysis of the physiological movement signal. The analysis of the physiological movement signal may include a detection of an absence of motion in the physiological movement signal. The medium may include processor-executable instructions to detect an event of sleep walking based on analysis of the physiological movement signal. The medium may further include processor-executable instructions to correlate detected movement and therapy compliance. The medium may further include processor-executable instructions to infer therapy non-compliance for a user based on a detection of sleep quality of another user. The medium may further include processor-executable instructions to detect therapy non-compliance and compliance based on sound detection of operation and lack of operation of a therapy device.

In some versions, the medium may include processor-executable instructions to generate output advice based on detected therapy compliance or non-compliance of a user, the generated output advice based on sleep detection from multiple users including the user, the generated output advice may be to urge the user to maintain compliance, and may optionally be directed to the multiple users. The medium may further include processor-executable instructions to chirp filter sound sensed by the microphone to isolate the portion of the sensed reflected sound signal. To chirp filter, the processor may perform digital filtering with a pass band in a frequency range of the produced sound signal. The medium may further include processor-executable instructions to selectively change modulation parameters of production of at least a portion of the sound signal to sense motion in the vicinity of the electronic processing device with different sound signal modulation characteristics. The different sound signal modulation characteristics comprise any two or more of continuous wave (CW), frequency modulated continuous wave (FMCW), ultra-wide band (UWB), frequency-shift keying (FSK) and phase-shift keying (PSK). In some versions, the instructions of the medium may include processor-executable instructions related to synchronization including a cross-correlation of a sensed reflected signal with a sensed direct path signal. The instructions may comprise a synchronization process comprising multiplying a reference template with at least a portion of the sensed reflected sound signal.

In some versions, the medium may include processor-executable instructions to generate an output generated by classifying features of the physiological movement signal wherein the features may include hand-crafted features and/or machine-learned features. In some cases, a feature of the machine learned features may be derived by a deep belief network. The output generated by classifying features of the physiological movement signal may include a sleep stage and/or a sleep state may include one or more of: a sleep stage and/or a sleep state; an event of sleep disordered breathing; and an apnea-hypopnea count. The output generated by classifying features of the physiological movement signal may include a sleep stage and/or a sleep state. The output generated by classifying features of the physiological movement signal may include an event of sleep disordered breathing. The medium may include processor-executable instructions to generate an apnea-hypopnea count based on the output generated by classifying features of the physiological movement signal. The medium may include processor-executable instructions to generate therapy usage advice based on the generated apnea-hypopnea count. The medium may include processor-executable instructions to correlate generated apnea-hypopnea counts with use and non-use of respiratory therapy apparatus. The electronic processing device may include a smart phone and/or a smart watch. In some versions, the electronic processing device may be control operations of a respiratory therapy apparatus, and the electronic processing device may include processor control instructions, on a suitable processor-readable medium, wherein the instructions control, activation of, deactivation of, or parameters for, a respiratory therapy based on at least a portion of the derived physiological movement signal, or processing thereof.

Some versions of the present technology may include a server. The server may be configured with access to any of the processor-readable medium(s) described herein. The server may be configured to receive requests for downloading the processor-executable instructions of the processor-readable medium to the electronic processing device over a network.

Some versions of the present technology may include an electronic processing device. The electronic processing device may include one or more processors. The electronic processing device may include a speaker coupled to the one or more processors. The electronic processing device may include a microphone coupled to the one or more processors. The electronic processing device may include any of the processor-readable medium(s) described herein and/or may be configured to access the processor executable instructions with any of the server(s) described herein. The electronic processing device may be one of a mobile phone or a smart speaker. The electronic processing device may be a respiratory pressure therapy device.

Some versions of the present technology may include a method of a server having access to any of the processor-readable medium(s) described herein. The method may include receiving, at the server, a request for downloading the processor-executable instructions of the processor-readable medium to a processing device over a network; and transmitting the processor-executable instructions to the electronic processing device in response to the request.

Some versions of the present technology may include a method of a processor for detecting body movement using an electronic processing device. The method may include accessing, with a processor, any processor-readable medium described herein. The method may include executing, in the processor, the processor-executable instructions of the processor-readable medium.

Some versions of the present technology may include a method of a processor for detecting movement using an electronic processing device. The method may include controlling producing, via a speaker coupled to the processing device, a sound signal in a vicinity of the electronic processing device. The method may include controlling sensing, via a microphone coupled to the processing device, a reflected sound signal from the vicinity. The method may include controlling, in the processor, deriving of a physiological movement signal with at least a portion of the sensed reflected sound signal and a signal representative of at least a portion of the sound signal. The sound signal may include a dual tone frequency modulated continuous wave signal.

In some versions, at least a portion of the produced sound signal, such as that portion used for sensing, may be in an inaudible sound range. The portion of the produced sound signal may be a low frequency ultrasonic acoustic signal. The deriving the physiological movement signal may include demodulation of the portion of the sensed reflected sound signal with the signal representative of the portion of the sound signal. The demodulation may include a multiplication of the signal representative of the portion of the sound signal, and the portion of the sensed reflected sound signal. Demodulation to derive the physiological movement signal may include a multiplication of a received signal with itself, the received signal including the portion of the sensed reflected sound signal and direct path sound from at least a portion of the sound signal. The physiological movement signal may be derived (a) with at least a portion of the sound signal and the portion of the sensed reflected sound signal or (b) with the portion of the sensed reflected sound signal and an associated signal that may be associated with at least a portion of the sound signal. The signal representative of the portion of the sound signal may be an internally generated oscillator signal or a direct path measured sound signal. The associated signal may be an internally generated oscillator signal or a direct path measured sound signal.

In some versions, deriving the physiological movement signal may include multiplying an oscillator signal with the portion of the sensed reflected sound signal. The method may include filtering the portion of the sensed reflected sound signal with an adaptive filter configured to change a passband of the adaptive filter based on any one of a timing of at least a portion of the produced sound signal and a timing of the portion of sensed reflected sound signal. The method may further include combining the sound signal and audible audio content to produce the sound signal and the audible audio content simultaneously via the speaker. The method may further include filtering the audible audio content based on frequencies of the sound signal before summing the sound signal and audible audio content. The method may further include controlling a variation of a detection scheme of the sound signal depending on detected presence of a subject in the vicinity, wherein the variation may include changing waveform parameters of the sound signal. Deriving the physiological movement signal may further include detecting one or more of respiration, cardiac and gross movement.

In some versions, the method may further include generating a continuous wave sound signal for motion detection. The method may include, upon detection of user motion in the vicinity with the continuous wave sound signal, initiating producing the dual tone frequency modulated continuous wave signal via the speaker. The method may further include generating an ultra-wide band (UWB) sound signal as audible white noise; and detecting user motion with the UWB sound signal. The dual tone frequency modulated continuous wave signal may include a first sawtooth frequency change overlapped with a second sawtooth frequency change in a repeated waveform. The produced sound signal may provide a cosine-like functional time domain shape including zero crossings. The method may include evaluating the derived physiological movement signal to determine one or more physiological parameters. The method may further include generating an output based on an evaluation of the derived physiological movement signal. The generated output may include any one or more of: (a) output data comprising, representing or indicating any one or more of: a human presence state; presence or absence of motion in the physiological movement signal; a sleep state; a breathing characteristic; sleep walking; a cardiac characteristic; a gross body movement characteristic; a sleep characteristic; an event of sleep disordered breathing; an event of periodic breathing; a respiratory condition; a fatigue condition; a wellness score; a chronic disease condition; a sleepiness condition; and a fatigue condition; or (b) initiating an event based on any of the above output data. The initiated event may include includes setting or turning a device, or a process associated with the device, on or off; and/or introducing an adjustment to the operation of a device, and/or a process associated with the device. The device may be a respiratory therapy device, and/or the process may be associated with a respiratory therapy device.

In some versions, the method may include evaluating, in the processor, an audible verbal command sensed via the microphone and to provide, in response to the audible verbal command, the output via the speaker. The method may further may include demodulating at least a portion of the sound signal and the portion of the sensed reflected sound signal to produce quadrature baseband motion signals. The method may include processing the quadrature baseband motion signals by one or more filters to isolate a frequency range attributable to one or more of respiration movement, gross body movement and cardiac movement. The method may include bin searching in fast Fourier transform windows derived with the physiological movement signal to select a range associated with user motion. The method may include, in the processor, detecting and recognizing an audible sound of a respiratory pressure therapy device sensed by the microphone. The method may further include detecting, in the processor, user presence from the physiological movement signal and activating a process of a respiratory therapy device based on detected presence and a sleep time. The method may further include detecting user sleep from the physiological movement signal and activating a process of a respiratory therapy device based on detected user sleep. The method may further include detecting user sleep from the physiological movement signal and deactivating a heat appliance based on the detected user sleep. The method may further may include detecting a cardiac variability and correlating the cardiac variability with respect to a present and absent respiratory therapy.

In some version, the method may include playing an audible query through the speaker in response to an analysis of the physiological movement signal. The analysis of the physiological movement signal may include detecting an absence of motion in the physiological movement signal. The method may further include detecting an event of sleep walking based on analysis of the physiological movement signal. The method may further include correlating detected movement and therapy compliance. The method may further include inferring therapy non-compliance for a user based on a detection of sleep quality of another user. The method may further include detecting therapy non-compliance and compliance based on sound detection of operation and lack of operation of a therapy device. The method may further include generating output advice based on detected therapy compliance or non-compliance of a user, the generated output advice based on sleep detection from multiple users including the user, the generated output advice may urge the user to maintain compliance. Such advice may be directed to directed to the multiple users. The method may further include chirp filtering sound sensed by the microphone to isolate the portion of the sensed reflected sound signal. Optionally, a chirp filter may digitally filter, the chirp filtering, with a pass band in a frequency range of the produced sound signal.

In some versions, the method may further include selectively changing modulation parameters of production of at least a portion of the sound signal to sense motion in the vicinity of the electronic processing device with different sound signal modulation characteristics. The different sound signal modulation characteristics may include any two or more of continuous wave (CW), frequency modulated continuous wave (FMCW), ultra-wide band (UWB), frequency-shift keying (FSK) and phase-shift keying (PSK). The method may include generating an output by classifying features of the physiological movement signal wherein the features comprise hand-crafted features and machine-learned features. A feature of the machine learned features may be derived by a deep belief network. The output generated by classifying features of the physiological movement signal may include one or more of: a sleep stage and/or a sleep state; an event of sleep disordered breathing; and an apnea-hypopnea count. The output generated by classifying features of the physiological movement signal may include a sleep stage and/or a sleep state. The output generated by classifying features of the physiological movement signal may include an event of sleep disordered breathing. The method may include generating an apnea-hypopnea count based on the output generated by classifying features of the physiological movement signal. The method may further may include generating therapy usage advice based on the generated apnea-hypopnea count. The method may further may include correlating generated apnea-hypopnea counts with use and non-use of respiratory therapy apparatus. The electronic processing device may include a smart phone and/or a smart watch. The method may further include controlling a respiratory therapy based on the derived physiological movement signal, or processing thereof. The method may include, in a synchronization process, multiplying a reference template with at least a portion of the sensed reflected sound signal. The method may include, in a synchronization process, cross-correlating a sensed reflected signal with a sensed direct path signal.

The methods, systems, devices and apparatus described herein can provide improved functioning in a processor, such as of a processor of a general or specific purpose computer, portable computer processing device (e.g., mobile phone, tablet computer, smart speaker etc.), respiratory monitor and/or other respiratory apparatus utilizing a microphone and speaker. Moreover, the described methods, systems, devices and apparatus can provide improvements in the technological field of automated management, monitoring and/or prevention and/or evaluation of respiratory condition and sleep condition, including, for example, sleep apnea.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

5 DETAILED DESCRIPTION OF EXAMPLES OF THE TECHNOLOGY

Figure 1:
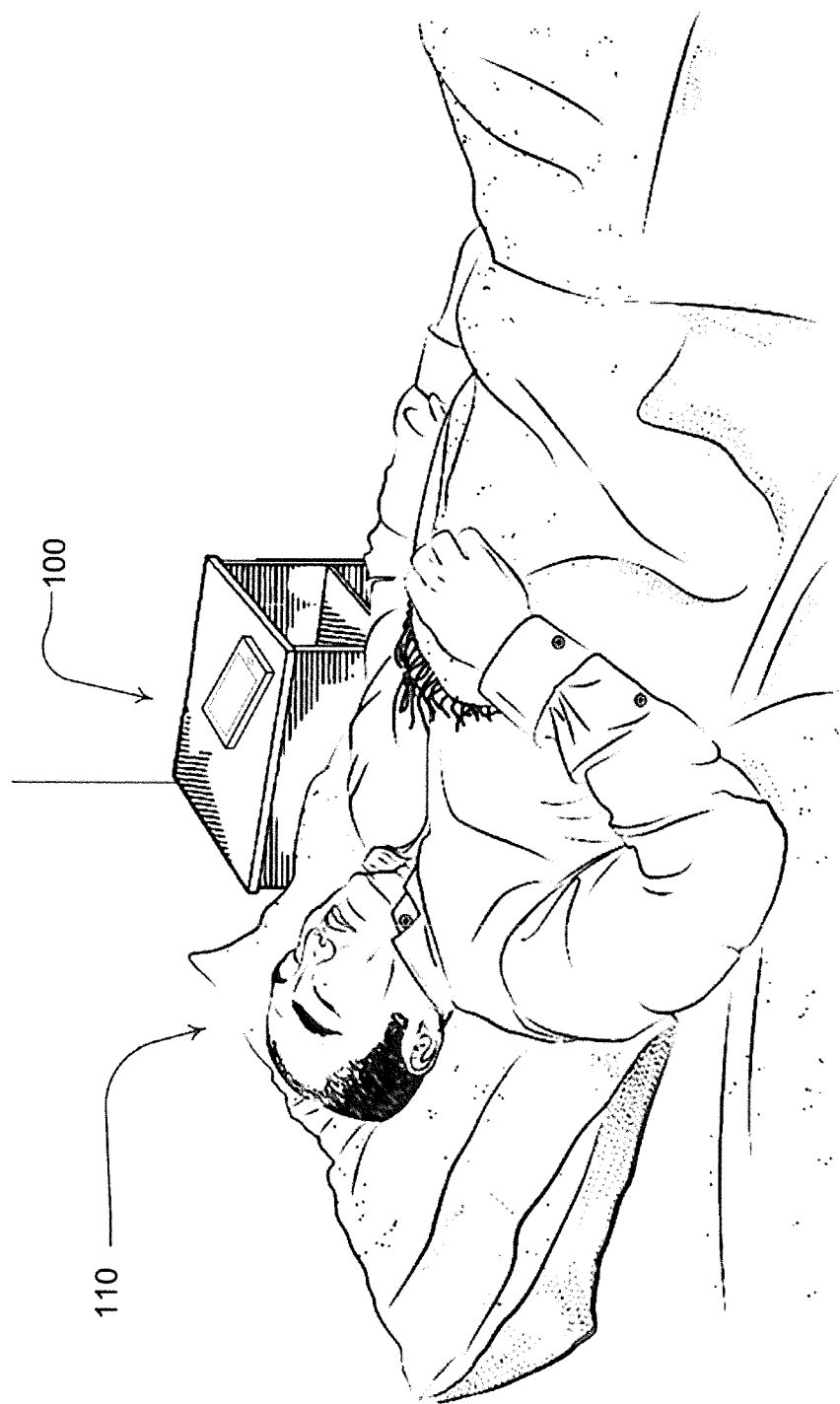
FIG. 1 illustrates an example processing device for receiving audio information from a sleeper that may be suitable for implementation of the processes of the present technology.

Before the present technology is described in further detail, it is to be understood that the technology is not limited to the particular examples described herein, which may vary. It is also to be understood that the terminology used in this disclosure is for the purpose of describing particular examples discussed and is not intended to be limiting.

The following description is provided in relation to various forms of the present technology that may share common characteristics or features. It is to be understood that one or more features of any one exemplary form may be combinable with one or more features of another form. In addition, any single feature or combination of features in any of form described herein may constitute a further exemplary form.

5.1 Screening, Monitoring, and Detection

The present technology concerns systems, methods, and apparatus for detecting movement of a subject, including, for example, breathing movement and/or cardiac related chest movement, such as while the subject is asleep. Based on such breathing and/or other movement detection, the subject's sleep state and apnea events may be detected. More particularly, a processing application associated with a processing device, such as a smartphone, tablet, mobile device, mobile phone, smart speaker etc. uses the device sensors, such as a speaker and microphone to detect such motion.

An example system suitable for implementing the present technology is now described with reference to FIGS. 1 to 5. A processing device 100, or mobile electronic device, configured with an application 200 for detecting movement of subject 110, may be placed on a bedside table near subject 110 or otherwise be located in a room. Processing device 100 may be, for example, a smartphone, smart speaker, smart watch, or tablet having one or more processors. The processor(s) may be configured to, among other things, execute the functions of application 200, including causing an audio signal to be generated and transmitted, typically through the air as a generally open or unrestricted medium such as in a room vicinity of the device. The processing device may receive a reflection of the transmitted signal by sensing it with, for example, a transducer such as a microphone. The processing device may process the sensed signal to determine body movement such gross body movement, cardiac movement and respiration movement. Processing device 100 may comprise, among other components, a speaker and a microphone. The speaker may be implemented to transmit the generated audio signal and the microphone to receive the reflected signal. The generated audio signal for sensing and processing may be implemented with any of the techniques described in International Patent Application PCT/EP2017/073613 filed on Sep. 19, 2017, the entire disclosure of which is incorporated herein by reference. Although the version illustrated in FIGS. 1 to 5 illustrate various processing devices with integrated sensing apparatus (e.g., where a housing includes all of the sensing apparatus or components such as the microphone and speaker), in some versions, the sensing apparatus may be discrete or separately housed components that couple or work together via wired and/or wireless connection(s).

Figure 5:
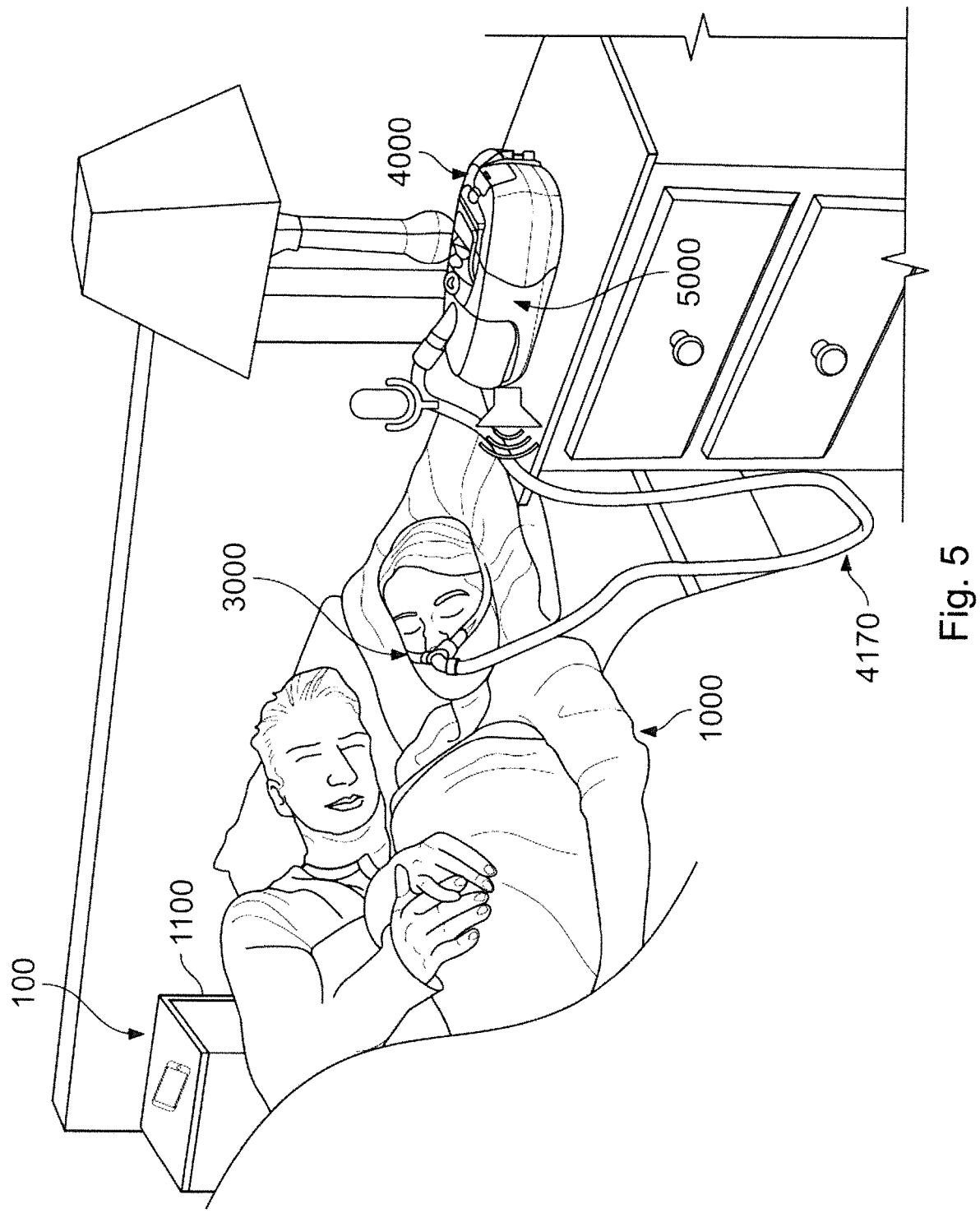
FIG. 5 illustrates an example system of processing devices operating in a common area, such as on a bed stand 1100, where one is a respiratory device (illustrated with a microphone and speaker) that is implemented for external low frequency ultrasonic sensing (enabled using transducers such as a speaker and microphone).

Optionally, the sound-based sensing methodologies of the processing device may be implemented in or by other types of devices such as a bedside device (e.g., a respiratory therapy device such as a continuous positive airway pressure (e.g., "CPAP") device or high flow therapy device) such as the respiratory therapy device 5000 illustrated in FIG. 5 where the therapy device serves as the processing device 100 or works in conjunction with a separate processing device 100. Examples of such devices, including a pressure device or blower (e.g., a motor and impeller in a volute), one or more sensors and a central controller of the pressure device or blower, may be considered in reference to the devices described in International Patent Publication No. WO/2015/061848 (Appl. No. PCT/AU2014/050315) filed on Oct. 28, 2014, and International Patent Publication No. WO/2016/145483 (Appl. No. PCT/AU2016/050117) filed on Mar. 14, 2016, the entire disclosures of which are incorporated herein by reference. Such a respiratory therapy device 5000 may include an optional humidifier 4000 and provide therapy to a patient interface 3000 via a patient circuit 4170 (e.g., a conduit). In some cases, the respiratory therapy device 5000 might have a separate sensor, such as a microphone, for sensing internal sound-related conditions within and through the patient circuit 4170, as opposed to serving to sense the externally sound related acoustic conditions of the processes described throughout this application.

Processing device 100 may be adapted to provide an efficient and effective method of monitoring a subject's breathing and/or other movement related characteristics. When used during sleep, the processing device 100 and its associated methods can be used to detect, for example, the user's breathing and identify sleep stages, sleep states, transitions between states, sleep-disordered breathing and/or other respiratory conditions. When used during wake, the processing device 100 and its associated methods can be used to detect movement such as presence or absence of a person or subject breathing (inspiration, expiration, pause, and derived rate) and/or ballistocardiogram waveform and subsequent derived heart rate, etc. Such parameters may be used for controlling a relaxation therapy (whereby a user is guided to reduce their respiration rate for relaxation purposes), or evaluating respiratory condition such as of a subject with a chronic disease such as COPD, asthma, congestive heart failure (CHF) etc., where the subject's baseline respiratory parameter(s) change in the time before an exacerbation/decompensation event occurs. The respiratory waveform may also be processed to detect temporary cessation of breathing (such as central apnea, or the small chest movements against an obstructive airway seen during an obstructive apnea) or reduction in breathing (shallow breathing and/or reduction in breathing rate, such as related to a hypopnea).

Processing device 100 may include integrated chips, a memory and/or other control instruction, data or information storage medium. For example, programmed instructions encompassing the assessment/signal processing methodologies described herein may be coded on integrated chips in the memory of the device or apparatus to form an application specific integrated chip (ASIC). Such instructions may also or alternatively be loaded as software or firmware using an appropriate data storage medium. Optionally, such processing instructions may be downloaded such as from a server over a network (e.g. an internet) to the processing device such that when the instructions are executed, the processing device serves as a screening or monitoring device.

Figure 3:
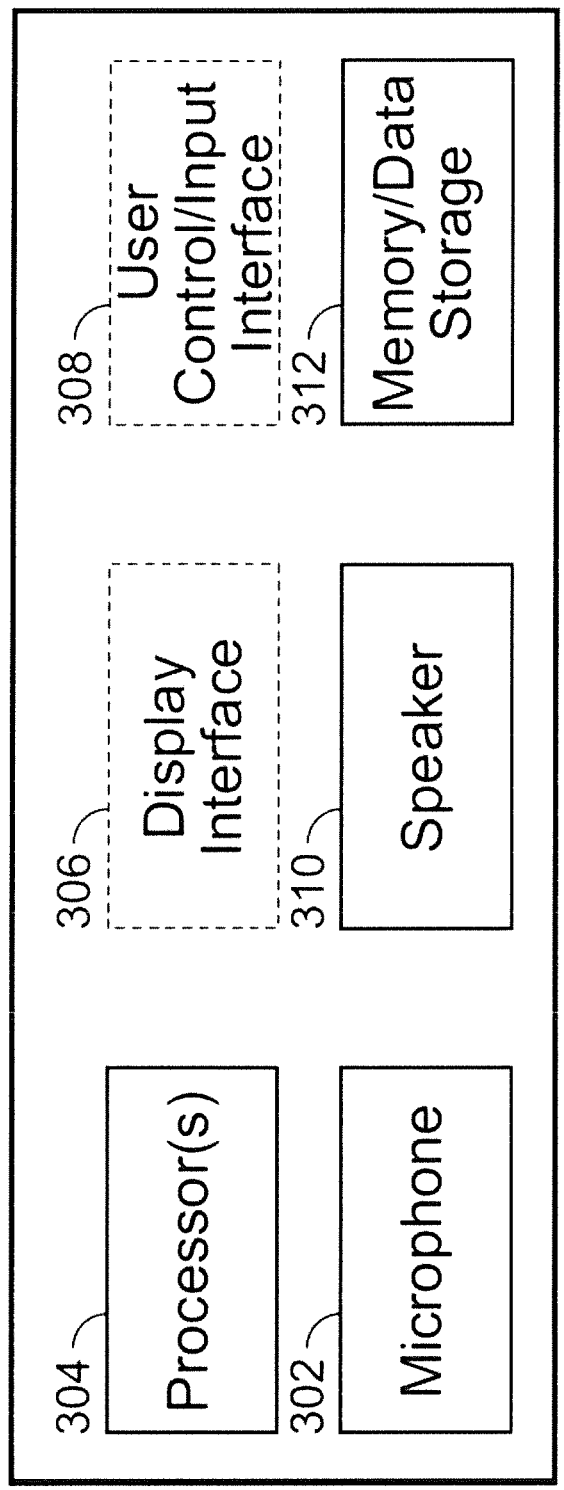
FIG. 3 is conceptual diagram of a processing device, such as a mobile device, configured in accordance with some forms of the present technology.

Accordingly, processing device 100 may include a number of components as illustrated by FIG. 3. The processing device 100 may include, among other components, a microphone or sound sensor 302, a processor(s) 304, an optional display interface 306, an optional user control/input interface 308, a speaker 310, and a memory/data storage 312, such as with the processing instructions of the processing methodologies/modules described herein. In some cases, the microphone and/or speaker may serve as the user interface, such as to control operations of the processing device, for example, when the processing device responds, such as via the speaker, to audio and/or verbal commands sensed by the microphone.

One or more of the components of processing device 100 may be integral with or operably coupled with processing device 100. For example, microphone or sound sensor 302 may be integral with processing device 100 or coupled with processing device 100 such as through a wired or wireless link (e.g., Bluetooth, Wi-Fi etc.).

Memory/data storage 312 may comprise a plurality of processor control instructions for controlling processors 304. For example, memory/data storage 312 may comprise processor control instructions for causing application 200 to be performed by the processing instructions of the processing methodologies/modules described herein.

Figure 2:
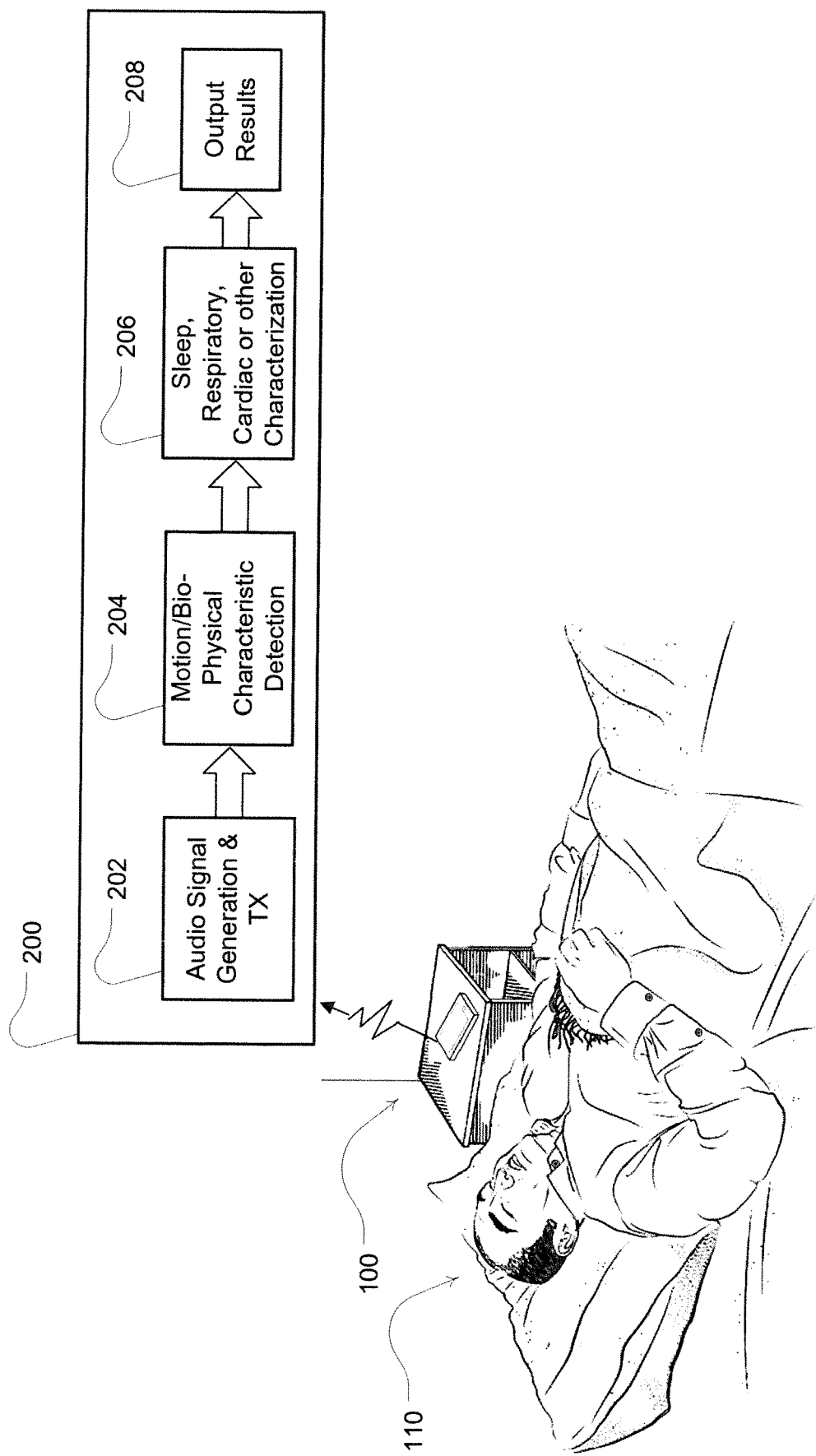
FIG. 2 is a schematic illustration of a system in accordance with an example of the present technology.

Examples of the present technology may be configured to use one or more algorithms or processes, which may be embodied by application(s) 200, to detect motion, breathing, and optionally sleep characteristics while a user is asleep using the processing device 100. For example, application 200 may be characterized by several sub-processes or modules. As shown in FIG. 2, application 200 may include an audio signal generation and transmission sub-process 202, a motion and bio-physical characteristic detection sub-process 204, a motion characterization sub-process 206 such as for sleep, respiratory or cardiac related characterizations, and a results output sub-process 208.

For example, optional sleep staging at processing 206, such as in a sleep staging processing module may be implemented. However, any one or more of such processing modules/blocks may optionally be added (e.g., sleep scoring or staging, fatigue indication processing, subject recognition processing, chronic disease monitoring and/or prediction processing, sleep disordered breathing event detection processing, or other output processing, etc.). In some cases, the functions of signal post-processing at may be performed using any of the components, devices and/or methodologies of the apparatus, system and method described in any of the following patents or patent applications, wherein the entire disclosures of each is incorporated by reference herein: International Patent Application No. PCT/US2007/070196, filed Jun. 1, 2007 and entitled "Apparatus, System, and Method for Monitoring Physiological Signs;" International Patent Application No. PCT/US2007/083155, filed Oct. 31, 2007, entitled "System and Method for Monitoring Cardio-Respiratory Parameters;" International Patent Application No. PCT/US2009/058020, filed Sep. 23, 2009, entitled "Contactless and Minimal-Contact Monitoring of Quality of Life Parameters for Assessment and Intervention;" International Application No. PCT/US2010/023177, filed Feb. 4, 2010, entitled "Apparatus, System, and Method for Chronic Disease Monitoring;" International Patent Application No. PCT/AU2013/000564, filed Mar. 30, 2013, entitled "Method and Apparatus for Monitoring Cardio-Pulmonary Health;" International Patent Application No. PCT/AU2015/050273, filed May 25, 2015, entitled "Methods and Apparatus for Monitoring Chronic Disease;" International Patent Application No. PCT/AU2014/059311, filed Oct. 6, 2014, entitled "Fatigue Monitoring and Management System;" International Patent Application No. PCT/AU2013/060652, filed Sep. 19, 2013, entitled "System and Method for Determining Sleep Stage;" International Patent Application No. PCT/EP2016/058789, filed Apr. 20, 2016, entitled "Detection and Identification of a Human from Characteristic Signals;" International Patent Application No. PCT/EP2016/069496, filed 17 Aug. 2016, entitled "Screener for Sleep Disordered Breathing;" International Patent Application No. PCT/EP2016/069413, filed Aug. 16, 2016, entitled "Digital Range Gated Radio Frequency Sensor;" International Patent Application No. PCT/EP2016/070169, filed Aug. 26, 2016, entitled "Systems and Methods for Monitoring and Management of Chronic Disease;", International Patent Application No. PCT/US2014/045814, filed Jul. 8, 2014, entitled "Methods and Systems for Sleep Management;" U.S. patent application Ser. No. 15/079,339, filed Mar. 24, 2016, entitled "Detection of Periodic Breathing." Thus, in some examples, the processing of detected movement, including for example, the breathing movement, may serve as a basis for determining any one or more of (a) a sleep state indicating sleep; (b) a sleep state indicating awake; (c) a sleep stage indicating deep sleep; (d) a sleep stage indicating light sleep; and (e) a sleep stage indicating REM sleep. In this regard, while the sound related sensing technologies of the present disclosure provide for different mechanisms/processes for motion sensing such as using a speaker and microphone and processing of the sound signals, when compared to radar or RF sensing technologies as described in these incorporated references, once a breathing signal, such as breathing rate is obtained with the sound sensing/processing methodologies described in this specification) the principles of processing breathing or other motion signal for an extraction of sleep states/stages information may be implemented by the determination methodologies of these incorporated references.

While the sensing apparatus are generally described herein in relation to acoustic sensing (e.g., low frequency ultrasonic sensing), it is understood that the methods and devices may be implemented using other sensing techniques. For example, as an alternative, the processing device may be implemented with a radio frequency (RF) transceiver of an RF sensor to serve as sensing apparatus, such that the generated signal and reflected signal are RF signals. Such a RF sensing device, which may be integrated with or coupled to the processing device, may implemented with any of the techniques and sensor components described in International Patent Application No. PCT/US2013/051250, entitled "Range Gated Radio Frequency Physiology Sensor" and filed on Jul. 19, 2013; International Patent Application No. PCT/EP2017/070773, entitled "Digital Radio Frequency Motion Detection Sensor" and filed on Aug. 16, 2017; and International Patent Application No. PCT/EP2016/069413, entitled "Digital Range Gated Radio Frequency Sensor" and filed on Aug. 16, 2017. Similarly, in alternative versions, such sensing apparatus for the transmission of a sensing signal and sensing of its reflection may be implemented with an infrared radiation generator and an infrared radiation detector (e.g., an IR emitter and IR detector). The processing of such signals for motion detection and characterization as described herein may be similarly implemented. For example, once the respiration rate and movement and activity counts are determined from motion whether by RF or SONAR, sleep staging is a common analysis. By way of additional example, the sensing wavelengths may be different between an RF pulsed CW and a SONAR FMCW implementation. Thus, velocity may be determined differently such as by detecting movement across a range (different sensing distances). For FMCW, movement detection may be made at multiple ranges. Thus, one or more moving targets may be tracked (whether it is two people, or indeed different parts of a person—depending on their angle with respect to the SONAR sensor).

Using a combination of two or more of these different sensing techniques, can enhance the sensing outcome by combining the advantages of the respective techniques. For instance, the discussed acoustic sensing technique is quite acceptable in the noisy environment of our daily life. However, a user with very sensitive hearing may find the use of this technique to be problematic at night, when the noise is much lower and the sensing signal is easier to hear. Similarly, whilst an IR sensing provides a good S/N signal during night time, its use may be problematic in the light (and heat) of day. An IR sensing may be used in this case at night, complemented by the use of the acoustic sensing during the day.

Typically, an audio signal from a speaker may be generated and transmitted towards a user for sensing such as an audio signal using one or more tones described herein. A tone provides pressure variation in a medium (e.g., air) at one or more particular frequencies. For purposes of this description, the generated tones (or audio signals or sound signals) may be referred to as "sound", "acoustic" or "audio" because they may be generated in a like manner to audible pressure waves (e.g., by a speaker). However, such pressure variations and tone(s) should be understood herein to be either audible or inaudible, notwithstanding their characterization by any of the terms "sound", "acoustic" or "audio." Thus, the audio signal generated may be audible or inaudible, wherein the frequency threshold of audibility across the human population varies by age. The signal may be substantially inaudible such that most people cannot discern the sound (e.g., in the range above 18 kHz). The typical "audio frequency" standard range is around 20 Hz to 20,000 Hz (20 kHz). The threshold of higher frequency hearing tends to reduce with age, with middle aged people often unable to hear sounds with frequencies above 15-17 kHz, whereas a teenager may be able to hear 18 kHz. The most important frequencies for speech are approximately in the range 250-6,000 Hz. Speaker and microphone signal responses for typical consumer smartphones are designed to roll off above 19-20 kHz in many cases, with some extending to above 23 kHz and higher (especially where the device supports a sampling rate of greater than 48 kHz such as 96 kHz). Therefore, for most people, it is possible to use signals in the range of 17/18 to 24 kHz and remain inaudible. For younger people that can hear 18 kHz but not 19 kHz, a band of 19 kHz to say 21 kHz could be employed. It is noted that some household pets may be able to hear higher frequencies (e.g., dogs up to 60 kHz and cats up to 79 kHz). A suitable range for the sensing audio signal of the present technology may be in a low ultrasonic frequency range such as 15 to 24 kHz, 18 to 24 kHz, 19 to 24 kHz, 15 to 20 kHz, 18 to 20 kHz or 19 to 20 kHz.

Background on Sensing Approaches—Low Frequency Ultrasonic and Radio Frequency

Audio devices such as speakers and microphones are widely used in the modern households. The advent of mobile and portable devices such as computers, laptops, tablets and smartphones, has seen this use extend even further, whilst at the same time complimenting their use with the availability of ever more powerful processors. However, the presence of at least one speaker and at least one microphone (or transducers that can be configured to perform these functions) allows new biometric sensing to be performed on these devices using active low frequency ultrasound, and processing the echoes of same. By playing (transmitting) an acoustic signal that is just outside human hearing (e.g., above 18 kHz) but within the system capability (e.g., below 24 kHz for a sampling rate of 48 kHz) but usually below 25 or 30 kHz. In contrast, medical ultrasound usually operates at much higher frequencies—for example 1-18 MHz. It can be seen that such sensing capability could be added to systems that already contain at least one speaker and microphone (or similar transducers) and a processor, with the addition of specialized sensing software implementing digital signal processing (DSP) functions. Additionally, specialized speakers and microphones may also be implemented depending on the desired sensing characteristics.

A radio frequency (RF) sensor such as a pulsed CW Doppler sensor operating in the 5.8 GHz ISM band or at 10.5 GHz (or 9.3 GHz) or a Silicon Germanium radar, operating in the 24 GHz ISM band (e.g., based on a 24 GHz fundamental voltage controlled oscillator (VCO) using FMCW or FSK, delivering a digitized I/Q (in phase and quadrature) might alternatively be used with some of the processes described herein, but such an implementation does typically require dedicated hardware.

The widespread availability of microphone/speaker systems facilitates the convenient use of ultrasonic sensing and can enable a range of new medical and health applications.

Example Acoustic Sensing Architecture

An example architecture of a system for detecting physiological signals may be as follows. A low frequency ultrasonic system operating up to around 25 kHz can realized on a mobile smart device or smart speaker device. This transmits sound energy towards one or more subjects using one or more transducers on the electronic device. The transducer is typically configured to generate sound energy over a range of frequencies that includes frequencies less than 25 kHz. The transducer may be in the form of a speaker contained in a smart speaker, a sound bar, a TV, a medical device (such as positive airway pressure (PAP) device), or many other devices and configurations that contain transducers capable of supporting low frequency ultrasonic sensing and processing. The physiological signals are sensed by receiving echoes from the subject corresponding to the transmitted sound energy using a second transducer on the electronic device, wherein the second transducer (such as a microphone) is configured to produce electrical signals corresponding to the received echoes, and to digitize them.

Detailed technical description of the hardware arrangement and signal processing associated with using ultrasonic systems to detect biometric characteristics is described in PCT/EP2017/073613, the entire disclosure of which is incorporated herein and the features of which may be implemented with a processing device described herein. Further technical details and various applications of that technology are described throughout this specification.

If such a system is, for example, implemented on a Linux based operating system platform, it may be desirable for the processor to communicate directly to ALSA (Advanced Linux Sound Architecture) using play and record commands. It is important to avoid digital audio play or record samples (e.g., 16 or 32 bit audio samples) being dropped, as this could introduce undesirable sound clicks (e.g., dropped samples causing phase discontinuities). The system could for example be multi-threaded (in the case where the processor has one or more cores, and can execute multiple processes or threads concurrently), and be implemented using a programming language such as Python, with a package such as NumPy.

Such lower level access to ALSA is also desirable, such as on Android smartphones based on Linux, where higher level audio operations (such as via Java or Open SL ES) may have micro pauses leading to undesirable audible clicking on some particular smartphones when the processor is heavily loaded and the application and/or audio is briefly paused by the operating system (e.g., on certain Samsung S7 devices).

Sensing Living Things

A "subject" is usually considered to be a person, but could also be an animal such as a pet dog, cat etc. Dogs may be able to hear up to 45 kHz, and cats up to 64 kHz, so the sensing frequency can optionally be increased to a band beyond their hearing range, and/or type of sensing sound produced be adjusted so as not to annoy an animal (e.g., to be more like a broad spectrum gentle hiss rather than a buzz).

The system can also be made to operate where there are no subjects in the sensing area, and to optionally adjust its operating mode (e.g., by changing the transmitted waveform parameters) to detect a disturbance (movement) over a much wider area. The system may switch to an alternative operations mode for fine grained (e.g., closer sensing) activity and biomotion detection only when a subject is detected. One realisation could be a device with one or more speakers (e.g., tweeters) and one or more microphones, which sends real time vital signs data to the cloud.

Sensing—Coexisting with Other Audio Digital Signal Processing (DSP)

For the sensing frequency/ies) and waveform shape/s in use by the speaker-produced acoustic signal of the processing device 100, 102, any existing echo cancellation in the device or associated hardware or software may be suppressed (e.g., disabled). Automatic gain control (AGC) and noise suppression can also be disabled, in order to minimize disturbance (processing of an unintended signal) of the reflected "echo" signal, which is often relatively small in amplitude.

The resulting received signal (e.g., received at the speaker) is digitally band pass filtered to separate the intended transmitted sensing waveforms from other signals at different frequencies (e.g., speech, background noise, a different sensing signal running in the same or co-located device etc.).

Sensing—Timing/Clocking of Acoustic Transmission and Reception

Depending on the accuracy over time (i.e., is there unwanted clock drift, temperature effects etc.) of the transmit/receive path, the received signal may need to be synchronized and re-synchronized periodically. For signals with a defined wave shape (such as an FMCW triangular (up-down—dual ramp) chirp, sinusoidal modulation, ramp etc.), a time or frequency domain collation can be performed to align the signals, and estimate the round-trip time. In other cases where accurate timing information is available, a computationally complex synchronization may not be needed.

Where two or more processing devices 100, 102 with different clocks are used, extra synchronization information can be exchanged (e.g., by wireless communications) between the devices. This can be done to make sure a particular transmitted waveform can be related to dominant echo (estimate time of flight). Usually this is done by comparing the sample waveform that is played, the direct path signal, and then the echo.

Sensing—Frontend FMCW Dual Ramp (e.g., Triangle) Example with Adaptive Filtering In some versions, the processing device may be implemented for sensing by generating an acoustic frequency modulated continuous wave (FMCW) signal with particular characteristics. An FMCW signal is a continuous signal with a linear frequency modulation, with a subsequent down conversion process yielding a "beat" frequency, where fixed targets located at different distance from the sensing system return different beat frequencies, regardless of their relative velocity. The "Beat frequency" is sometimes referred to as an "intermediate" frequency (IF). With FMCW, when the receive Rx signal is demodulated, such as by a local oscillator or by itself as described in more detail herein, and low pass filtered, it produces an unusual "intermediate" signal that is not yet considered to be baseband. The IF signal may be processed, such as by application of fast Fourier transform processing (FFT), to become baseband. (See, e.g., FIG. 10).

Typically, the received signal is digitally band pass filtered (a band pass filter (BPF)) to remove frequency components not related to the expected echoes of the transmitted waveform. Such a BPF may be implemented using a finite impulse response (FIR) filter, infinite impulse response (IIR) filter or other approach, and will have a passband defined so as to include the frequency of the echoes. A simple example would be to transmit an acoustic sensing waveform using a FMCW signal that changes the frequency by ramping frequencies from 19 to 21 kHz and back to 19 kHz using a triangular ramping strategy (e.g., 1500 samples up, 1500 samples down, at an audio sampling rate of 48 kHz leading to an effective sensing sampling rate of 16 Hz), with no phase discontinuities; in this case, the BPF would be designed to have a passband covering this frequency range, with 3 dB points selected below and above the edges so as to not unduly impact the signal, and limited or no ripple in the passband.

A more advanced filter that may be used as the BPF, in relation to sensing with an FMCW signal, can use knowledge of the timing of the transmitted chirp (the ramped frequency), and of the expected echo (in time). Such a filter may adaptively change (i.e., an adaptive) and have a much narrower passband, by tracking the expected frequency content. This permits better suppression of signals at unwanted frequency/ies and can help to combat intermittent in-band interference. As discussed in more detail herein, ultrasonic sensing technology may be implemented with dual tone acoustic signals. For the case of a dual tone continuous wave (CW) signal, the different tones can be isolated by one or more filters (such as a filter bank) in order to better isolate the frequencies of interest. If frequency hopping continuous wave (FHCW) is implemented on the transmit, the digital filter(s) can be configured to track the expected echo frequency content in time, and reject other frequencies.

The signal processing applied can provide good signal-to-noise (SNR)—even from relatively low amplitude ultrasonic sensing.

Information on the SNR of the system is available both before and after demodulation—such as based on the envelope of the received signal, as well as on the demodulated (e.g., using techniques such as phase demodulation or differential phase demodulation) I/Q signals, and subsequent biometric detection.

Figure 6:
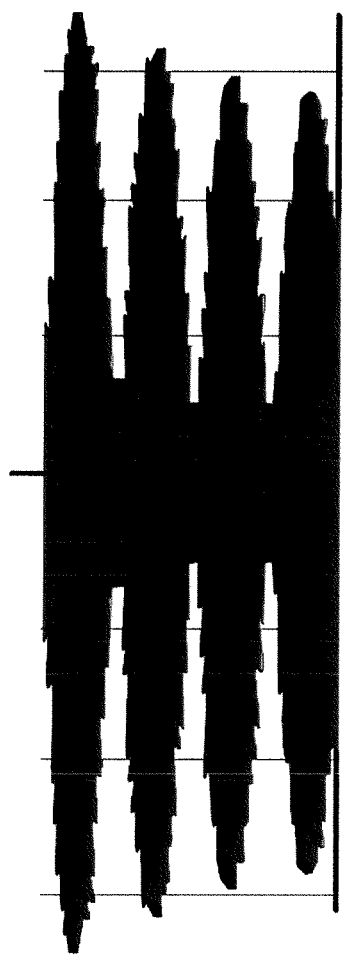
FIG. 6 illustrates a multi-tone pair that may be implemented as part of a frequency hopping range gating sensing.

FIG. 6 illustrates a multi-tone pair acoustic sensing signal such as for adaptive frequency hopping range gating (A)FHRG. An example of which is described in PCT/EP2017/073613. Each peak-to-trough shape is two tones mixed. The change is height of the peaks is due to non-idealities in a real phone speaker and mic, where the max output power drops with increasing frequency. In the figure, the X-axis is time, y-axis is amplitude. The direct path/static reflections with such a signal are maximal at the positive and negative peaks. During the troughs, the echoes may dominate.

If such a waveform in an adaptive frequency hopping range gating (A)FHRG is employed with dual tones, the amplitude of the tones can be ramped up and down within the time period of within the respective time slot. The ramp up and down time sequence (dual time) could be 100 Hz apart. This means that the direct path on the receive not only can be seen (detected), but the reflections in troughs (as almost "quiet" at this time) can also be discerned/discriminated. The main direct path is static reflection. Well-designed transmit/receive transducers have only a small amount of "bleed through" (i.e., a strong direct path from speaker to microphone) directly from the loudspeaker to the microphone. This may tend to be larger on a smart phone or smart speaker where the loudspeaker and microphone are co-located. When the received signal is demodulated, the direct path causes a significant DC level. The direct path component (i.e., a well-known delay path—such as related to a fixed distance between speaker(s) and mic(s) can also be taken advantage of, in order to estimate any fixed or variable delays in the transmit/receive signal path—e.g., where there is variable latency, clock drift, stop/start behavior and so forth, which may have an undesirable effect on the relationship between transmit and receive signals. In the case where there is a small or no direct path, the use of coding and/or pilot tones can be used on the transmit signal in order to recover transmit/receive signal timing information.

Dual Tone FMCW (Also Referenced Herein as Dual Ramp Technology)

In contrast to such a dual (multi-tone) pair in relation to (A)FHRG as just described, a processing device in some versions of the present technology may instead be implemented with a dual tone FMCW sensing signal such as for low frequency ultrasonic sensing. In this regard, there are different ways that the acoustic sensing signal can be created when implementing a low frequency ultrasonic sensing system with an FMCW type of approach. This may involve differences in waveform shape in the frequency domain (e.g., triangular (symmetric or asymmetric), ramp, sinusoidal etc.), period (duration of the "chirp" in time), and bandwidth (frequency covered by the "chirp"—e.g., 19-21 kHz). It is also possible to use two or more simultaneous tones in an FMCW configuration.

The choice of number of samples defines a possible output demodulated sampling rate (e.g., a 512 samples at a sampling rate of 48 kHz equates to 93.75 Hz (48,000/512), whereas a 4096 sample duration sweep time equates to 11.72 Hz (48,000/4096). If a triangular waveform is used with a 1500 sample uptime, and 1500 sample downtime, then the output sampling rate is 16 Hz (48,000/3000). For this type of system, synchronization can be performed by multiplying the signal by a reference template, for example.

Regarding the choice of the output sampling rate, empirical testing has shown that operating in the approximate region of 8 to 16 Hz is preferable, as it broadly avoids 1/f noise (low frequency effects due to air movement, potentially strong fading, and/or room modes) as well as staying out of the reverberation region seen at higher demodulated sampling rates (i.e., we have allowed time for the energy in any one frequency of sensing waveform "chirp" to fade before the next similar component in next "chirp"). Presented another way, if you make bins too wide, changes in airflow and temperature (e.g., opening door and heat goes in or out of room) means any block you are looking at could contain an unwanted baseline drift which can look like breathing. Practically, this means that a wave is seen to move across the band (across range bins) as the air moves. This is distinct from more localized effects from a desk or pedestal fan, or an air conditioning or other HVAC system. Effectively, if the blocks are made too wide, the system begins to "look like" a CW system. On the other hand, one can get reverb if the system works at too high a refresh rate (i.e., too short a ramp).

Figure 7A:
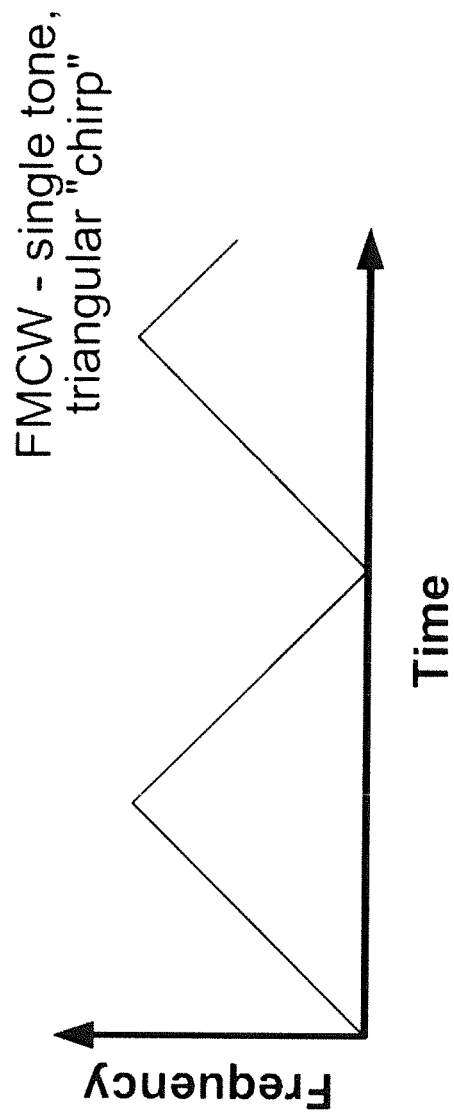
FIG. 7A shows frequency characteristics of a single tone chirp such as for frequency modulated continuous wave sensing (FMCW).

For a triangular FMCW waveform with one "tone" (i.e., that is swept up and down in frequency) as illustrated in FIG. 7A, a system can process, for example, just the up-sweep, or just the down-sweep, or indeed both may be processed for distance detection. The phase-continuous triangular form for one tone is highly desirable as it minimizes or removes any audible artefact in the played sound created by a phase discontinuity. A ramp variant of this can give rise to a very unpleasant and audible buzzing sound, as the speaker(s) is/are asked to jump from playing a certain amplitude sound at a frequency to a much lower (or much higher) frequency at a similar amplitude within the space of a sample; the mechanical change in the speaker can give rise to a click, and the frequent repetition of the chirp means that the user hears a buzz (many closely spaced clicks).

Thus, in some versions of the present technology, the acoustic sensing signal as a FMCW may be implemented with special dual "tones" with a ramp waveform (e.g. which consists of an up-sweep or a down-sweep only)—so that there is a sharp change in frequency from the end of one ramp (frequency ramp up and down) to the next (frequency ramp up and down) without audible artefact. Such a dual "tone" frequency modulated waveform showing its frequency characteristics relative to time, where at least two changing frequency ramps overlap during a period of time and these frequency ramps each may have a different frequency relative to the other(s) at any instant of time in the period such as for the duration of the ramping or for a portion, is illustrated in relation to the dashed line versus the solid line in FIG. 7B. This can ultimately simplify the data processing in the system, and also remove the potentially high amplitude transition at each point of a triangular waveform. Sharp and repetitive transitions can sometimes trigger strange behavior in a system's low level DSP/CODEC/firmware).

An important consideration to implemented such a dual tone signal is that the resulting shape is made (shaped) such that the speaker/system does not need to make a sharp transition, and it has zero points. This can reduce the need for filtering that would otherwise be implemented to render the signal inaudible. For example, high pass or band pass filtering may be avoided while still permitting the signal to operate as an inaudible sensing signal. The presence of zeros in the waveform eases signal processing because that the zeros simplifies synchronization of the transmit and the receive of such a signal (e.g., for demodulation). A consequence of the dual tones is that it offers an element of fading robustness as more than one tone is used—and fading can vary with the frequency used, as well as phase or frequency (e.g., one might use a 100 Hz offset between the FMCW tones in a dual tone system).

Figure 7B:
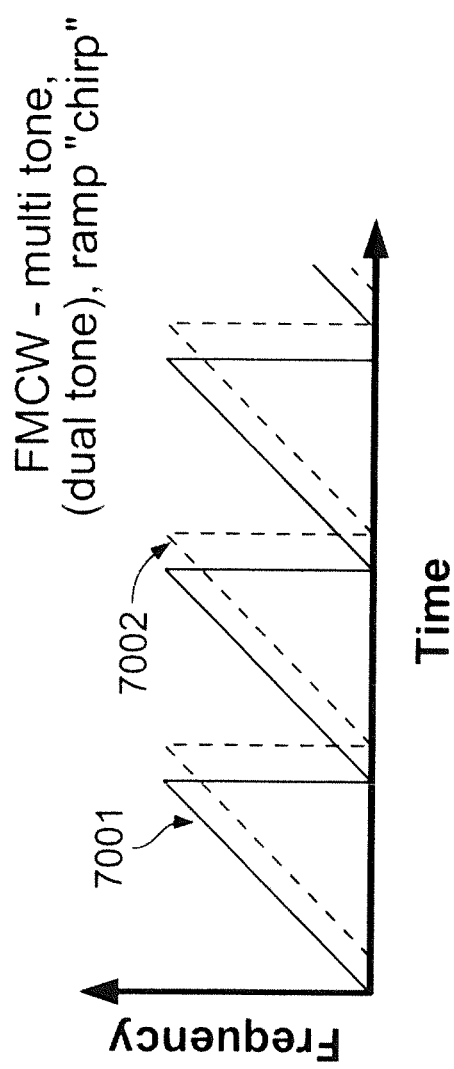
FIG. 7B shows frequency characteristics of a dual tone chirp such as for frequency modulated continuous wave sensing (FMCW).

FIGS. 7A and 7B show a frequency domain comparison of FMCW single tone (FIG. 7A) and dual tone (FIG. 7B) implementations. A single tone (FIG. 7A) may preferentially include a downsweep (a reduction in produced frequency over time) to ensure inaudibility. However, a downsweep may be omitted but may cause some audibility. A dual tone (FIG. 7B) can help avoid the need for such a downsweep, as the time domain representation is shaped such as to be inaudible. FIG. 7B shows the first tone 7001 and the optional second tone 7002 overlap. The figure does not show the received echo (i.e., the reflection signal). Thus, tones form a first sawtooth frequency change overlapped with a second sawtooth frequency change in a repeated waveform. They are continuous such that they may be repeated during a sensing period.

Figure 8A:
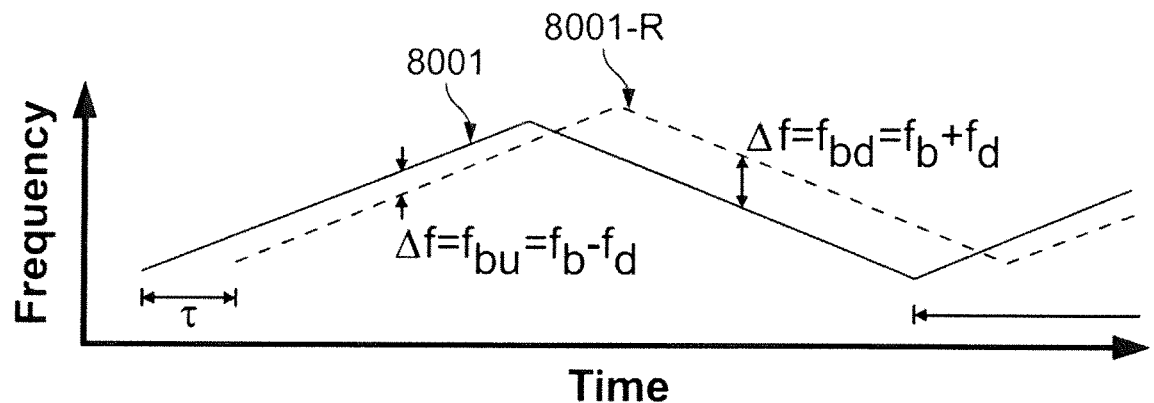
FIGS. 8A, 8B and 8C illustrate various signal characteristics of a triangular single tone such as for a FMCW system.
Figure 8B:
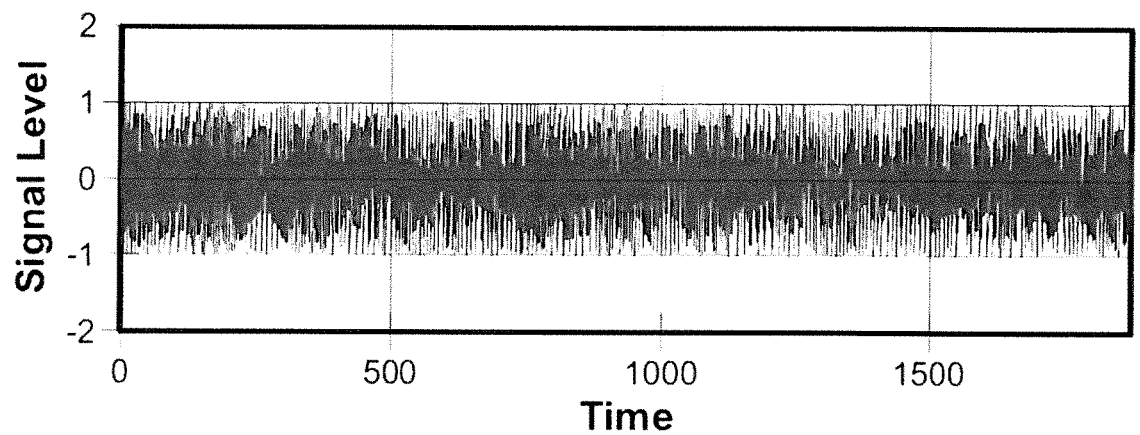
Figure 8C:
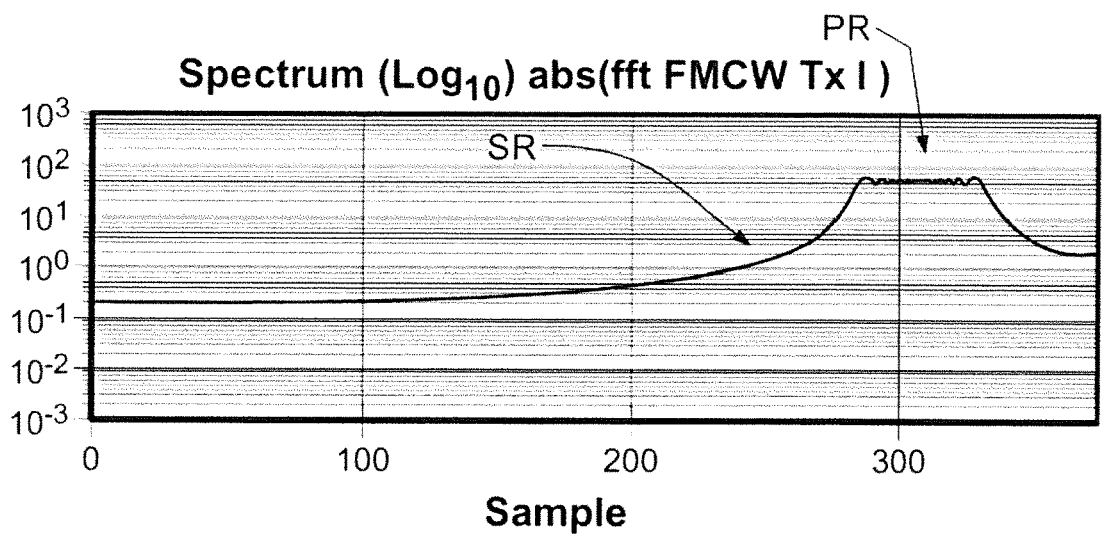
Figure 9A:
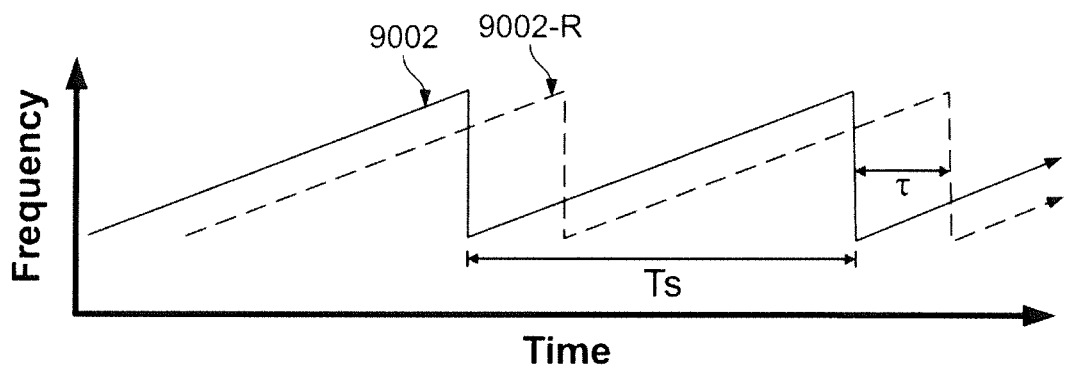
FIGS. 9A, 9B and 9C illustrate various signal characteristics of a triangular dual tone such as for a FMCW system.
Figure 9B:
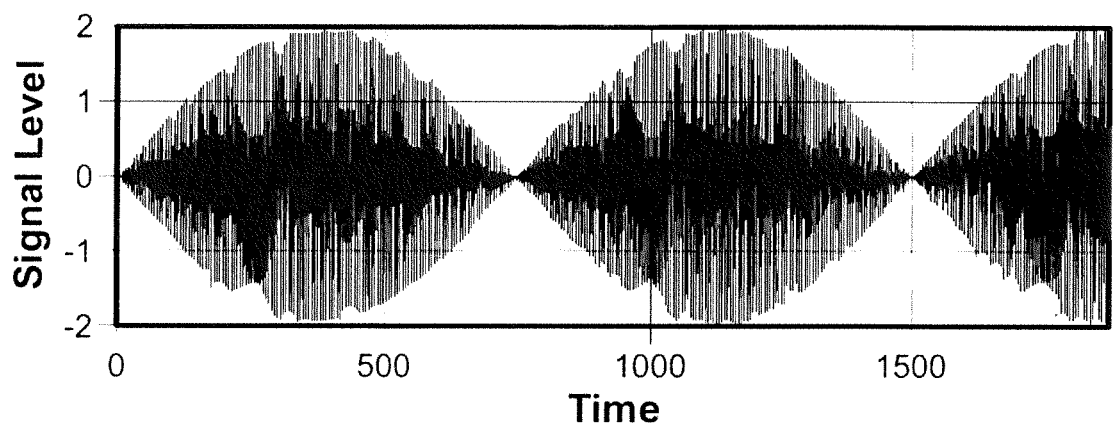
Figure 9C:
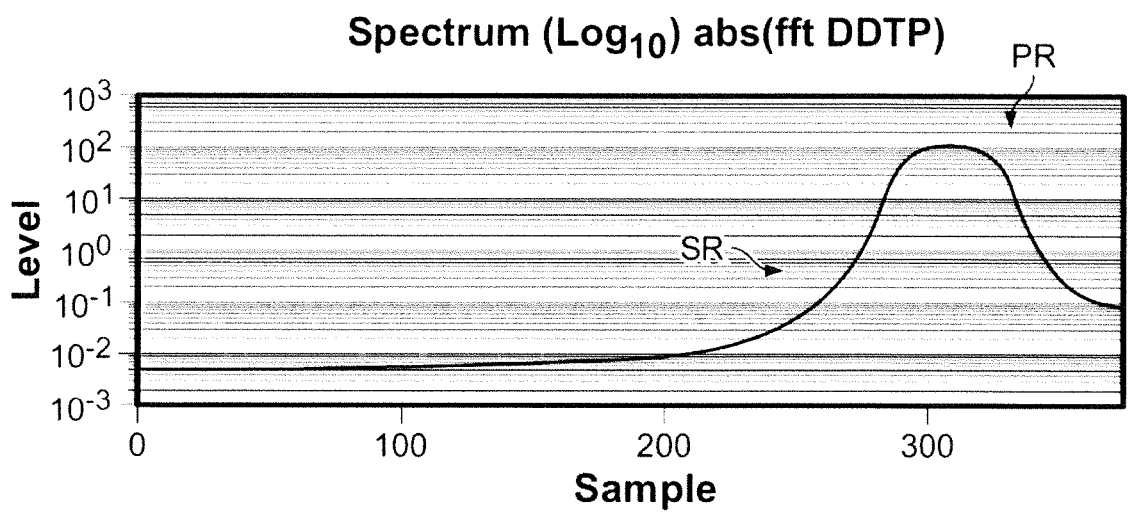

Performance of the FMCW single tone of FIG. 7A and the FMCW dual tone of FIG. 7B may be considered in reference to FIGS. 8 and 9. FIGS. 8A, 8B and 8C show signal characteristics of the FMCW single tone example of FIG. 7A. FIGS. 9A, 9B and 9C show the signal characteristics of the FMCW dual tone example of FIG. 7B.

FIG. 8A shows the transmitted (Tx) signal 8001, and the received (Rx) reflection 8001-R (echo) operating as a triangular single tone FMCW operating in an acoustic sensing system. FIG. 8B shows the time domain waveform. FIG. 8C shows the spectral content of the signal. As evident, there is still content at lower frequencies (outside the peak area relating the bandwidth of the FMCW signal). Such lower frequencies may thus be in an audible frequency range and thereby resulting in an undesirable performance characteristic.

FIG. 9A depicts a dual tone ramp FMCW signal in signal graph 9002. Signal graph 9002 represents both tones, and signal graph 9002-R represents the received echo of the two tones/multi-tone. FIG. 9B shows a cosine-like functional shape of the dual tone, with the zero points (resultant zero crossings). FIG. 9C shows a much smoother peak and lower power amplitude at lower frequencies. The slope region SR of FIG. 9C, when compared to the slope region SR of FIG. 8C, illustrates a sharper decline in power (dB) of the dual tone ramp FMCW in/to the lower frequencies. The sharper roll-off from the range of the high (substantially inaudible, utilised for sensing) frequencies and into the lower (audible, not typically utilised for sensing) frequencies, is a desirable acoustic sensing property as it is less obtrusive for the user. The power at lower frequencies (outside the peak area relating to the bandwidth of the FMCW signal) can be 40 dB less than that in the case of the single tone FMCW triangular form illustrated in FIG. 8C. As illustrated in FIG. 9C, the upper smooth peak region PR of FIG. 9C when compared to the multi-edged peak region PR of FIG. 8C, indicates that the dual tone ramp FMCW signal can have better acoustic sensing properties and is less demanding on the speakers. Such a multiple tone FMCW or dual tone FMCW system (for example running on a Linux based single board computer) can provide sensing such that it is possible to identify multiple persons within the sensing range of 4 m or more. It can also detect heart rate for example at 1.5 meters from the processing device, and respiration rate(s) at out to approximately 4 meters or more. An exemplar system could use two tones at 18,000 Hz and 18,011.72 Hz, which could ramp to, for example, 19,172 Hz and 19183.72 Hz respectively.

For this ramp of 1,172 Hz, we can consider using, for example, an FFT of size 4096 points, with bin width of 48,000 Hz/4096=11.72. For speed of sound as 340 m/s, we note: 340 ms/s/11.72/2 (for out and back)=14.5 m over 100 bins or 14.5 cm for each bin. Each "bin" can detect up to one person (per bin) for example (but in practice persons would be separated by more than this.) As part of a synchronization process, the signal could be squared, for example, to avoid a more computationally expensive correlation operation, where the signal is multiplied by a reference template. Independent of the FFT size used, the maximum range resolution is speed-of-sound/(Bandwidth*2)=340/(1172*2) =14.5 cm. However, a synchronization process may optionally be provided that includes cross-correlating a sensed reflected signal with a sensed direct path signal. A synchronization process may optionally include multiplying a reference template with at least a portion of the sensed reflected sound signal.

Figure 10:
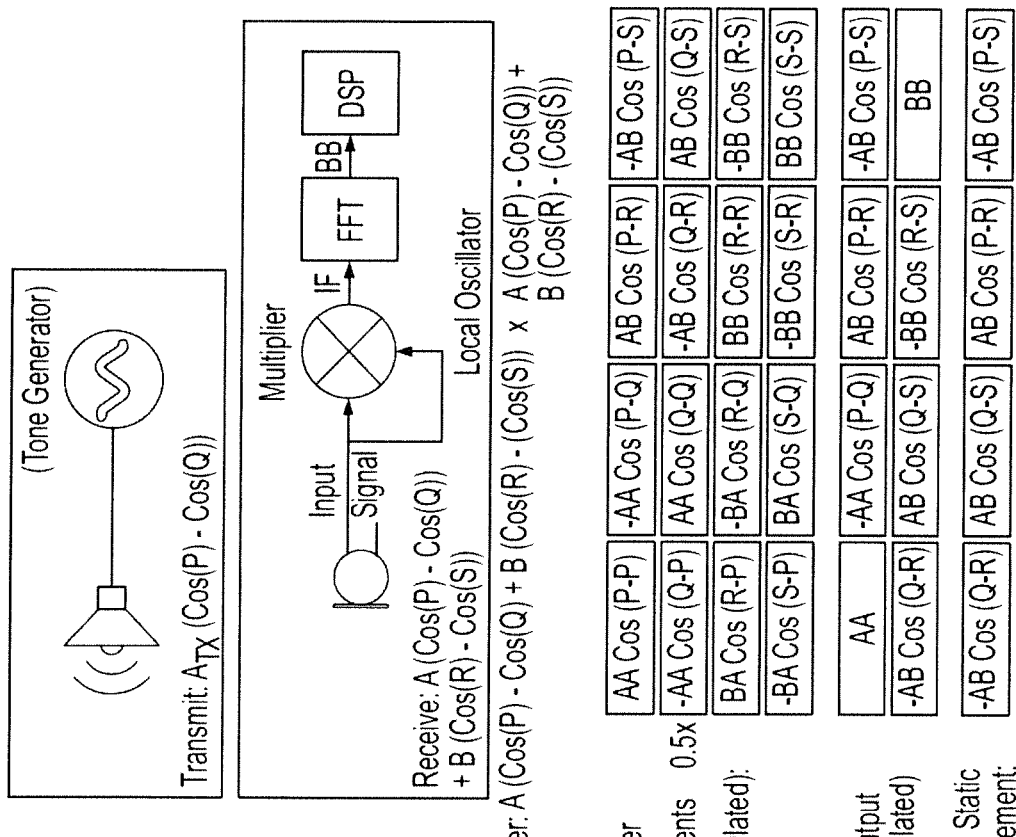
FIG. 10 illustrates example demodulation for a dual tone FMCW that may be implemented for a sensing system of the present technology.
Figure 10:
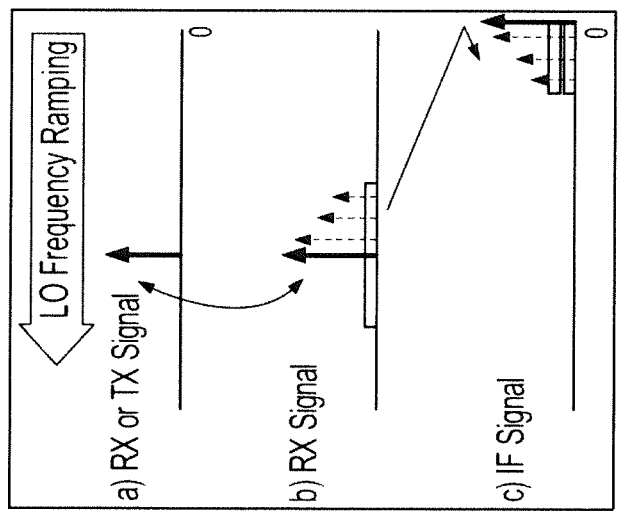

FIG. 10 illustrates an example of "self-mixing" demodulation of a dual tone FMCW ramp by multiplying the signal by itself (squaring). In this regard, demodulation may be carried out by multiplying the received echo signal with a signal representative of the generated transmit signal (e.g., a signal from an oscillator) to produce a signal reflecting distance or motion in the range of the speaker or processing device 100, 102. The processing produces a "beat frequency" signal which is sometimes referred to as an "intermediate" frequency (IF) signal. With FMCW, when the receive Rx signal is demodulated, such as by a local oscillator or by itself as described in more detail herein, and low pass filtered, it may produce an unusual "intermediate" signal that is not yet considered to be baseband (BB). The IF signal may be processed, such as by application of fast Fourier transform processing (FFT), to become baseband (BB).

As illustrated in FIG. 10, the demodulation is conducted with the receive (reflected sound signal) Rx signal only. That is mathematically possible because the Rx signal contains a large percentage of a signal representative of the transmit (Tx) signal (e.g., the produced sound which may, in part, travel a direct path from the speaker to the microphone and be sensed with the reflected sound) in it. The device can multiply the receive signal Rx by itself (such as by just squaring it because demodulation can be considered a multiply operation). This can be followed by a filtering process (e.g. lowpass).

Although FIG. 10 illustrates self-mixing, several different approaches may be implemented to derive a motion signal with the reflected signal, and the sensing signal (i.e., Tx or sound signal). In one such version, a local oscillator LO (which may also produce the sound signal) can effectively produce a copy of the Tx signal for demodulation. The actually produced Tx signal might be slightly different than the internal signal from the oscillator because of delay or distortion. Demodulation can then be conducted by multiplication of the signal from the local oscillator LO(Tx)*Rx which can also be followed by filtering (e.g., lowpass).

In another version, two local oscillators may be implemented to generate two LO signals. For example, a Sin and Cosine copy of the LO signal may be implemented to provide for quadrature demodulation of the receive signal. Typically, only one signal from an oscillator (either Sin or Cosine) is transmitted. The exact Tx signal will be somewhat different from the signal from the local oscillator LO due to delay or distortion. In this version, demodulation may be conducted (a) RX*LO(Sin) and (b) RX*LO(Cos), which may be followed in each case by filtering (e.g., lowpass) to produce both I and Q demodulation components.

Figure 11:
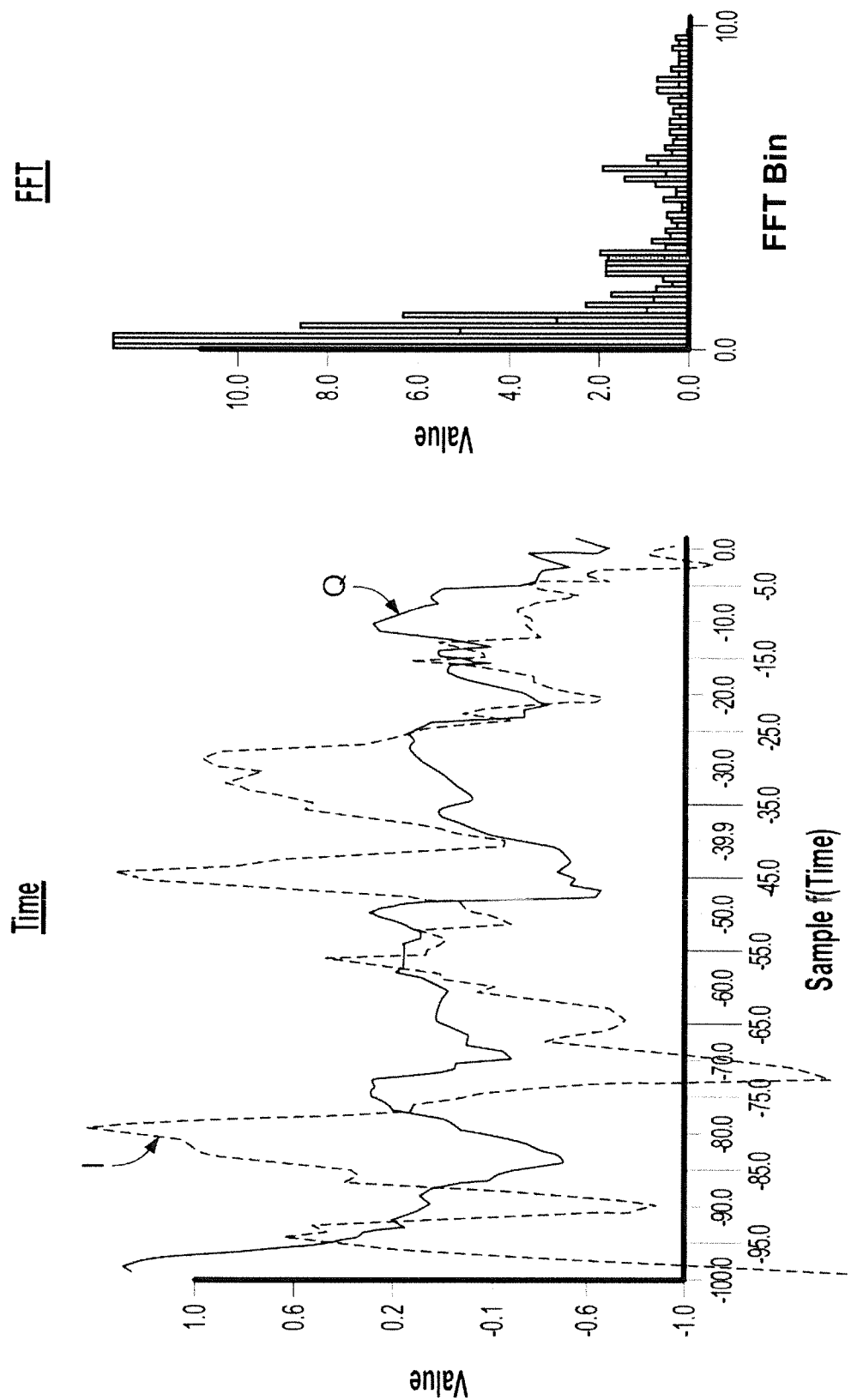
FIG. 11 illustrates an example signals produced with a dual tone FMCW system.

FIG. 11 includes several graphs showing output of the demodulation performed with generated in-phase and quadrature phase signals. The left panel shows demodulated I/Q traces (an I (inphase) and Q (quadrature) baseband signal). The right panel of the figure shows a spectral estimate of the signals (e.g., a complex fast Fourier transform (FFT)) which shows from left the DC/VLF components, red/blue vertical lines around the Biomotion signal of a first person in front of the sensor, and the other peak to the right showing the signature of a second person in the range (but further away) from the sensor. Note that no reflections are seen at the rightmost of the FFT, as the two persons closer to the sensor are shadowing the wall's reflection.

Figure 12:
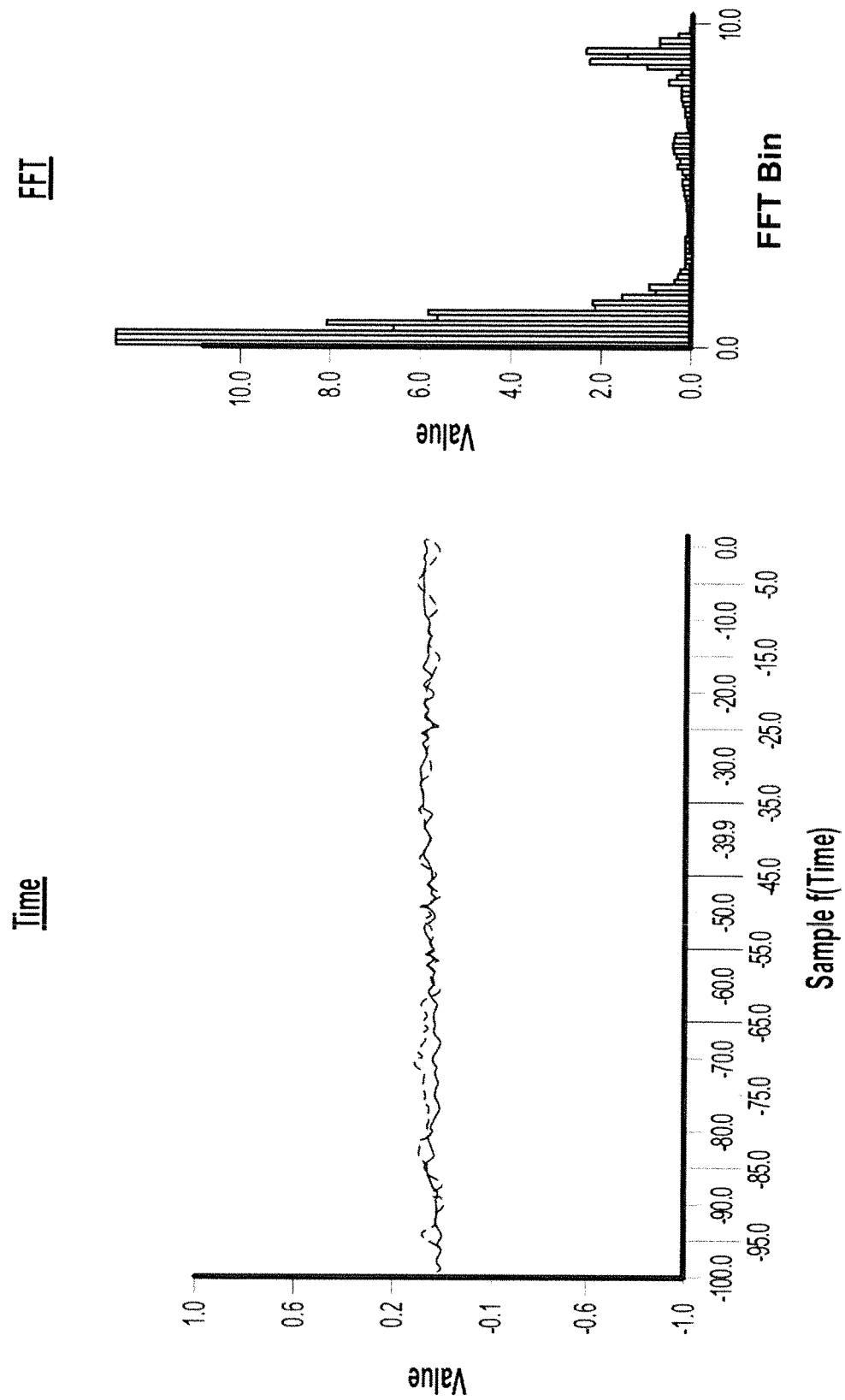
FIG. 12 illustrates additional signals produced with a dual tone FMCW system.

As illustrated in FIG. 12, there is no detected biomotion within 4 meters of the low frequency ultrasonic sensor. This is evident from the physiological movement signal in the I and Q traces that vary approximately at the zero amplitude line. On the left side of the FFT graph, the DC and VLF components are shown. To the right of the FFT graph, a peak due to reflections from a wall in the room is illustrated.

Figure 13:
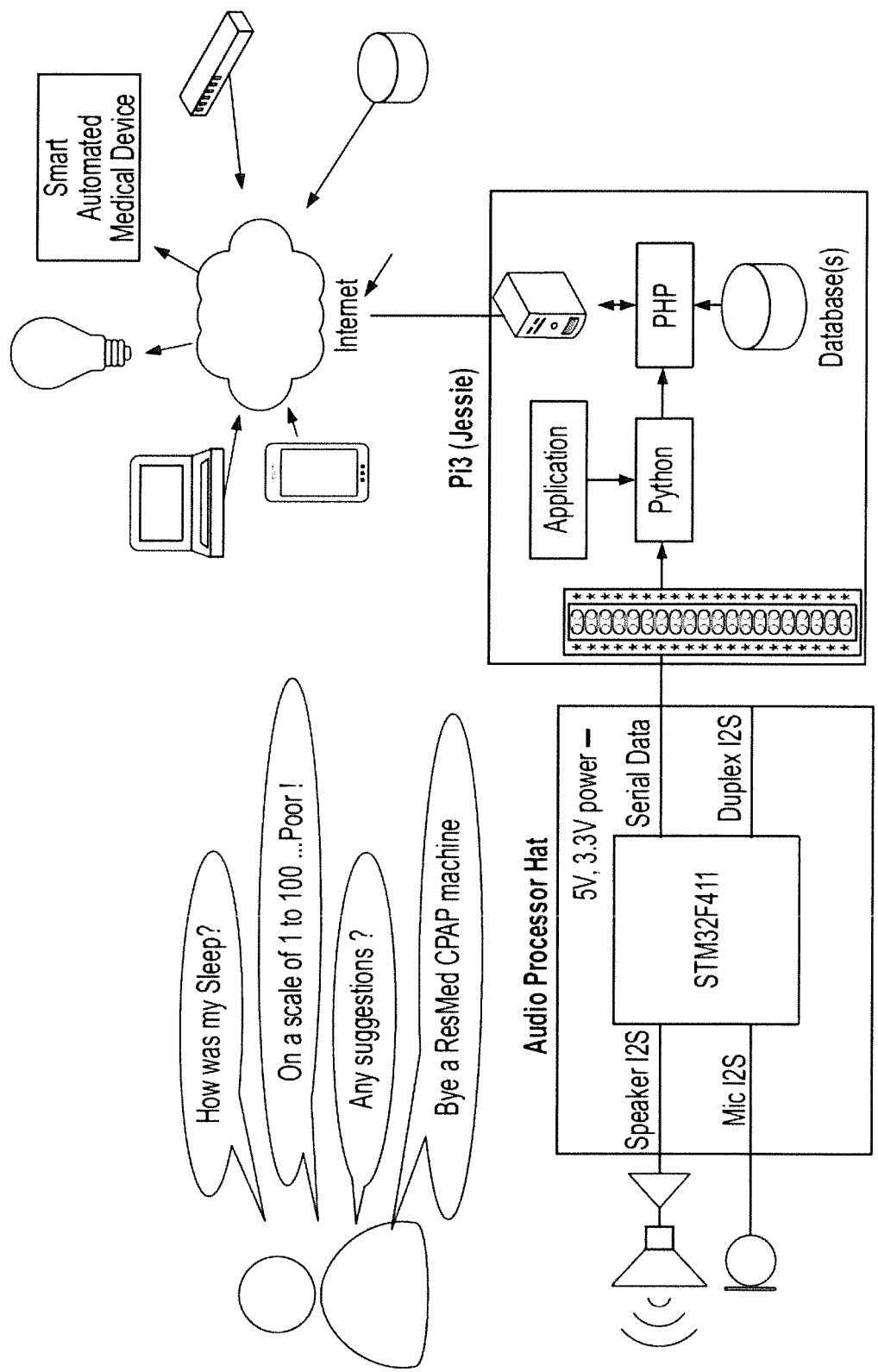
FIG. 13 illustrates example operations of a voice enabled sleep improvement system such as one using low frequency ultrasonic biomotion sensing with signal generation and processing techniques described herein.

Exemplar system architecture of a voice enabled sleep improvement system using low frequency ultrasonic Biomotion sensing is illustrated in FIG. 13. The system may be implemented with the sensing techniques described herein (e.g., multi-tone FMCW acoustic sensing). A user can talk to a voice activated speaker that was previously activated to monitor the user's sleep. For example, a verbal instruction can query the smart speaker to produce an audible report of determined sleep score, respiratory (SDB) events or sleep statistics. Based on the report, the processing of the system can also produce audible advice as to improving sleep, such as by suggesting a therapy device to assist with sleep.

Figure 14:
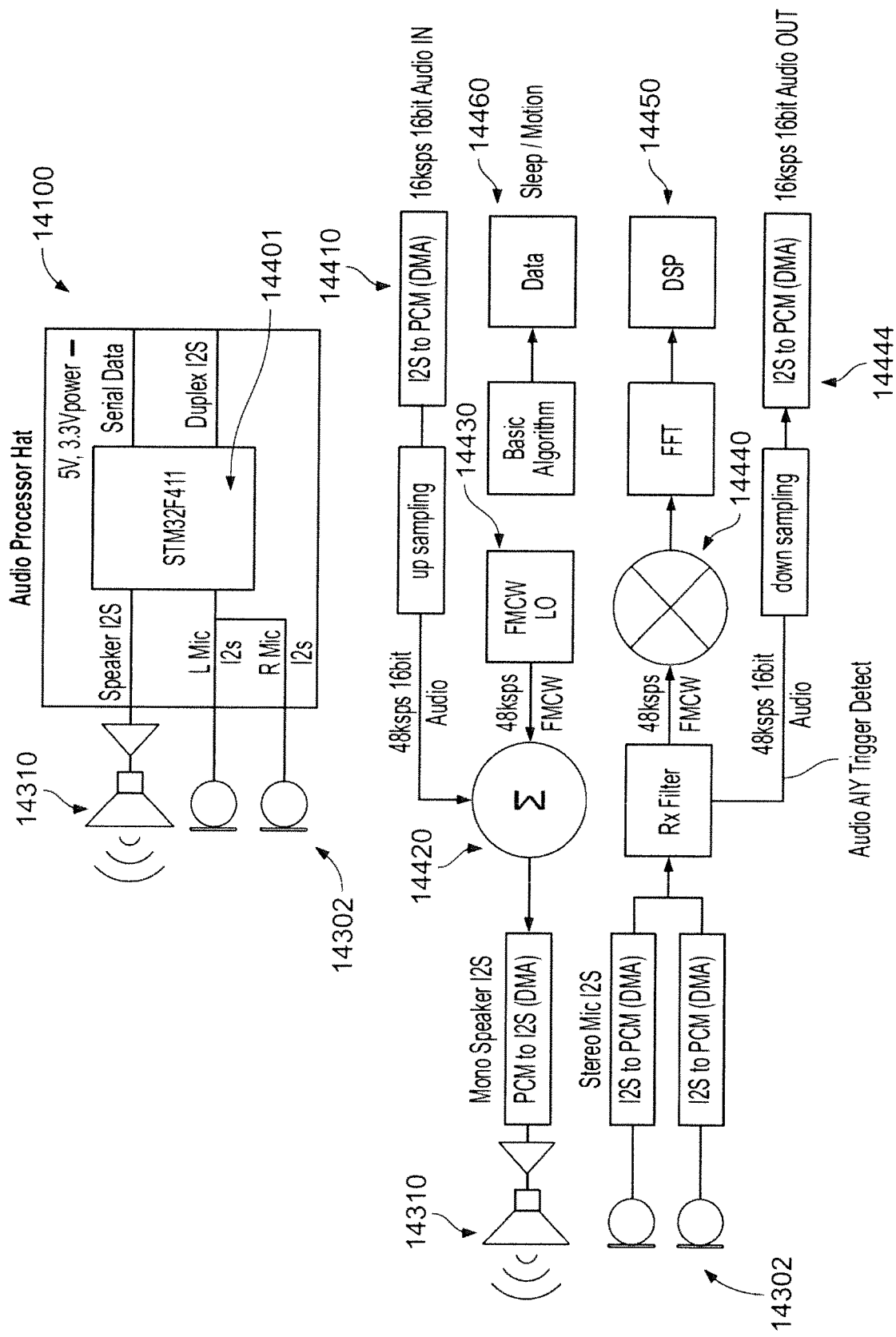
FIG. 14 illustrates example audio processing modules or blocks such as for the processing described herein.

System processing for detection of motion in a vicinity of a speaker-enabled processing device that is enabled with the low frequency ultrasonic sensing of the present technology may be considered in relation to the modules illustrated in FIG. 14. The processing device 14102 includes a speaker 14310 and, optionally, dual microphones 14302 as well as a microcontroller 14401 with one or more programmable processors. The modules may be programmed into a memory of the microcontroller. In this regard, an audio sample or audio content may be upsampled by optional upsampling processing module at 14410 and may be provided to a summer module 14420, such as if optional audio content is produced by the speaker simultaneously with the sensing signal. In this regard, the summer module 14420 optionally combines the audio content with the FMCW signal in the desired frequency ranges from the FMCW process module 14430 that produces the FMCW signal (e.g., the dual tone FMCW signal in the desired low ultrasonic frequency ranges). The summed FMCW signal may then be processed such as by a converter module for output by the speaker 14310. The FMCW signal is also applied to a demodulator such as a multiplier module 14440 where the FMCW signal is processed (e.g., mixed/multiplied) with the received echo signal observed at the microphones 14302. Prior to such mixing, the received echo signal may be filtered, such as adaptively, as previously mentioned herein to remove undesired frequencies outside the frequency spectrum of interest. An audio output processing module(s) 14444 may optionally down sample the filtered output and/or convert the signal to produce an audio signal. The demodulated signal output from the multiplier module 1440 may then be further processed, such as by post-processing module 14450. For example, it may be processed by frequency processing (e.g., FFT) and digital signal processing to improve the raw motion signal detected or otherwise separate motions by frequency range so as to isolate (a) respiration motion or movement, (b) cardiac motion or movement, and gross motion or movement, such as gross body motion or gross body movement, for example. The physiological movement signal(s) may then be recorded or otherwise processed, e.g., digitally, by characteristics processing at 14460 to characterize various motions of the signal so as to detect various informational output as previously mentioned (sleep, sleep stage, motion, respiration events, etc.).

In relation to detection of gross movement or gross body motion, such movement may include any of arm movement, head movement, torso movement, limb movement, and/or whole-body movement, etc. Methodologies for such detections from transmitted and reflected signals for motion detection, which may be applied to SONAR sound-type motion detection, may be considered and applied, for example, as described in International Patent Application Nos. PCT/EP2016/058806 and/or PCT/EP2016/080267, the entire disclosures of which are incorporated herein by reference. By the nature of it, such RF or SONAR technology may be seeing all body movement at once, or at least most of it—and it may depend on where exactly the "beam" is directed. For example, is it illuminating primarily the head and chest, or the whole body etc. Leg movement, such as when it is periodic, may primarily distinguished as a motion based on frequency of movement, and optionally by performing different automated gain control (AGC) operations. Respiration detection is most effective when there is less gross body movement, to isolate the characteristic frequencies and signal shape of a breathing waveform (either normal, COPD or CHF changes to rate over time and inspiration/expiration ratio, SDB events, longer term SDB modulation etc.)

When motion is associated with a person in bed, the largest amplitude signals may be associated with a full body movement, such as a roll. A hand or leg movement may be faster (e.g., velocity from I/Q signal) but lower relative amplitude. Thus, different components, and or sequences of components, of such a movement by analysis of a motion signal may be considered in the identification such as whether it starts with gross movement and acceleration, velocity of arm movement, then stops, etc. This identification may be more targeted for different motion gestures.

Figure 15:
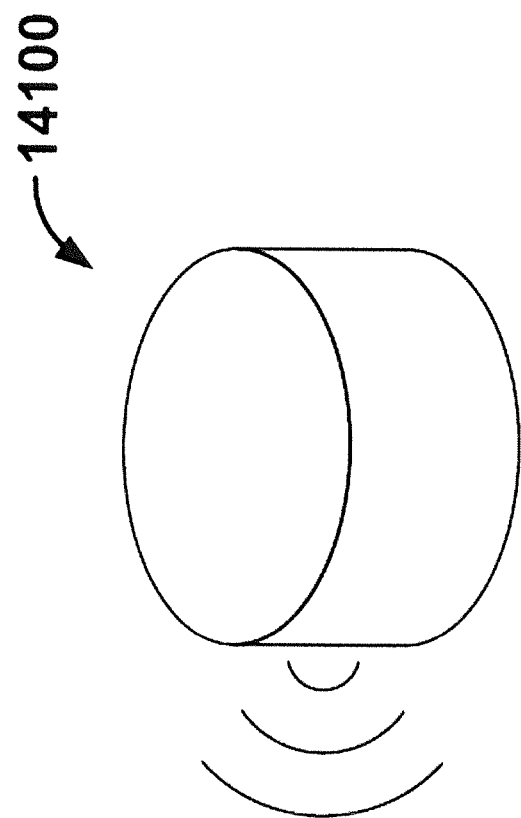
FIG. 15 illustrates an example processing device implemented with the processing techniques described in more detail herein such as for biomotion sensing or other motion sensing in a sensing field of the processing device.
Figure 15:
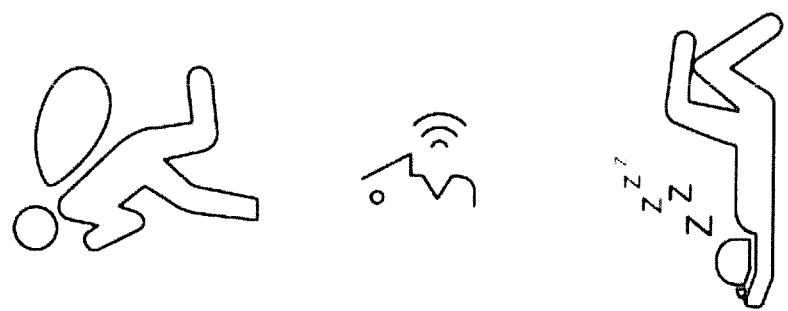

As illustrated in FIG. 15, such a processing device 14100 may be small and un-obtrusive. It can run applications for voice assistance with biomotion sensing to detect one or more persons speaking (awake), detect sleepiness and sleep stage, etc. and any unauthorized parties in the sensing field.

As previously mentioned, the processing device may be implemented in a respiratory therapy device 5000 (e.g., PAP) such as illustrated in FIG. 5. In this regard, the illustrated microphone and speaker of FIG. 5 are implemented to produce low frequency ultrasonic sensing signals (enabled using transducers such as a speaker and microphone) built into the respiratory device but may be directed to sensing externally of the patient circuit. During the time of therapy, the respiratory parameters used for detecting apneas and calculating AHI, may be measured by the sensors of the flow generator itself so as to detect conditions within the patient circuit. The ultrasonic sensing may be activated typically used when a mask (patient interface 3000) and the flow generator (e.g., respiratory therapy device 5000) are not in use. As show in FIG. 5, a partner may be present and may, optionally, be monitored by another processing device 100.

Figure 16:
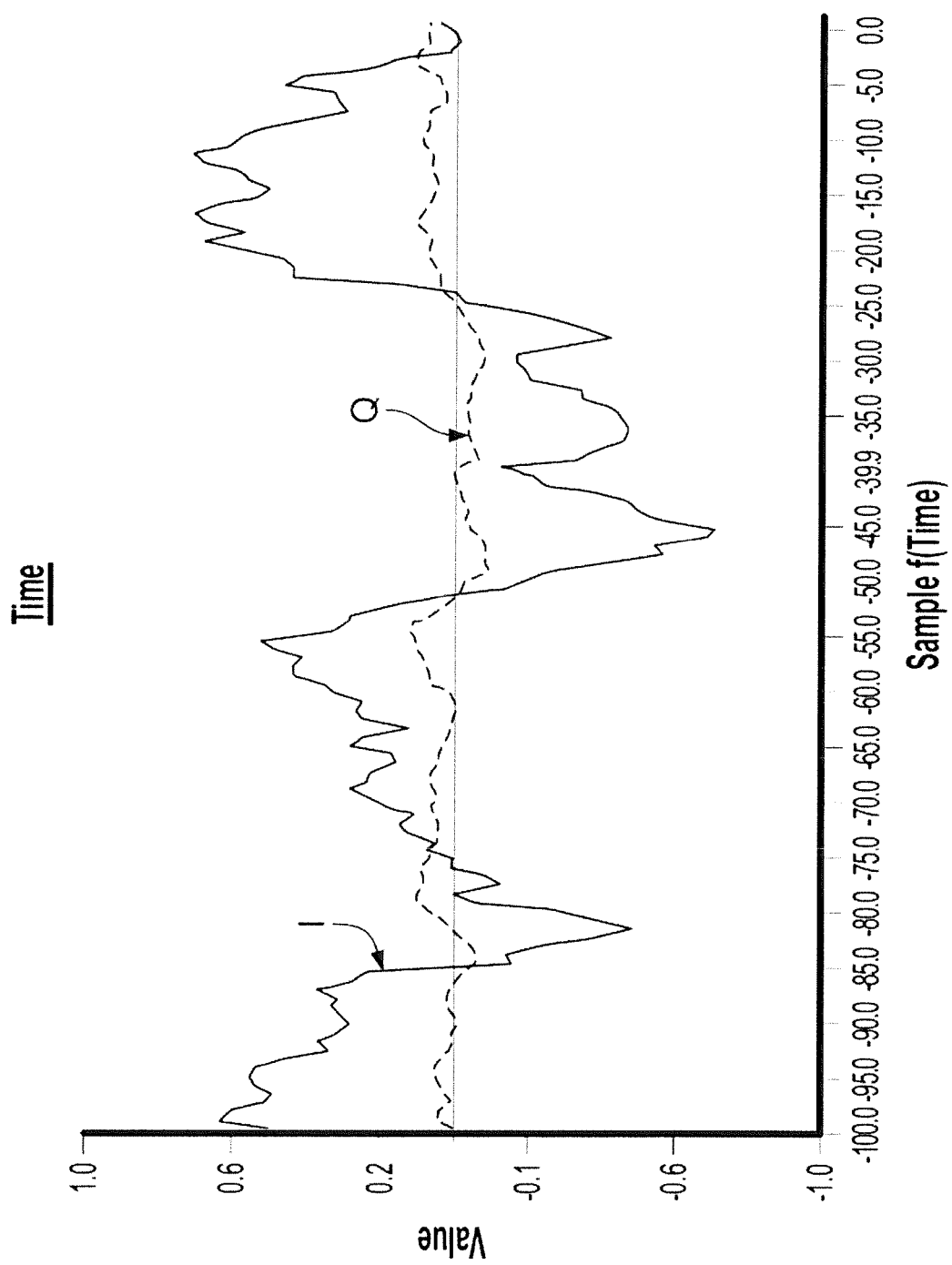
FIG. 16 shows in-phase (I) and quadrature phase (Q) baseband signals produced with the sensing techniques described herein where the signals show gross body movement, respiratory movement, and cardiac movement in a raw motion signals.
Figure 17:
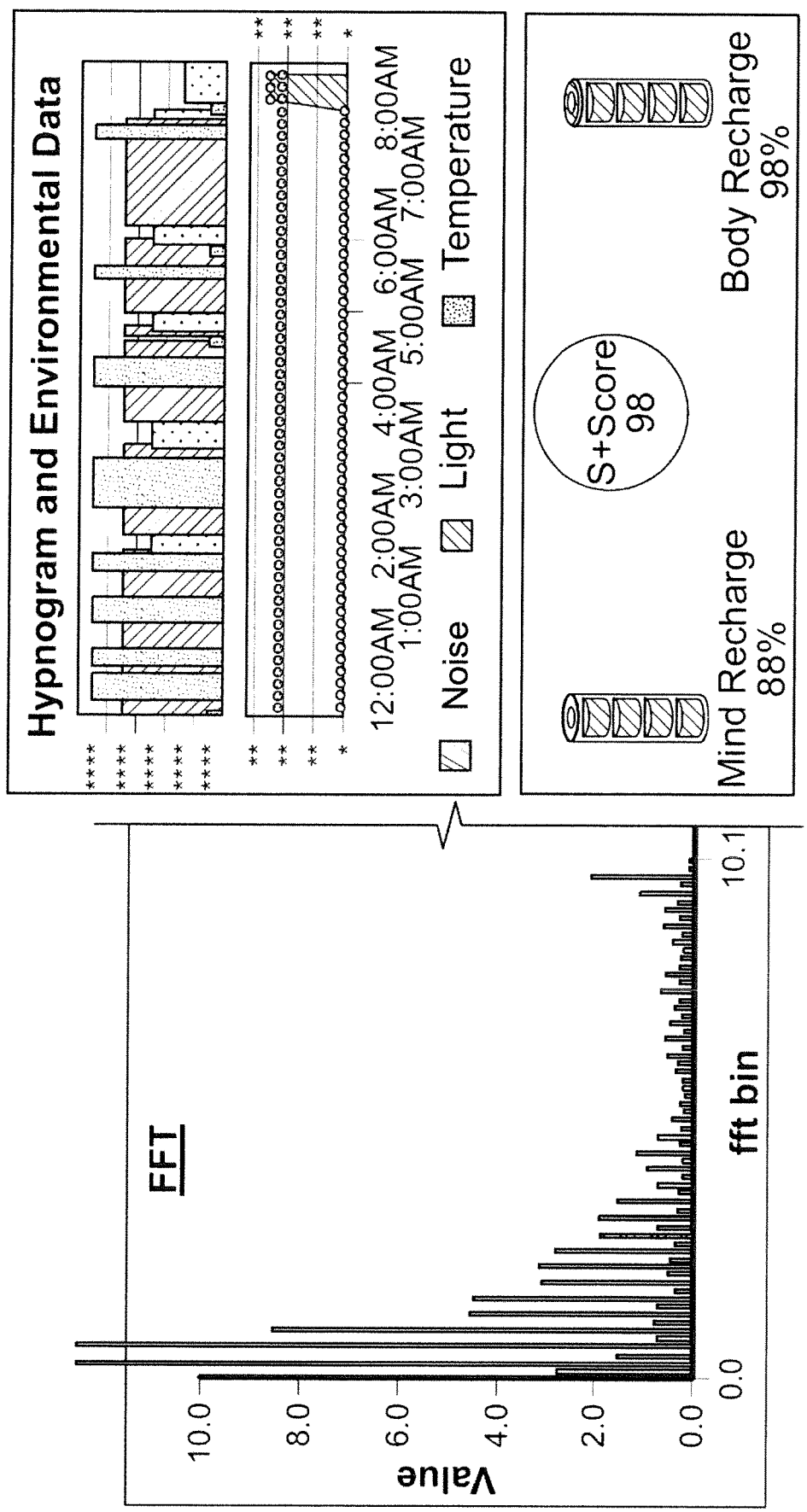
FIG. 17 illustrates example output (e.g., sleep stage data) produced by processing of the motion characteristics of the signals for FIG. 16.

As illustrated in FIGS. 16 and 17 different output may be detected and generated by the processing device 100 in relation to motion and its distance from the processing device 100. In FIG. 16, an I (in-phase) and Q (quadrature) baseband signal extracted from a specific range bin (e.g., distance from the processing device). This contains gross body movement, respiratory movement, and cardiac movement. In FIG. 17, the left panel shows a complex spectral estimate with all available range "bins". The selected bin in blue yields the I/Q baseband traces shown in FIG. 16. The bottom right panel is a depiction of a possible sleep score, heart rate and breathing trace, and sleep stages or any other information detectable from the physiological movement signal(s). The sleep score is calculated based on the events shown in the hypnogram of the top right panel of FIG. 17.

Sensing—Mixing (Coexistence) of Acoustic Sensing with Other Audio Playback by the System (Music, Speech, Snoring Etc.)

Some versions of the present technology may be implemented when the processing device 100 may be using its speaker and/or microphone for other purposes, in addition to the ultrasonic sensing described herein. Additional processes may be implemented to permit such simultaneous functioning. For example, the transmit bitstream (acoustic sensing signal) may be digitally mixed with any other audio content (audible) that is being played by the speaker as previously mentioned for simultaneous audio content production and ultrasonic sensing. Several approaches can be used to carry out such audible audio content and ultrasonic processing. One approach requires that the other audio content (which could be mono, stereo or many more channels—such as in many channel surround sound systems) is preprocessed to remove any spectral content that would overlap with the sensing waveform. For example, a music sequence might contain components of over 18 kHz which would overlap with, for example, an 18 to 20 kHz sensing signal. In this case, the music components near 18 kHz can be low pass filtered out. A second option is to adaptively filter the music so as to remove frequency components for the short periods of time during overlapping sensing (direct path and echo), and allow the unfiltered music otherwise; this approach is designed to retain the fidelity of the music. A third option may simply make no changes whatsoever to the music source.

It should be noted that where delays are deliberately added to audio sources on certain channels (e.g., Dolby Pro Logic, Digital, Atmos, DTS etc. or indeed virtualized spatializer functions), any such in-band signals are also accordingly processed, and the sensing waveform will either not be delayed or the delay would be allowed for, when processing the echoes).

Sensing—Coexistence with Voice Assistants

It should be noted that certain realizations of ultrasonic sensing waveforms (e.g., triangular FMCW), may have an unintended and unwanted impact on certain voice assistants that are performing voice recognition services, such as Google Home, as they have spectral content within the audible band. Such potential cross talk can be avoided by using a dual ramp tone pair, or pre-filtering (high pass or band pass filtering the triangular chirp) the sensing waveform, or adapting the voice recognition signal processing to be robust to the ultrasonic sensing signal components.

Consider an FMCW ramp signal y as follows:

$$y = [A \cos(2pi(f_1 + f_2 t)t + phi]_0^T$$

This ramp from frequency f_1 to frequency f_2 in a time period T. This has sub harmonics as it is switched at a time period of T.

An analysis of this shows that it has out of band harmonics which appear at lower frequencies and so can be heard.

Now consider a specific dual ramp pair y as follows:

$$y = [A \cos(2pi(f_1 + f_2 t)t + phi]_0^T - [A \cos(2pi(f_1 + (1/T) + f_2 t)t + phi]_0^T$$

Thus, the sub-harmonics are cancelled (subtracted in the above), and the signal retained. The 1/T is very specific; by using (1/T), or indeed −(1/T), the effect of the switching at time period T is canceled out. Thus, the resulting signal is inaudible. It does this while being mathematically simple, which is an advantage as it is not computationally onerous on a device (e.g., a smart mobile phone device).

Because the dual tone switches at DC level ("0"), there is a natural point in the waveform chirp (a beginning and an end of the signal) to turn off, such as to avoid clicking (i.e., turn on and off in a way to avoid a loudspeaker making a big jump). The "0"'s also allow us to introduce a quiet period between each chirp, or indeed between groups of chirps, in order to mitigate reverberation—and/or to identify a specific transmitter (i.e., to overlay a sequence of on/off chirp times).

The lack of sub-harmonics is also an advantage as it removes a possible source of interference when considering two devices operating in a room at the same time. Thus, two different devices can use non-overlapping (in frequency) tone pairs—or indeed overlapping in frequency (but not in time—due to the addition of non-overlapping quiet periods) tone pairs. The latter can be an advantage where loudspeaker/microphone combinations have limited available inaudible bandwidth (i.e., their sensitivity rolls off severely over 19 or 20 kHz).

Even comparing a relatively inaudible triangular FMCW signal to a dual tone ramp, the latter has a very much smaller level of sub harmonics (approaching the noise floor on a real world smart device—e.g., near the quantization level).

Because a dual tone ramp can be ramped up or down (rather than triangular) and yet have no out of band components, there are no inter ramp bleed problems which can occur with a triangular ramp.

A standard ramp audio signal cannot be made inaudible without extensive filtering, which would potentially distort the phase and amplitude of the resulting waveform.

Sensing—Calibration/Room Mapping to Optimize Performance

The processing device may be configured with a set-up process. When the device is first set up (or periodically during operation) it can send out an acoustic probing sequence to map the room environment, the presence and/or number of people in the room etc. The process can be repeated if the device is subsequently moved, or the quality of the sensed signals is detected to have decreased. The system may also emit acoustic training sequences in order to check the capabilities of the speaker(s) and mic(s), and estimate equalization parameters; real world transducers may have some non-linearities in the ultrasound frequencies used by the system, as well as temperature and turn on characteristics (e.g., as a loud speaker may take several minutes to settle).

Sensing—Beam Forming for Localization

It is possible to implement dedicated beam forming or utilise existing beam forming functionality—i.e., where signal processing is employed to provide directional or spatial selectivity of signals sent to, or received from, an array of sensors. This is typically a "far field" problem where the wavefront is relatively flat for low frequency ultrasound (as opposed to medical imaging, which is "near field"). For a pure CW system, audio waves travel out from the speaker, leading to areas of maxima and minima. However, if multiple transducers are available, it becomes possible to control this radiation pattern to our advantage—an approach known as beam forming. On the receive side, multiple microphones can also be used. This allows the acoustic sensing to be preferentially steered (e.g., steering the emitted sound and/or the received sound waves where there are multiple speakers) in a direction, and swept across a region. For the case of a user in bed, the sensing can be steered towards the subject—or towards multiple subjects where there are, for example, two persons in the bed. Beam steering can be implemented on transmit or receive. As low cost ultrasonic transducers (microphone or speaker) can be quite directional (e.g., for a small transducer, where the wavelength is comparable to the size of the transducer), this can restrict the area in which they can be steered over.

Sensing—Demodulation and Down Conversion

The sensed signal is demodulated, such as with the multiplier (mixer) module 14440 shown in FIG. 14, to produce a baseband signal that may be further processed to detect whether there is "presence" in the sensing field—a disturbance in the demodulated signal that relates to a change in the echoes received, related to a characteristic motion of a person. Where there is a strong received "direct path" (high crosstalk from speaker to microphone, e.g., transmission through a solid versus through air and/or short distance from speaker to mic) signal, in addition to the received echo signal, multiplication of the resulting sum can be performed to demodulate. Otherwise, the received echo can be multiplied (mixed) with a portion of the originally transmit signal, which is extracted in an electronic, and not acoustic, form. In this specific example, the system is not multiplying the receive signal by the transmit signal to demodulate it (although it may other embodiments). Instead, the system may multiply the receive signal (which contains an attenuated version of the transmit signal, as well as the receive echo(es)) by itself as follows:

Transmit=$A_{TX}$(Cos(P)−Cos(Q))

Receive=$A$(Cos(P)−Cos(Q))+$B$(Cos(R)−Cos(S))

Self-mixer=[$A$(Cos(P)−Cos(Q))+$B$(Cos(R)−Cos(S))]× [$A$(Cos(P)−Cos(Q))+$B$(Cos(R)−Cos(S))] i.e., receive×receive Self-Mixer components (Demodulated) after low pass filtering:

| 0.5x | AA Cos (P-P) | −AA Cos (P-Q) | AB Cos (P-R) | −AB Cos (P-S) |
|---|---|---|---|---|
| | −AA Cos (Q-P) | AA Cos (Q-Q) | −AB Cos (Q-R) | AB Cos (Q-S) |

|           |           |           |           |
|-----------|-----------|-----------|-----------|
| BA Cos (R-P) | −BA Cos (R-Q) | BB Cos (R-R) | −BB Cos (R-S) |
| −BA Cos (S-P) | BA Cos (S-Q) | −BB Cos (S-R) | BB Cos (S-S) |

Self-Mixer Output (Demodulated) after equation simplification:

|           |           |           |           |
|-----------|-----------|-----------|-----------|
| AA | −AA Cos (P-Q) | AB Cos (P-R) | −AB Cos (P-S) |
| −AB Cos (Q-R) | AB Cos (Q-S) | −BB Cos (R-S) | BB, | where AA and BB are DC components.

Demodulated components that contain reflected signal information (can be static as well as movement related):

| | | | |
|---|---|---|---|
| −AB Cos (Q-R) | AB Cos (Q-S) | AB Cos (P-R) | −AB Cos (P-S) |

The advantages of this are: no synchronization is required between transmit and receive, as all timing information is contained in the receive only, and it is computationally fast and simple (square an array).

After I, Q (in phase and quadrature) demodulation, there is a choice of how to separate the low frequency components relating to air turbulence, multi-path reflections (including fading related to same) and other slow moving (generally non-physiological) information. In some cases, this processing can be called clutter removal. The DC level (mean) can be subtracted, or some other detrending (such as linear trend removal) performed on an overlapping or non-overlapping block basis; a high pass filter can also be applied to remove DC and very low frequency components (VLF). The "removed" information can be processed to estimate the intensity of such DC and VLF data—such as whether there are strong air currents, or significant multipath effects. The filtered demodulated signal can then be passed to a spectral analysis stage. The other choice is not to use high pass filters and to pass the unfiltered signal directly to the spectral analysis processing block, and carry out the DC and VLF estimation at this stage.

Sensing—Feature Extraction

Spectral analysis can be performed in a number of ways. If using a fast Fourier transform (FFT) to approximate a discrete Fourier transform (DFT), the signal is chopped into overlapping or non-overlapping blocks. In this case it is desirable to perform detrending in advance to deal with the fact that we are approximating an infinitely-long signal with a finite-length one. Windowing (e.g., Hamming, Hanning etc.) may also be performed on the block of data (which may be overlapping or non-overlapping, and the timing of which can be different from the output non-overlapping 30 sec "epochs" such as for a comparison with a sleep study in a PSG lab) prior to performing the FFT, although this may not be desirable where the signal has a strong cyclical component (e.g., a strong deep breathing signal); if windowing is performed, the mean would usually be removed.

An alternative is time-frequency processing such as wavelet based methods (e.g., discretized continuous wavelet transform—DCWT) that can perform both detrending, as well as direct motion and respiration extraction. This type of approach is particularly suited to extracting the much smaller subtle movements related to cardiac movement when there is other movement at the same time (including breathing, limb movement etc.).

Sensing—Absence/Presence Detection—and Alternative Waveforms

In the case of no person or other motion source in the sensing filed, a "static reflection" dominates (usually as a DC offset or a very low frequency component), and can clearly be identified as "absence". Other non-person movements are filtered out, such as low frequency components relating to air currents. The system is so sensitive that it can be configured to detect whether a window or door is left open. The system is also sufficiently robust to accommodate these conditions. Other slow moving sources such as air conditioning or forced heat, as well as relatively fast moving periodic sources (such as fans and oscillating fans) are filtered out.

The smart speaker may be usable outdoors (e.g., in a portable, weather resistant device), but will auto disable the sensing if large air currents are detected.

The system may perform additional processing to manage the sensing signal during high volume music playback (e.g., where there is borderline distortion in the system, as amplifiers and/or the speaker(s) are pushed into non-linear regions).

Sensing—Multimodal/Hybrid Sensing

A continuous wave (CW) system can detect "anything" (i.e., general motion in room) using fast detection, but lacks accurate range gating, and is relatively poor for fading. An enhancement is to use multitone CW to prevent fading. To localize motion—one can use range gating—for that reason it is desirable to use FMCW, UWB, or some other modulation scheme such as frequency-shift keying (FSK) or phase-shift keying (PSK). FMCW does not have sharp nulls like CW can, assists range gating and is resistant to the buildup of modes in a room.

In other words, a waveform such as a dual or multi-tone continuous wave (CW) can be used to sense any movement in an area such as a large room. The multiple tones are selected so as to minimize any nulls caused by standing or travelling waves generated due to multi path reflections and/or reverberation. The advantage of this approach is that it allows any motion to be detected, and use potentially louder signals to fill the space. It can thus be used as a sensitive motion detector, and act as an intruder detector. When a candidate motion is detected, the system searches for likely candidate physiological signals, such as a user walking into the room, typical activity sequences, and then breathing, heart rate, and characteristic movements such as gestures. The system may switch from a CW style system that does not directly provide range information, to a system that can detect at specified ranges, and track motion—such as frequency modulated continuous wave (FMCW) or ultra-wide band (UWB) signal.

A UWB system may be audible or inaudible, depending on the frequency response of speaker and mic; if these components can support higher frequency, a wide band signal may still be outside human hearing. For more typical consumer speakers, a UWB sound is more likely to be audible, and can be shaped to sound like filtered white noise (e.g., pink noise—or some variant that does not sound "harsh" to the human ear). This may be acceptable when sleeping for example, by mimicking a white noise generator. Otherwise, UWB is another option to provide range based sensing when the user is away from home for security applications.

In some versions, the sensing may be performed with multiple sensing apparatus, such as using any two or more of types of sensing apparatus (e.g., any two or more of acoustic sensing apparatus, RF sensing apparatus and IR sensing apparatus.) For example, a processing device may detect motion with RF sensing and acoustic sensing (e.g., FMCW). A processing device may detect motion with IR sensing and acoustic sensing (e.g., FMCW). A processing device may detect motion with IR sensing and RF sensing. A processing device may detect motion with IR sensing, RF sensing, and acoustic sensing (e.g., FMCW)

Coexistence of Different Sensing Devices/Applications

It can be seen that coded or uncoded ultrasonic signals may be generated by different devices to permit devices and systems to implement identification and other data interchange purposes. For example, a mobile phone application may be configured to generate such signals for communication purposes in order to identify itself to another sensing enabled device/system in its proximity, such as a smart speaker and vice versa. These types of signals may be used in place of short range radio frequency communication (e.g., where Bluetooth is not available or is disabled) for identification. The device of the system can then automatically determine existence of other processing devices in the sensing vicinity (e.g., via inaudible acoustically generated communication signals from another processing device) and adjust the parameters of the generated sensing signals so that they can operate in non-interfering sensing modes (e.g., by using different frequency bands and/or not overlapping in time).

Biometric Sensing with Smart Speakers

A smart speaker or similar device typically includes communication via a wireless means (such as Bluetooth, Wi-Fi, Zig Bee, mesh, peer to peer networking etc.) to and from other connected home devices for home automation (e.g., smart automated appliance, smart lighting, smart thermostats, or smart power switches for powering appliances etc.) and a network such as the Internet, for example, as illustrated in FIG. 13. Unlike a standard speaker that is designed to simply emit an acoustic signal, a smart speaker usually includes one or more speakers, one or more microphones in addition to processing electronics. The microphone(s), speaker and processor(s) may be implemented to interface to intelligent assistants (artificial intelligence (AI) systems) in order to provide personalized voice control. Some examples are Google Home, Apple HomePod, Amazon Echo, with voice activation using "OK Google", "Hey Siri", "Alexa" phrases. These devices and connected sensors may be considered to be part of the "Internet of Things" (IoT).

When incorporating the previously discussed ultrasonic detection technology (using audible or inaudible acoustic signals) into a smart speaker, certain optimizations are required based on their capability (either estimated at design time of the smart speaker system and/or updated based on actual performance of a specific device). Broadly speaking, the maximum frequency supported by both the speaker(s) and microphone(s) will ultimately define the highest frequency inaudible sensing signal that can be used, and this may vary slightly based on manufacturing tolerances for a specific device.

For example, a speaker in a first device (e.g., a Google Home device) might have different characteristics to the speaker in a second device, such as a Samsung Galaxy S5 smartphone. The first device speaker might be sensitive up to 24 kHz, with a nearly flat microphone response to a similar frequency. However, the second device might have as speaker that rolls off at a lower frequency, with peaks and troughs in sensitivity over 18 kHz. A speaker of an Amazon Alexa device might roll-off at 20 kHz for example. An exemplar Google device might use a passive reflex speaker design to phase invert waves coming back and send them out sideways, which changes its acoustic characteristics (e.g., a "10 kHz" speaker becomes 25 kHz speaker in effect).

Some devices may have microphone arrays, such as a number of microphones on flat plate, and they may implement gain and averaging functions—but with separation between the microphone elements (e.g., a dynamic array diverse array). Such processing can be done numerically, i.e., in the digital domain using digital signal processing.

One potential difference to be managed with respect to such systems relates to the orientation of the speaker(s) and microphone(s). For example, on certain implementations, the speakers may face forwards, and can be pointed in the likely direction of the user. However, the microphone(s) might face 20-30 degrees towards either the room or ceiling.

Thus, in order to optimize sound pickup for distance acoustic sensing, the application may be configured to generate, via the speakers, probing sequences to learn the topology of the room, and allow for the likely reflection paths. Thus, a setup process can generate the sequences to calibrate distance measurement of the low frequency ultrasonic echoes (e.g., to support the monitoring of multiple persons or motion sources simultaneously, when they are at different distanced from the smart speaker). From a signal processing perspective, the reverberation floor (how long it takes for the energy of reflecting acoustic waves to dissipate) will be different for different sensing signals—e.g., with a factor of 2-3 for CW (continuous wave), and a factor of around 5 (i.e., reduced reverb) for FMCW (i.e., FMCW can still suffer from reverb fading, depending on the frequency span, duration, and shape of the repeating sequence).

Microphone separation can present difficulties. For example, where a microphone array in a common housing is available on a smart speaker, an exemplar separation of microphones might be 71 mm apart. For a 20 mm wavelength, this implies that one microphone could be in a trough, while the other is in a peak area (e.g., as you move for a fixed speaker, the SNR will vary between microphones). A desirable construction could be to have configured two microphones with a particular audio sensing wavelength related spacing in region of 19-20 mm. Where such a distance is unknown for a pre-configured system, a calibration process, such as part of the setup process, can detect the distance. For example, the setup process can generate time synchronized calibration sounds via one or more speakers to calculate or estimate the time of flight from each speaker to each microphone and estimate difference between the microphones based on these calculations. Thus, the distances between the microphones can be taken into account when sensing distance from the smart phone with two or more microphones.

Other devices such as active sound bars (i.e., including microphones), and mobile smart devices can also be implemented with the sensing operations described herein.

The presence of at least one speaker and at least one microphone (or transducers that can be configured to perform these functions) allows biometric sensing to be performed on these devices using active low frequency ultrasound, and processing the echoes of same. As previously mentioned, this can be implemented by playing (transmitting) an acoustic signal that is, for example, just outside the hearing range of most users (e.g., above 18 kHz) but within the known or determined system capability (e.g., could be below 24 kHz for a sampling rate of 48 kHz, but is usually below 25 or 30 kHz). In contrast, medical ultrasound usually operates at much higher frequencies—for example 1-18 MHz and requires specialized equipment for these operations. The discussed ultrasonic measurement technique offers a convenient non-contact measurement without the need to purchase any expensive equipment—by just using the smart speaker systems (including smart phones) already available in almost every household.

Multi-User Vicinity Sensing

In some versions, the processing device may be configured to monitor two people (or more) at the same time with a one or more speaker(s) and one or more microphone(s). For example, a processing device may produce multiple sensing signals at different sensing frequencies for sensing different users with different frequencies. In some cases, it may control producing interleaved sensing signals (e.g., different sensing signals at different times) for sensing different users at different times. In some cases, it may adjust sequentially adjust range gating for sensing different ranges at different times (e.g., for in parallel sensing).

In some cases, there are some conditions that can help to maximize signal quality. For example, a processing device (e.g., either an RF sensor, or a SONAR enabled smartphone) may be placed on a bedside locker. In this case, there might be a "shadowing" effect of the first person whose body can block quite a lot of the sensing signal (and actually benefits range gating (sensing just one person in bed). In SONAR, the processing device can generate two (or more) different sensing signals—or even a single FMCW (triangle, dual ramp or other) sensing signal to detect two (or more) people. The range separability of FMCW means that one sensing signal is sufficient (such as if there is only one speaker/mic in the room). Ideally, to monitor two people at the same time, a user may places the processing device in an elevated position so that the majority of the acoustic energy reaches both users (for example so that the first user and his/her sheet/duvet comforter does not block too much of the sensing signal). If there are two microphones on the same device, this can also provide an advantage if there is significant constructive/destructive interference (e.g., as it may be closer to a peak on one, and a null on the other—especially for the smaller amplitude receive signals from the more distant subject).

It may be more beneficial (and potentially achieve a higher signal quality), if there is a SONAR/smartphone closer to the second person. The second person may use their smartphone/processing device and the first person uses their smartphone/processing device. The sensing signals can be generated to avoid interference with each other (i.e., keep from overlapping in time and/or frequency). The devices may automatically sense the environment (either by listening before transmitting and/or processing the received signal when we are transmitting) so as to selective choose a sensing signal modulation/technique that does not interfere with pre-existing sensing signals from other devices in the vicinity.

In some cases, the sound pressure level of the transmit and the receive sensitivity are such that two smartphones with exactly the same transmit sensing signal will not cause interference, as the mixture of air attenuation, and acoustic absorptive surfaces (fabrics, carpets, bed clothing etc.) can have an impact that keeps the second source below an interference threshold. If each processing device used by a respective user, the devices can be configured to optionally automatically decrease the output power of each so that biometrics signals of the monitored subject may be sufficiently detected such as with the lowest necessary output power. Such processes can permit each to detect motion while avoiding interference with other devices.

Sensing—Physiological Signals

After separation of DC and VLFs (e.g., air currents), respiration, heart rate and gross motion signals are separated. These can be estimated by bin searching in the FFT windows, and tracking across windows, and/or via direct peak/trough or zero crossings analysis of a time domain signal at a specified range (e.g., a "time domain" signal for a specified distance range extracted using a complex FFT analysis of the demodulated signal). This permits selection of a range with user motion. This is sometimes referred to as "2D" (two dimensional) processing as an FFT.

Biometric Feature Detection—Respiration, Cardiac, Movement, and Range

The time domain signal (the baseband raw motion signal) can be further band pass filtered, have an envelope detector applied, and then a peak/trough detector applied. Envelope detection may be performed with a Hilbert transform or by squaring the respiratory data, sending the squared data through a low-pass filter, and calculating the square root of the resulting signal. In some examples, the respiratory data (derived by the band pass filtering) may be normalized and sent through a peak and trough detection (or alternatively a zero crossing) process. The detection process may isolate the inspiration and expiration portions, and in some cases may be calibrated to detect the user's inspiration and expiration portions.

The respiratory activity is typically in the range 0.1 to 0.7 Hz (6 breaths per minute—such as arising from paced deep breathing to 42 breaths per minute—an atypically fast breathing rate in adults). The cardiac activity is reflected in signals at higher frequencies, and this activity can be accessed by filtering with a bandpass filter with a pass band of a range from 0.7 to 4 Hz (48 beats per minute to 240 beats per minute). Activity due to gross motion is typically in the range 4 Hz to 10 Hz. It should be noted that there can be overlap in these ranges. Strong (clean) breathing traces can give rise to strong harmonics, and these need to be tracked in order to avoid confusing a breathing harmonic with the cardiac signal. At longer distances from the transducer (e.g., several meters), it can be very challenging to detect the relatively small cardiac mechanical signal, and such heart rate estimation is better suited to settings where the user is lying quietly within a meter of the smart speaker—such as on a chair/couch or in bed.

Once absence/presence has been determined as "presence", an estimate of the respiration, cardiac, and motion/activity signals—as well as their relative position (and velocity if moving—such as walking across a room)—is performed for one or more persons in the field of the sensor. It can be seen that a system that yields ranging information is capable of separating the biometric data of multiple persons—even if the multiple persons have similar resting breathing rates (which is not uncommon in young couples).

Based on these parameters, it is possible to prepare a variety of statistical measures (e.g., average, median, $3^{rd}$ and $4^{th}$ moments, log, square root etc.), wave shape (morphological processing), and then supply to a characterization system, such as a simple classification or logistic regression function, or a more complex machine learning system using neural networks or artificial intelligence system. The purpose of this processing is to gain further insights from the gathered biometric data, such as for identifying a known user in the vicinity of the device.

Low Frequency Ultrasonic (SONAR) Sensing

Many places contain audio devices that are capable of emitting and recording sounds in the low frequency ultrasonic range at just above the human hearing threshold—e.g., infotainment systems. Such devices and systems can be adapted to perform physiological sensing of the people in the vicinity using low frequency ultrasonic techniques. Such sensing may be performed without impacting the original intended functions of the standard audio systems. In one example, such a sensing functionality can be implemented by way of a software update (i.e., allowing additional useful functionality to be added without increasing the cost of goods). In some cases, one or more of the transducers in a new device or system may be specified to support the audio frequency ranges for low frequency ultrasonic sensing, with additional testing at manufacture to ensure they meet this specification.

Such acoustic (either audible or inaudible) sensing technology can be used for a wide variety of purposes including pro-active health management, medical devices, and security functions.

A low frequency ultrasonic system operating up to around 25 kHz can be realized on a mobile smart device or smart speaker device. This transmits sound energy towards one or more subjects using one or more transducer on the electronic device, where the transducer is configured to generate sound energy over a range of frequencies that includes frequencies less than 25 kHz. The speakers could be contained in a smart phone, a smart speaker, a sound bar, a portable TV screen, or many other devices and configurations that contain transducers capable of supporting low frequency ultrasonic sensing and processing. If a computer is implemented to control a speaker system, it effectively creates a smart speaker system.

Audible sounds such as the sound of breathing, coughing, snoring when asleep, gasping, wheezing, speech, sniffing, sneezing can be extracted and classified from the sensed audio signal within the vicinity so as to permit isolation of these sounds from the reflected sensing signal that will be detected for motion sensing. Some of these sounds (e.g., a cough) can mask the sensing signal (especially if it is operating at a very low sound pressure level), which is not desirable. However, such sounds may still be detectable so that they can be separated from other environmental sounds (e.g., a car horn blowing, motor noise, street sounds, wind, a slamming or closing door etc.). The sound of breathing is typically of better signal quality in a quiet environment, and can provide a good second estimate of inspiration/expiration time (and thus breathing rate) when complimented with an active sensing approach such as SONAR or RADAR (including an RF one) (which are primarily detecting torso and limb movements), or camera/infra-red systems. In other words, the system can still extract information about the characteristics of sounds, even very loud sounds mean that a system may skip small sections of the sensed signal as the associated signal quality drops below an acceptable threshold.

In SONAR systems, the air movement caused by an inspiration or expiration may also be detected by methods that track the resulting travelling wavefront (due to the disturbance of acoustic modes set up in the sensing environment—if the sensing signal persists long enough to experience reverberation). Detecting snoring directly from the audible signature is easier, as it be a relatively loud process for example, by using a mean maximum decibel level to classify snoring as mild (40-50 db), moderate (50-60 db), or severe (>60 db).

Thus, in some cases, the processing device 100 may use motion detection (e.g., Sonar) techniques for detecting respiration. However, in some cases, acoustic analysis, of an audible breath signal at the microphone, may be implemented by the processing device 100 for the detection of respiration.

RF (RADAR) Sensing

Some systems may include single pulse Doppler RADAR modules for simple interior movement detection for security. These may be enhanced (with updated software) or replaced with modules that can localize motion detection to specific areas of a vicinity—particularly to be able to detect and distinguish a person on each seat/sitting area. The sensor may be enhanced with technologies such as ultrawideband (UWB) sensing signals or frequency modulated continuous wave (FMCW) sensing signal or including other coding schemes such as OFDM, PSK, FSK etc. in their generated sensing signals. These can be implemented with a sensor having an accurate ranging ability (1 cm or less). Such a sensor may sense in a defined area (e.g., set via the antenna design that may be configured within the vicinity to have a particular seat oriented sensing direction). In some cases, multiple antennas may be implemented for a particular sensing area and may be used with beamforming techniques to set the distance sensing differences associated with the different antennas. Multiple sensors can be used in an area to provide coverage of multiple areas that a person (or pet) could be in (e.g., a sensor for each seat).

Multimodal Data Processing

When using SONAR, RF, or infra-red sensing (i.e., infra-red emitters and detectors for IR wave transmission and reception), a processing device 100 may receive additional data or signals generated by equipment of a vicinity (e.g., to estimate occupancy) so that biomotion sensing may be based on data from such equipment. For example, seat/bed load sensors that detect whether a person sitting on a given seat or in bed may provide the biomotion processing device 100 with information to determine when to initiate biomotion sensing with respect to sensing that may be associated with a particular seat or bed. An infra-red system may optionally, for example, be incorporated with a camera system that can track human eye movement, such as for sleepiness detection.

The processing device may be configured with distance information for evaluating relevant ranges/distances for detection of biomotion characteristics. For example, the processing device 100 may have a distance mapping (map) of a vicinity interior—such as of room. Such a map may be provided initially, e.g., at the design stage, to specify an initial sensing configuration. Optionally, the sensing system, under control of the processing device, may dynamically update (or detect) a map of the when in use by one or more persons. An initial configuration may, for example, capture/detect the position of seats, and most likely seat configurations; where seats are movable, sensors can report the current settings to the system to update the sensing parameters (e.g., the position of a person sitting could move with respect to a sensing loudspeaker, as seat slides backwards or forwards, or is folded down etc.).

Biometric Feature Detection—Respiration, Cardiac, Movement, and Range

Processing Sensor Signals

The system, including particularly processing device 100, may receive demodulated signals from a sensor (such as from SONAR, RF/RADAR, or infra-red) such as optionally if demodulation is not performed by the processing device. The processing device 100 may then process the signal by separating components of interest such as direct current signals DC and very low frequencies VLFs (e.g., air currents), respiration, heart rate and gross motion signals. These can be estimated/detected by bin searching in fast Fourier transform (FFT) windows, and tracking across windows, and/or via direct peak/trough or zero crossings analysis of a time domain signal at a specified range (e.g., a "time domain" signal for a specified distance range extracted using a complex FFT analysis of the demodulated signal). This is sometimes referred to as "2D" (two dimensional) processing as an FFT is performed of an FFT such as described in International Patent Application PCT/EP2017/073613.

For SONAR sensing, significant other information can be found in the audio band and picked up by the microphone. Such information may be infotainment sounds (music, radio, TV, movies), phone or video calls (including human speech), ambient noise, and other internal and external sounds such as motor, traffic or vehicle noise. Most of these audio components can be considered to be interferers, and may be suppressed (e.g., filtered) from biometric parameter estimation.

For RADAR sensing, signal components from other RF sources may be suppressed.

For infra-red sensing (such as when carrying out physiological sensing in addition to eye tracking), temperature changes and sun position may cause interference and may be taken into account. Thus, temperature sensors, such as from a thermostat temperature sensor, and time may be evaluated in processing the sensing signal.

Regardless of the exact sensing technique used (RF, IR, SONAR), the received time domain reflected signal can be further processed (e.g., by bandpass filtering with a bandpass filter, evaluated by an envelope detector, and then by a peak/trough detector). Envelope detection may be performed with a Hilbert transform or by squaring the respiratory data, sending the squared data through a low-pass filter, and calculating the square root of the resulting signal. In some examples, the respiratory data may be normalized and sent through a peak and trough detection (or alternatively a zero crossing) process. The detection process may isolate the inspiration and expiration portions, and in some cases, may be calibrated to detect the user's inspiration and expiration portions.

The respiratory activity is typically in the range 0.1 to 0.7 Hz (6 breaths per minute—such as arising from paced deep breathing to 42 breaths per minute—an atypically fast breathing rate in adults). The cardiac activity is reflected in signals at higher frequencies, and this activity can be accessed by filtering with a bandpass filter with a pass band of a range from 0.7 to 4 Hz (48 beats per minute to 240 beats per minute). Activity due to gross motion is typically in the range 4 Hz to 10 Hz. It should be noted that there can be overlap in these ranges. Strong (clean) breathing traces can give rise to strong harmonics, and these need to be tracked in order to avoid confusing a breathing harmonic with the cardiac signal. At longer distances from the transducer (e.g., several meters), it can be very challenging to detect the relatively small cardiac mechanical signal, and such heart rate estimation is better suited to settings where the user is lying quietly within a meter of the smart speaker—such as on a chair/couch or in bed.

Once absence/presence has been determined as "presence", an estimate of the respiration, cardiac, and motion/activity signals (as well as their relative position and velocity if moving—such a such as moving in and out of the vicinity) is performed for one or more persons in the field of the sensor. It can be seen that a system that yields ranging information is capable of separating the biometric data of multiple persons—even if the multiple persons have similar resting breathing rates (which is not uncommon in young couples).

Based on these parameters, it is possible to prepare a variety of statistical measures (e.g., average, median, $3^{rd}$ and $4^{th}$ moments, log, square root etc.), wave shape (morphological processing), and then supply to a characterization system, such as a simple classification or logistic regression function, or a more complex machine learning system using neural networks or artificial intelligence system. The purpose of this processing is to gain further insights from the gathered biometric data.

Sleep Staging Analysis

As absence/presence/wake/(NREM) sleep stage 1/sleep stage 2/sleep stage 3 (slow-wave sleep SWS/deep)/REM has a sequence related to the underlying sleep architecture representing sleep cycles, it can be helpful to consider this as a sequenced rather than un-sequenced problem (i.e., reflecting typical sleep cycles, where a person remains in one state for a period of time). The sequence of sleep imposes an explicit order on the observations throughout for example the night (a "sleep").

Some systems may also take advantage of knowledge of a "normal" sleep pattern having a more (higher prevalence) deep sleep (SWS) towards the beginning of the night, and more REM sleep towards the end of the night. This prior knowledge, which could be used to weight (e.g., adjust prior probabilities of these states over time) a classification system for normal sleepers; however, it should be noted that these assumptions from population normative values may not hold for non-normal sleepers, or those that regularly nap during the day—or have poor sleep hygiene (poor sleep habits—such as widely varying 'to-bed' and 'out-of-bed' times).

Classically, sleep staging has been considered in 30 second "epochs" dating back to the Rechtschaffen & Kales guidelines (Rechtschaffen and Kales, 1968) (a manual of standardized terminology, techniques and scoring system for sleep stages of human subjects. U.S. Public Health Service, U.S. Government Printing Office, Washington D.C. 1968) which when looking at electroencephalogram EEG found a 30 sec interval ideal for viewing alpha and spindles as a paper speed was 10 mm/s (one page equates to thirty seconds). Of course, the real physiological process of sleep and wakefulness (and absence/presence) will not evenly split into 30 sec blocks, so a longer or a shorter time can be selected. The system outlined here preferentially uses a 1 second (1 Hertz) sleep stage output, although it uses longer blocks of data in an overlapping fashion to deliver an update every 1 second (1 Hertz) (with an associated delay related to the size of the underlying processing block). This 1 second output is used in order to better show subtle changes/transitions in the sleep cycle.

Sleep Features—Manually Versus Automatically Generated

The sensed signal (a signal representing distance verses time (motion) information) is used to calculate various features, such as sleep features. These features can then be used to derive information regarding the user's physiological state.

For feature generation, a number of approaches may be implemented. For example, a human expert can manually produce features from the processed or unprocessed signals based on their experience, by looking at the respiratory and other physiological data and its distributions, understanding the physiological basis of particular changes, and trial and error. Alternatively, a machine can "learn" the features with some human supervision (a core concept of the field of "machine learning") where labeled data with the expected outcome is supplied and some human help provided, or in a fully automatic way where some or no labeled data may be supplied.

Deep learning can be broadly considered in the following broad categories: deep neural nets (DNN), convolutional neural nets (CNN), recurrent neural nets (RNN), and other types. Within DNNs, one can consider deep belief networks (DBN), multilayer perceptron (MLP), as well as stacked auto-encoders (SAE).

A Deep Belief Network (DBN) possesses a generative capability, e.g., to automatically generate features from input data. Another approach for this purpose is Fuzzy C-Means clustering (FCM), a form of unsupervised learning that aids finding the inherent structure in pre-processed data.

Handcrafted features can be formed by applying digital signal processing techniques to sensed movement data. A respiration signal in an ideal case is perfectly sinusoidal with two amplitudes (deep or shallow) and a constant frequency (constant breathing rate), described as you breathe in and then out. In the real world, it can be far from sinusoidal—especially as detected from the torso area via and acoustic or radio frequency based sensing approach. For example, an inspiration may be sharper than an expiration, and faster, and there may be a notch on the waveform if breath is held for a moment. The inspiration and expiration amplitudes, as well as the respiration frequency, may vary. Some extraction methods focus on detecting the peak and trough, then detecting the better quality of the two (say detecting a local peak and discarding the trough). This is not ideal if both the peak and the trough times are needed in order to estimate both inspiration and expiration times, as well as volumes (e.g., calculated by integration of the time domain signal versus a calculated reference baseline)—but can be good enough for a respiration rate estimate.

Various methods can be used to assist in the estimate of any of these features, such as the respiratory and/or heart rate or amplitude.

For example, a peak and trough candidate signal extraction requires recovering the respiratory wave shape from noise (and there can be a variety of out—ofband and in-band noise, usually with a preponderance of lower frequency noise which can complicate the accurate detection of lower breathing rates (e.g., 4-8 breaths per minute, which while unusual for spontaneous breathing, can arise if a user is asked to guide their breathing to slower rates). Time domain detection methods include max and min detection after low pass filtering, using an adaptive threshold (that adjusts over a block of multiple breaths to allow deep and shallow breaths to be detected). Optionally, the signal may be low pass filtered and differentiated (e.g., a derivative function). Peaks in the differentiated signal relating to max rate of change may then be detected to provide an indication of breath event. Such a method extracts fiducial points of a respiratory waveform that is modeled as a sinusoid with some noise on it. The LPF removes higher frequency noise. Differentiation is then done and peaks are detected. In effect, this finds points of maximum rate of change of the original signal, rather than the peaks and troughs of the original signal—as a respiratory waveform is often clearest at maximum rate of change rather than a say a wide peak (for example, if there is a breath hold for a short amount of time). A potentially more robust method is to detect zero crossings (around a fixed or adaptive baseline), as the crossings of this boundary is not directly impacted by local changes in the amplitude of the signal.

While respiration signals may be easily visible in the time domain signal (depending on the distance and angle of the chest from the sensor(s)), the cardiac motion is typically a very small signal in comparison to respiration. Higher order harmonics of respiration (e.g., related to the wave shape) can complicate the cardiac signal extraction, and need to be rejected, or detected and excluded.

Frequency domain methods can also be applied, for example to the respiratory data. These methods can include using a detected peak in a band of an FFT (which may be windowed to combat spectral leakage) using a block of data that may be overlapped (e.g., a block of 30 s of data of a data stream that is repeatedly shifted by for example, one second) or non-overlapped (e.g., the data stream is considered to be non-overlapping in thirty second chunks). A power spectral density PSD using Welch's method, or a parametric model (autoregressive) may also be used, with a subsequent peak search. A spectral peak will tend to be wider (more spread) as the respiration signal becomes less sinusoidal, and can include harmonics if the shape has sharp peaks, sharp troughs, or notches. Another method is to use autocorrelation (describing the similarity of a signal to a shifted version of itself), where an assumption is that the underlying respiration wave shape is relatively stable for a period of time, and a periodic local maxima in the autocorrelation can be tracked and filtered by most likely candidate (e.g., not related to noise) maxima in order to estimate breathing rate. Autocorrelation can be carried out in the time domain, or by FFT in the frequency domain. Time frequency approaches, such as wavelets are also useful where a suitable wavelet with a sinusoidal shape are selected (e.g., symlet, Debauchies etc.), that can perform strong de-noising; again, a peak detection is ultimately performed at the time scale of interest (i.e., within the target breathing rate range).

A Kalman filter (a recursive algorithm) can be applied to the time domain signals to estimate the system state; this approach provides a way to predict a future unknown state of a system, based only on the use of the preceding step. In addition to filtering, it can provide signal separation, such as of large movement, respiration, and cardiac movements.

(Noise Contaminated Observations (e.g., for Detecting Physiological Movement in Noisy Environments)

Any detection of respiration peaks and troughs needs to be aware of potentially confounding effects, such as the subject making a large movement (such as rolling in bed or moving while driving), if the subject stops breathing (e.g., an apnea) or exhibits very shallow breathing (e.g., a hypopnea). Using sensing that can track location provides a useful means of separating these effects. For example, a roll can be seen as both a high frequency movement, as well as change in location in space. Therefore, subsequent breaths may be higher or lower in amplitude—but still be "healthy" breaths. In other words, the detected amplitude change may be due to a change in the extracted received respiration signal (after down-conversion etc.) strength, rather than a change in the person's breathing. Therefore, it can be seen that this can allow a novel calibration approach, where the detected distance can be used to relate signal strength to depth of breathing (and hence approximate tidal volume). Where no such movement or displacement is seen, a diminution, cessation, or change (e.g., due to paradoxical movement on chest and abdomen during an obstructive event) of a specified duration range can be identified as abnormal breathing (e.g., an apnea/hypopnea event).

It can be seen that a practical, robust cardiorespiratory estimation system can rely on multiple methods to localize the parameters. For good signal quality cases, a frequency (or time frequency) estimate can localize the likely breathing rate, an estimate of local breathing variability, then extract subtle peak and trough times, and perform calibration with range in order to estimate inspiration and expiration volumes (useful features for sleep staging). Such a signal quality metric is expected to vary over time. If there is a variation in the measured breathing rate, the processing can be done over different time scales, e.g., averaging or median filtering over 30, 60, 90, 120, 150 seconds etc.

In the SONAR case, the envelope of the raw received waveform (e.g., of an acoustic FMCW signal) can be processed as a main, or as a secondary input such as when other additional sensing signals are implemented, for respiration rate estimation (such as for using SONAR to provide extra information for an RF sensing system or vice versa). This is based on the property of detecting the actual disturbance in the air of the exhaled breath of a person. This does imply that there are not other strong air currents in the cabin, room or vicinity (e.g., from an open window, a nearby air conditioning unit, a nearby heater etc.); if there are, their effect on the measurement can either be discarded, or used to detect changes in airflow in the environment.

Large air currents will tend to be detectable as a low frequency movement across range bins (i.e., a perturbation that flows across the range). This is more evident for sensing waveforms that have more reverberation (e.g., that allow the energy of one frequency to build up in the room, and associated room modes).

When considering a sleep staging system that works across a general population (i.e., including users with a withal healthy condition, users with various health conditions, including respiratory conditions such as sleep apnea, COPD, cardiac issues and so forth), it can be seen that the baseline of respiration rate and heart rate can vary widely. Take for example differences in age, gender, and body-mass index (BMI). Women may have a slightly higher baseline breathing rate than men for a similar age and BMI (although a recent study in children ages 4-16 does not show a statistical difference). Those with higher BMIs will tend to breathe faster than the average of somebody of a similar age. Children normally have much higher normal respiratory rate than adults.

Thus, in some versions, the system such as with processing device 100 regardless of sensor type, may be made with a hybrid implementation, such as where initial signal processing and some hand crafted features are formed, prior to applying a deep belief network (DBN). (A hybrid implementation involves a mixture of human "hand crafted," digital signal processing (DSP) derived features combined with features learned by a machine.) Initial supervised training is performed using expert score polysomnography (PSG) overnight datasets from a sleep lab or home PSG, from multiple sites around the world, and scored by at least one scorer, using a specified scoring methodology. Further unsupervised training is performed from datasets gathered with one or more of the selecting sensing methods. This allows the system to evolve to reflect new and more diverse data outside of the sleep lab.

In terms of hand-crafted features (i.e., a human engineer/data scientist has designed, chosen or created them), a breathing signal with associated signal quality level is extracted, with specific features of interest being the variability of the breathing rate over different timescales, and the variation in inspiration and expiration time. An estimate of a personalized baseline breathing rate for awake and asleep is formed. It is known for example that short-term changes in breathing rate variability while awake can be related to mood, and changes in mood, whereas these changes while asleep are related to changes in sleep stage. For example, respiration rate variability increases in REM sleep. Longer term changes in breathing rate itself can be related to changes in mental condition, such as providing indicators of mental health. These effects may be more profound when the user is asleep, especially when analyzed over longer timescales, and compared to population normative values.

One can use the variability of the measured respiratory rate as an indication of the user's state (sleep/awake) or sleep stage (REM, N1, then N2, then lowest in SWS sleep). For example, when looking at normalized respiratory rate variability over a period such as 15 mins in a normal healthy person, it is possible to see greatest variability when they are awake; this variability drops in all sleep states, with the next largest being in REM sleep (but still less than wake), then reducing further in N1, then N2, then lowest in SWS sleep. As an aside, air pressure due to breathing can increase in REM sleep, which can have an impact on the acoustic signal detected—a potential extra feature that could be detected in quiet environments or at quieter times.

Such normalized respiratory rate values should not vary significantly between different positions (supine, prone, on side etc.) for a healthy person. However, it should be noted that calibration to the correct tidal volume is likely to be desirable. For example, the system may normalize over the entire night since one person's average breathing rate might be, for example 13.2 breaths per minute (BR/MIN) while asleep whereas another person's average might be 17.5 BR/MIN. Both rates exhibit similar variability per sleep stage. The difference in rate is merely masking the changes that may be considered for classifying the sleep states. The system can consider the average rate (or overall rate graph) for other purposes such as comparing to themselves over time, or indeed to someone in a similar demographic. For a person with obstructive sleep apnea (OSA), it is expected that respiratory variability will increase in the supine position (lying on back)—a potentially useful indication of the user's respiratory health.

Subjects with mixed apnea or central apnea tend to display larger respiratory variability during wake than normal subjects (a useful biomarker); which those with obstructive apnea also have changes versus normal during wake, which are not as obvious (but still present in many cases).

Person specific sleep patterns (e.g., breathing variability) can be learned by the system over time; thus, a system that can perform unsupervised learning, once deployed in the field, is highly desirable.

These patterns can vary overnight (i.e., during a sleeping session) and can be impacted by apneas occurring during the sleeping time, as partial or complete cessation of breathing (or paradoxical movement of the chest and abdomen when there is an obstructed airway). It can be seen that one way to deal with this issue is by suppressing the periods with detected apneas (and the associated oscillations in breathing rate), if calculating sleep stages. One can simply flag apneas and potential micro-arousals, rather than attempting to classify the sleep stage at that point in time. Periodic breathing patterns, such as Cheyne Stokes respiration (CSR), have a strong oscillatory pattern; these may also be detected during a sleep pre-processing stage. While CSR can occur in any stage of sleep, the pauses tend be more regular in Non-REM sleep, and more irregular in REM sleep (information which the system can use to refine sleep staging in subjects with CSR).

Similarly, a cardiac signal can be extracted with processing steps that suppress any harmonics relating to the breathing waveform morphology. Specific patterns such as obstructive, mixed or central apneas are detected, along with any related recovery breaths, and movements related to gasping. From the cardiac signal, a beat to beat "heart rate variability" (HRV) signal is estimated based on physiologically plausible heart rate values. Spectral HRV metrics can be calculated, such as the log power of the mean respiratory frequency, LF/HF (low frequency to high frequency) ratio, log of the normalized HF and so forth.

The HF spectrum of the beat to beat time (HRV waveform) is the power in the range 0.15-0.4 Hz, relating to rhythms of parasympathetic or vagal activity (respiratory sinus arrhythmia—or RSA) of 2.5 to 7 seconds, and is sometimes referred to as the "respiratory band".

The LF band is 0.04-0.15 Hz, which is believed to reflect baroreceptor activity while at rest (and some research suggests may have a relationship with cardiac sympathetic innervation).

The VLF (very low frequency) HRV power is between 0.0033-0.04 Hz (300 to 25 seconds), and reduced values are related to arrhythmias and post-traumatic stress disorder (PTSD).

HRV parameters can also be extracted using time domain methods, such as SDNN (standard deviation of normal inter-beat interval—to capture longer term variability) and RMSSD (root mean square of successive heartbeat interval differences—to capture short term variability). RMSSD can also be used to screen for irregularly irregular beat to beat behavior, such as seen in atrial fibrillation.

In terms of HRV, a shift in the LF/HF ratio as calculated is detectable characteristic of Non-REM sleep, with a shift to "sympathetic" HF dominance during REM sleep (which may be related from sympathetic to parasympathetic balance).

More generally, there is typically increased HRV in REM sleep.

The longer term mean or median of the breathing rate and heart rate signals are important for a specific person when analyzing over time—especially if there is some intervention, such as a medication, treatment, recovery from an illness (either physical or mental), change in fitness level, change in sleep habits over time. They are somewhat less useful for comparing directly from person to person (unless to a very similar grouping). Thus, for breathing and cardiac variability features, it is useful to normalize these (e.g., de-mean, remove the median etc. as appropriate for the metric) such that that can better generalize across a population.

Further analysis of extracted features can make use of a deep belief network (DBN). Such a network is composed of building blocks of Restricted Boltzmann Machines (RBM), Autoencoders, and/or perceptrons. A DBN is particularly useful to learn from these extracted features. DBNs can be used without supervision, and then later trained with labeled data (that is, data confirmed by a human expert input).

Exemplar human crafted "learn by example" extracted features that can be passed onto the DBN, can include: apnea type and location, respiratory rate and variability of same over different timescales, respiration, inspiration and expirations times, depth of inspiration and expiration, cardiac rate and variability of same over different time scales, ballistocardiogram beat shape/morphology movement and activity types such as gross movement, PLM/RLS, signal quality (integrity of measures over time), user information such as age, height, weight, sex, health conditions, occupation etc.). Other statistical parameters such as skewness, kurtosis, entropy of the signals can also be calculated. A DBN will determine several features itself ("learns" them). Sometimes it can be difficult to understand what exactly they represent, but they can often do a better job than humans. A challenge is they can sometimes end up at bad local optima. Once they have "learned" the features, the system can tune them with some labelled data (e.g., data input by a human expert may score a feature (one expert or a consensus of several experts)).

The DBN can also directly learn new features from the input parameters including from the respiratory waveform, activity levels, cardiac waveform, raw audio samples (in the case of SONAR), I/Q biomotion data (in the case of SONAR or RADAR), intensity and color levels (e.g., from infra-red camera data) and so forth.

A machine learning approach that purely uses hand crafted features is a "shallow learning" approach that tends to plateau in terms of a performance level. In contrast, a "deep learning" approach can continue to improve as the size of data increases. The approach discussed above uses deep learning (in this case a DBN) to create new features for classic machine learning (e.g., take new features, a feature selection winnowing by feature performance, whiten with ICA (independent component analysis) or PCA (principal component analysis) (i.e., a dimensionality reduction), and classify using a decision tree based approach such as random forests or support vector machines (SVM)).

A full deep learning approach, as used here, avoids such a feature selection step, which can be seen to be an advantage as it means that the system does not use sight of the huge variety seen in a human population. New features can then be learned from unlabeled data.

One approach for these multimodal signals, is to train a deep belief network on each signal first, and then train on the concatenated data. The rationale for this is that certain data-streams may simply not be valid for periods of time (e.g., the cardiac signal quality is below a usable threshold, but there is a good quality respiratory, movement, and audio features signal available—in which case, any learned or derived features from the cardiac data would be nonsensical for this period).

For classification, a sequence based approach such as Hidden Markov Models (HMM) can be applied. Such a HMM can still optionally be used at the output in order to separate the sleep stages, in order to map an output sleep graph to a stepped "sleep architecture" as might be provided via a hospital sleep lab PSG system, and minimize unusual sleep stage switching. However, if we recognize that sleep is a gradual physiological process, we may prefer to not force the system to a small number of sleep stages, and allow it to capture gradual changes (i.e., to have many more "in between" sleep states).

A simpler state machine approach with no hidden layers is possible, but ultimately can have problems generalizing across a large population of sleepers, each having their own unique human physiological characteristics and behaviors. Other approaches as Conditional Random Fields (CRF) or variants such as Hidden State CRF, Latent Dynamic CRF, or Conditional Neural Fields (CNF) or Latent Dynamic CNF. It should be noted that Long Short-Term Memory (LSTM) can have good discriminative ability, particularly when applied to sequence pattern recognition (more typical in normal healthy sleepers).

Semi-supervised learning could be performed using a recurrent neural network (RNN), which can be effective in finding structure in unlabeled data. An RNN is standard neural net structure, with Input, Hidden Layers, and Output. It has sequenced input/output (i.e., the next input depends on the previous output—i.e., hidden units have recurrent connections that pass on information) using graph unrolling and parameter sharing techniques. LSTM RNNs are well known for natural language processing applications (with LSTM to combat exploding and vanishing gradient problems).

In terms of detecting sleep onset, if a speech recognition service is running, voice commands by the user can be used as a second determinant of "wake" (not to be confused with nonsensical sleep talking). If a personal smart device is used (unlocked by the user—then with UI input, movement of the accelerometer, gyroscope etc.), this can also be used as a determinant of wake to augment other sleep/wake sensing services.

Sleep Architecture and Personalized Sleep Score

A wide variety of parameters, such as those previously discussed, can be estimated, including a breathing rate, relative amplitude of breathing (shallow, deep etc.), a heart rate and heart rate variability, movement intensity and duration, and an activity index. The processing may then determine whether the subject is awake or asleep and, if asleep, what is their sleep state (light N1 or N2, deep, or REM)—and a prediction of likely upcoming sleep state.

The system can provide a fully automatic, seamless detection of sleep—and the ability to detect two or more people sleeping from one device.

Figure 18:
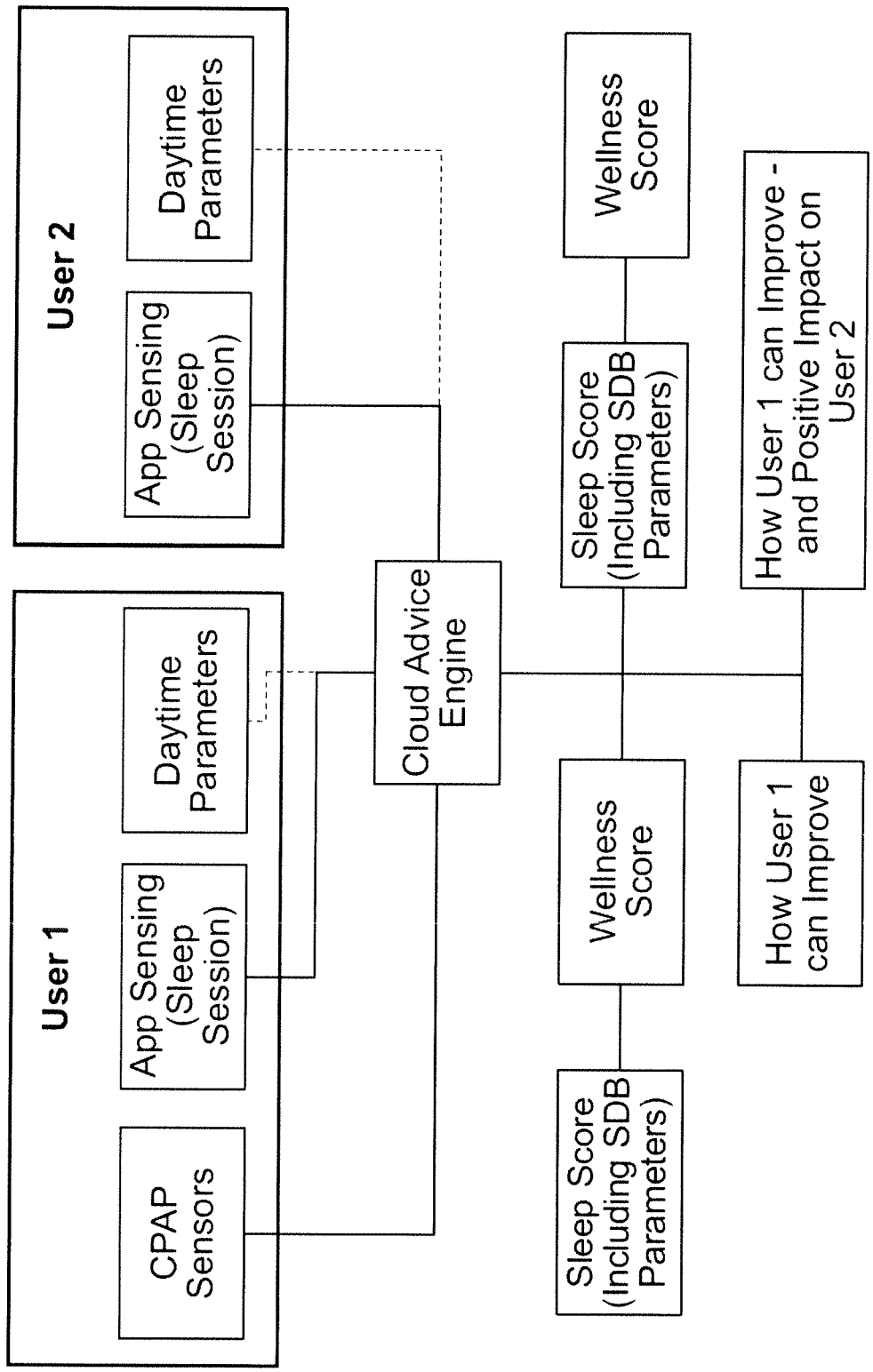
FIG. 18 is a processing schematic illustrating output of further processes for evaluation of motion characteristics derived, for example, by the audio sensing techniques described herein.

As illustrated in FIG. 18, the system can automatically capture a full sleep session of a person, the time of going to bed, time to sleep, actual sleep time, awakenings, and final wakening are captured. A sleep fragmentation, sleep efficiency, and Sleep Score can be estimated for the person. The quality of sleep of a person can be summarized in a single number, referred to as a Sleep Score. Typical Sleep Score input parameters for a healthy person include total sleep time, deep sleep time, REM sleep time, light sleep time, wake after sleep onset (WASO) time, and sleep onset (time to fall asleep). The Sleep Score can optionally use a person's demographics such as age and gender to provide a normalized score versus their population norm (normative value), as well as their respiration rate variability, and snoring levels.

Fatigue and Alertness Management

Information from one or more nights of sleep can be used to estimate the likely subjective and objective fatigue condition of the user, and feedback advice to the user to improve their alertness during the day or the quality of their sleep.

Bed Entry and Exit Detection

Ranging information and motion signatures can be used to detect bed entry and to detect bed exit—which is useful in home environments, as well in nursing homes and the like (e.g., to track dementia patients, predict likelihood of bed sores etc.).

Daytime (Awake) Monitoring

The low frequency ultrasonic technology can be used to estimate a respiratory trace for a person, and track daytime as well as nighttime breathing disorders. For example, persons with infections (including respiratory infections) may exhibit an elevated (versus their personal baseline) breathing rate, shallower breathing than usual, and an altered inspiratory to expiratory ratio.

Thus, it can be seen the system can be used to monitor and manage chronic patient health state where respiratory signals are a biomarker of the patients health state (such as in COPD, Asthma, CHF, Hypertension)—including by allowing the monitoring of longitudinal patterns, including risk stratification and early prediction of acute events where applicable. Other conditions such as chronic insomnia can be tracked by the processing device. An example of processing of measured physiological parameters in order to monitor chronic disease can be found in International patent application PCT/AU2015/050273 (WO 2015/179911), filed May 25, 2015 and entitled "Methods and Apparatus for Monitoring Chronic Disease", the entire disclosure of which is incorporated herein by reference.

As further illustrated in FIG. 18, the system can also use daytime parameters such as step counts and/or exercise intensity readings from devices such as wearables, or a step counter incorporated into a smartphone. For example, as part of a motivational feedback system, compliance with apnea therapy can be correlated with increased activity in the following days, as the user feels (and is) less fatigued. Subjective questions can also be asked during the day by the system to elucidate the relative feeling of alertness of sleepiness, and objective tests such as reaction tests (e.g., psychomotor vigilance tasks implemented on a smartphone) can be used to demonstrate the improvement due to PAP therapy. Data about food intake can also be correlated with therapy, showing a reduction in consumption of sugary/fatty foods when the person feels rested and refreshed. It is also possible to relate to daytime heart rate and/or non-invasive blood pressure estimates/measures (such as from a wearable device with an optical sensor). If such improvements are not seen, the system can explore further whether the therapy settings are appropriate for the user, or could benefit from adjustment. These parameters can be used to formulate a wellness score, related to their previous night(s) sleep score and CPAP score. Thus, the processing device, in conjunction with other devices such as with an internet server-based engine (e.g., cloud advice engine) can provide assessment with data of multiple devices.

Sleep Conditions Monitoring

The growth in chronic disease, and prevalence of SDB, is such that low-cost screening for respiratory disorders and/or changes in respiratory parameters over time is highly desirable.

When the person is asleep, undiagnosed or diagnosed sleep disorders such as sleep disordered breathing (SDB) can be detected and monitored. Three types of sleep-disordered breathing are (i) Obstructive Sleep Apnea (OSA—partial or full upper airway collapse during sleep), (ii) Central Sleep Apnea (CSA—a central nervous system disorder where the brain does not trigger a breathing signal, or this is not transmitted correctly) and (iii) mixed or complex sleep apnea (a combination of OSA and CSA).

Detecting of an apnea (cessation of breathing) or partial cessation (hypopnea) may be based on tracking the amplitude of the breathing signal over time. The relative amplitude of a time domain breathing signal of a person will tend to change with their position, and orientation of chest with respect to the smart speaker(s). For example, a breathing waveform of a person facing the processing device 100 will tend to be higher (larger in amplitude) than a breathing waveform when the person has their back to the sensor. Therefore, a local envelope of the signal is calculated as a reference point, so that cessation or diminution of apneas or hypopneas can be detected versus this local envelope.

In the frequency domain, apneas or hypopneas will tend to cause instability in the breathings rate calculation (e.g., the breathing rate keeps changing due to the apneas), and introduces some low frequency components. This makes FFT approaches to processing the respiratory signal less attractive when there is suspected SDB or other irregular breathing patterns. In this case better performance is possible if using wavelet decomposition methods. A mother wavelet function is defined as a function with a zero mean and localized in both frequency and time; through dilation and translation of a mother wavelet, a family of wavelets is produced. Where CWT (Continuous Wavelet Transform) and FFT estimates a similar breathing rate, there is a high likelihood that the breathing is "normal". The two estimates tend to be different when there are apneas or periodic breathing such as Cheyne Stokes.

By detecting and counting apnea and hypopnea events, it is possible to estimate an AHI (Apnea Hypopnea Index). This can be used to stratify SDB risk, and monitor apnea severity across nights. This can be done in either a stand-alone device, or in one integrated with a CPAP therapy device to indicate AHI when the user forgets to use their CPAP. In this way, behaviour change (e.g., to increase CPAP compliance) is encouraged via a Healthcare Informatics (HI) platform, as the user can see their Sleep Score worsen when they do not use their therapy. In terms of integrating with a CPAP, the low frequency ultrasonic sensing can be enable by a speaker and an externally directed microphone on the CPAP itself, or via a separate smart speaker or smart device (such as a smartphone or a tablet running an App). An example of a Sleep Score including apnea information is the ResMed's MyAir SleepScore.

Periodic limb movement disorder (PLM) occurs only during sleep and includes any repetitive, involuntary movement during the night that may lead to arousal, while restless legs syndrome (RLS) is an urge to move limbs that can also occur during wake (especially in the evening before sleep) as well as during sleep. These patterns can be detected in the signatures movements associated with these disorders, which are processed and identified by the machine learning block.

The outlined system provides convenient around-the-clock unobtrusive monitoring the health condition of a person, with the ability through AI to become part of clinical decision management process.

System for Monitoring Parameters for CPAP User and Family

AHI, Sleep Score, and Motivation (to Improve and Feedback on Therapy Compliance)

The non-contact sensing technology of the processing device 100 can measure absence/presence, sleep states (sleep or awake), sleep stages (i.e. light sleep, deep sleep, REM sleep), sleep quality, wake after sleep onset (WASO), total sleep time (TST), AHI, number of obstructive, hypopnea, mixed, and central apnea events, overlap syndrome, PLMD, RLS and other sleep parameters. Depending on configuration settings, it can also measure parameters such as heart rate, and heart rate variability.

A first use case is for subjects that have already been diagnosed with SDB, and have received a CPAP therapy device or a mandibular repositioning device (MRD). The system can measure both their sleep quality, and their disease progression. A key advantage is this measurement and feedback can be done whether they be on or off therapy (mask on or off; MRD in mouth or not). In a traditional approach, if a user with a positive air pressure device (CPAP or other respiratory/flow generator device) is not wearing their mask, their AHI is not recorded. In this new approach, their AHI can be detected and clearly shown, even when the user is not using therapy, acting as a key motivator for behavioral change in order to increase usage of the therapy.

The system monitors the sleep, breathing and SDB parameters of a user based on sensing located within the flow generator device itself. This may be limited to sensing in the time period around the expected sleep time, or running 24/7. It can provide an estimate of both treated and untreated AHI, as well as a comparison of both, in order to motivate the user to be compliant with the therapy. The system, such as the one illustrated in FIG. 5, can also use an app on a smartphone to enable the sensing, and optionally synchronize with the respiratory therapy device 5000 (e.g., CPAP device) to separate the treated and untreated parameters. Optionally, if no synchronization is available, the processing device 100 can carry out audio processing to detect the sound of the nearby therapy device (e.g., CPAP device) in order to categorize treated and untreated periods, and make an estimate of the type of flow generator and mask in use based on the audio signature. The system can clearly determine and show whether there is an increase in sleep score when the user is on therapy, as their snoring and a number of apneas dramatically decrease, allowing longer periods of REM and deep sleep. Even though the actual total sleep time may not increase, the quality of sleep may increases, along with a reduction in subjective and objective measures of fatigue. The system may then motivate the user (e.g., a middle-aged male) to continue using the therapy when positive results of the therapy are reported to the user by the processing device 100, such as by generating advice messages based on the determined events (e.g., AHI).

As shown in FIG. 1, a user may use the processing device 100 which may determine that the user is non-compliant with use of a therapy device (e.g., CPAP) for example, by detecting that the user is not using therapy—not wearing mask or not wearing MRD) but is running the monitoring application on a processing device (e.g., smart phone or smart speaker) which is sensing their sleep and SDB in order to check on their sleep quality and AHI. In the morning, they see that their sleep score is lower than when they are on therapy.

Figure 4:
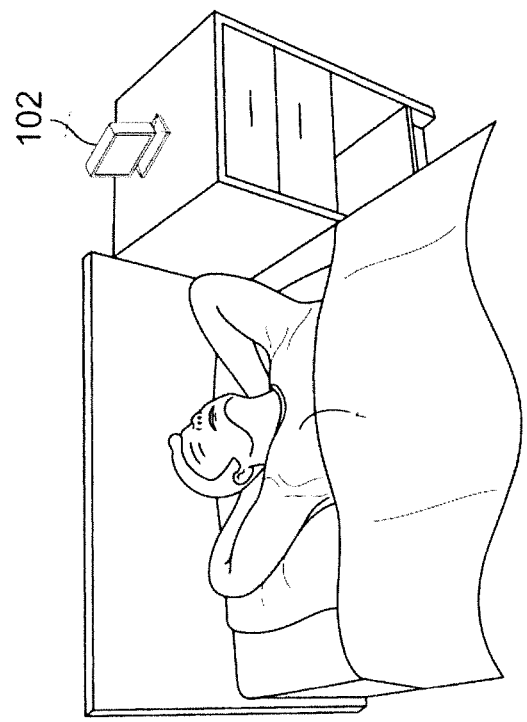
FIG. 4 illustrates example processing devices operating in a common area, which may be implemented with synchronization operations.
Figure 4:
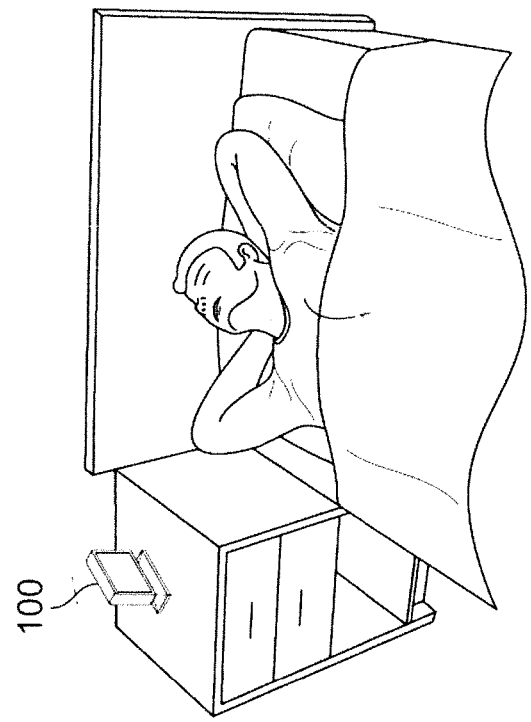

As shown in FIG. 4, multiple users may be monitoring by processing devices 100, 102 in a common sensing area. User #1 (on right hand side of diagram near processing device 102) is non-compliant with respiratory therapy (e.g., CPAP) because he is not using therapy—not wearing mask or not wearing MRD). The application is operating on the processing device (e.g., smart phone or smart speaker) which is sensing User #1's sleep and SDB in order to check on their sleep quality and AHI. User #2 (on left hand side—near processing device 100) is having a poor sleep as they are being disturbed by the apneic snoring of User #1, which is also being monitored by an application operating on processing device 100 (e.g., smart phone or smart speaker) near User #2. The next day, the applications of the devices may synchronize recording/determined information with a cloud service, and provide automated messaging advice to both people. User #1 may be encouraged to use their SDB therapy, whilst user #2 may be encouraged to urge User #1 to use their therapy.

Such as system may be understood further in relation to FIG. 18. User #1 and user #2 (partner) having been monitored with their processing devices may receive personalized Sleep Scores (including SDB parameters, snoring etc.), as well as a daytime wellness score (including fatigue/alertness levels, exercise etc.). Exemplar advice generated by the system for user #2 may be: "well done! You and your partner slept better last night, and feel better today!" with a reminder to encourage User 1 to remind User 1 to (continue to) use their therapy device (e.g., PAP) again (tonight) to keep up the improvement.

A second use case is where the same flow generator device (e.g., respiratory therapy device 5000) acts as a processing device 100 to also measure the sleep characteristics of the bed partner of the "main" therapy device user receiving the therapy (e.g., CPAP). In this case, the measurement of the bed partner (person not receiving the therapy) can be via range discrimination performed by the sensing system of the flow generator (e.g., FMCW RADAR or FMCW SONAR, AFHRG SONAR) which can allow for both persons to be monitored simultaneously.

Alternatively, as illustrated in FIG. 5, a SONAR application running on one or more separate smart devices (such as a smartphone, smart speaker, sound bar etc.) can operate to measure both users simultaneously (e.g., a single sound bar with multiple speakers/mics and beam forming, or two smart phones with coexisting sensing signals—located for example with one on each side of the bed). The purpose of monitoring the second person is to measure their sleep, and relate their sleep parameters with their partner's use of therapy (e.g., CPAP)—with the goal of showing that their sleep is also affected by their partner's condition and also improves when their partner is compliant with the therapy. This "family" use case can be enabled with no cost of goods sold (COGS) impact (i.e., no hardware sale needed) if the sensing is performed on a smart device that the user has already purchased. It can be seen that this system can also allow sensing by a CPAP device and sensing by a smartphone/smartspeaker application. These may coexist seamlessly in the same room, and each may automatically identify the type of device and sensing configuration (e.g., timing and frequencies) to operate so that both can coexist from a sensing perspective (avoid interference). This simultaneous sensing can also automatically relate the data, in order that personalized advice feedback be delivered by the system to each person. The overall goal is that the sleep score of the two users improves. It also provides an objective motivation factor for the therapy user (e.g., CPAP) to extend their therapy usage (improve compliance) as they can see the health benefits for themselves, as well as for their partner.

It can be seen that by detecting and recognizing the audible (and inaudible) signature of a CPAP device and/or mask, it may be possible to identify the hardware in use. This could be for a passive device (e.g., a legacy device, or from a different manufacturer), where the acoustic signature is extracted, and compared to a database of signatures for a closest match (e.g., carried out by software operating on a smartphone or smart speaker). This could also be for an active device (e.g., a device with active sensing that optionally transmits an inaudible acoustic sequence that identifies the device, mask, and other parameters such as serial number. This can also be used to check how long the mask has been in use, whether it is due for replacement, and check if the user is eligible for a replacement by their provider, and communicate with the provider and user.

From a technical standpoint, data are combined from the one or more processing devices 100, 102 (with their applications) (main user, partner, or main user and partner) and the therapy device (e.g., PAP), and optimization may be carried out. For example, the PAP device may return parameters such as usage hours, mask seal quality (related to leak), AHI events detected per hour, mask on/off events, pressure, flow rate, event flags, and a cumulative score. The processing device 100 can measure not only respiration parameters, snoring, but also other types of movements such as of rolling, RLS, PLM, in order to determine sleep stages, and AHI value. The processing device 100 can provide a second source of information to confirm the AHI where the mask leak is high (based on the acoustic sound of the leak) in addition to the machine data for example—and also if the user takes off the mask during the night. It can also act as second source of information by detecting obstructive and central events, based in changes in respiration envelope as detected using low frequency ultrasonic sensing.

Where the sound of snoring is detected by one or both processing devices in a two person monitoring situation, the PAP data can be used to isolate the snoring to the PAP user or to the partner. The data can be exchanged via short range communication such as NFC, Bluetooth, Wi-Fi etc., or via a cloud based service that aggregates the data sources. One use case is where the processing devices transmit data to an internet-based cloud service using a Wi-Fi or cellular (e.g., 3G, 4G/LTE) service, and the therapy device via a cellular MODEM. Another use case is where the CPAP shares data via Bluetooth to one of the phones, and a single application on the processing device (e.g., phone) processes the CPAP parameters, as well as provides the low frequency ultrasonic sensing and processing. A single processing device can be seen to provide seamless physiological monitoring of the user, even when off therapy.

If the external acoustic sensing is incorporated into the therapy device (e.g., PAP), the PAP motor and humidifier acoustic signature should be considered, as well as leaks. Thus, the PAP-based processing device 100 can select a sensing waveform for sensing operations that will be robust to the sound of the device when in use. Leak can be classified as expected (i.e., during normal operation) or unexpected (e.g., where the mask is too loose or too tight).

One practical application of room presence detection is an automatic humidifier warm-up feature. Thus, when a processing device detects presence of a user such as in a typical bed time window, the processing device may activate the therapy device such as to warm up its components (e.g., humidifier, conduits, etc.) This allows the PAP to be ready for immediate use. Thus, by detecting when the user comes into the room using presence sensing, which may be related to a known sleep time such as recently recorded bed-times and data from other sensors (such as light sensors), activation of the therapy device may be appropriately made.

By detecting the sleep pattern from the acoustic sensing using a processing device, the start-up pressure ramp time of the therapy device (e.g., flow generator or PAP) may be adjusted by the system based not on predetermined time limits, but on the user's own sleep parameters as communicated from an external processing device 100 or the processing device as integrated with the therapy device. Thus, the therapy pressure or pressure support provided to the user may be increased once the user has actually fallen asleep as detected by the processing device, and moved from light sleep to either deep or any REM stages.

Multiple user compliance monitoring (such as in the same bed room) may be considered by the following example. Such compliance monitoring may concern either when a CPAP user forgets to use their device, and a device reports an increase in their AHI and is detected that they were not using therapy. Simultaneously, the system, such as with an additional device may monitor their partner and detect that the partner's monitored sleep degrades (for example, because the CPAP user in the bedroom was snoring heavily and not using the CPAP device). The device/system can notify the user of their partner's worsened sleep, and also be provided advice to nudge the other user to use their PAP, MRD etc. Alternatively, or additionally, the device/system can notify the partner with advice/feedback on their worsened sleep and also be provided advice to nudge the other user to use their PAP, MRD, etc. In this scenario of two people, both can have the low frequency ultrasonic sensing with one or more processing devices, and the system may inter-relate their sleep score, sleep stats, snoring parameters, respiratory parameters etc., any of which may be correlated with the compliance and/or non-compliance.

The system detects which of the people in the common vicinity (e.g., the partner or the CPAP user) is snoring. Thus, the system may detect that a first user on PAP is compliant, but they are being disturbed by their partner snoring (or maybe even with undiagnosed SDB). The partner and/or first user in this case may receive advice of a suggestion for sleep apnea diagnosis for the snoring person, so that both may be urged to use therapy.

Checking the Efficacy of a Mandibular Device to Provide Personalized Care.

A mandibular repositioning device (MRD) can be used to treat obstructive sleep apnea and snoring, by pushing the tongue and jaw forward in order to improve airflow. Since the processing device 100 of the system may monitor the SDB parameters, such as AHI, of a user without MRD, and with MRD, the processing device may provide date to verify the efficiency of the therapy. If the user is complaint with the MRD, but their SDB parameters are not improving, they may be referred for adjustment of the device, or CPAP titration.

User is not Compliant with Therapy but Backend System does not Know why.

The processing device 100 of the system can monitor a room environment, and recognize a specific user that has been provided with therapy (such as a CPAP device). If they are present, but not using the therapy device during their sleep, they might be considered to be not "compliant", and appropriate help and advice may be given to check why this is and to motivate the user to resume therapy (e.g., new settings may be provided to the therapy device to improve comfort, a new mask etc.). If they are absent, this may be understood to suggest that they are away.

A Person with a CPAP has their Breathing Collected During Therapy by the Machine, but not Heart Rate The above described ultrasonic processing devices 100, 102 of the system, such as the integrated processing device/therapy device, can measure heart rate during therapy and when therapy is off, when the user is near either their PAP or their smart device. This can be used to detect changes in heart rate pattern (such as bradycardia/tachycardia patterns indicative of apnea) when on and off therapy so as to correlate cardiac variability with respect to a present and absent (i.e., used and unused) respiratory therapy. Thus, it can also be used to show an improvement in heart rate parameters as a result of therapy, such as increased heart rate variability (HRV and reduced baseline rate (within normal healthy ranges). Changes in HRV are believed to be related to differences in the degree of parasympathetic and sympathetic stimulation of the heart, and related to cardiovascular morbidity and mortality.

Screening for SDB

SDB Screening Using an App(lication)

Screening for SDB typically requires specific hardware to do so, which is "barrier to entry" for screening of potentially apneic subjects. The use of the above described technology helps to overcomes such an issue. Disorders such as restless leg syndrome (RLS) and periodic limb movement disorder (PLMD) can also be screened. The screening may also indicate other related conditions—from the users with PLMD, approximately 44% will have attention-deficit hyperactivity disorder (ADHD).

It is possible to use respiratory sensing in a processing device 100 to provide an SDB screening service. The user simplify downloads an application for the processing device, and uses it to monitor their sleep for one or more nights. This can monitor a range a of parameters, such as breathing morphology (shape) to identify breathing cessations for a period of time (apnea), as well as reductions in amplitude from neighboring breaths (hypopnea). Where PLM or RLS is detected, the advice system can check other parameters included diet (iron deficiency), exercise, stress levels, sleep deprivation (based on overnight data), use of anti-depressants (e.g., SSRIs). These can be monitored by way or receiving subjective feedback from the use by way of data entry capabilities of the PAP device or the smart device.

Screening for SDB in Hospital in Preoperative Scenarios

Preoperatively, a patient can be screened for SDB overnight, and the resulting AHI values can be providing to the physicians/anesthetists in order to optimize care such as for the operation.

Monitoring and Managing Chronic Disease

As an example, a person with a chronic disease (such as COPD or CHF) begins to get sicker at home.

The processing device 100 of the system can use respiratory parameter sensing (and optionally coughing) to check how they are feeling, ask questions and receive feedback using a voice assistant. The data is then processed and an indication of the current state of the user, or of a potential exacerbation of a chronic condition, is obtained. The system may recommend discussion with a doctor, or can automatically notify a doctor or link the user to a doctor.

Improve Sleep

With a soothing masking noise (e.g., white noise), the processing device 100 of the system can implemented to help an adult or baby to sleep, such as in a neonatal incubator and/or neonatal intensive care unit, nursery or hospital setting, as well as for the monitoring of their breathing. The masking noise itself could be an acoustic sensing signal, if UWB is utilized as previously described. The efficiency of such a mitigating action (playing a soothing masking noise or playing music) or that of other mitigating actions (changing the light or the temperature in the room, rocking the bed etc.), can be evaluated by quantifying the effect of each of these measures (in isolation or in combination) on the user's sleep score.

Device is Placed Near Baby's Cot

The processing device 100 of the system can detect breathing cessations indicative of SIDS by detecting apneas, and continued cessation of breath.

Independent Living

No Motion of an Elderly Person

If the processing device 100 of the system detects that a monitored person is present and breathing, but has not moved for a predetermined period of time, the processing device 100 of the system may be automated to ask the person a question. Alternatively, the processing device 100 of the system may be set to or update a remote monitoring center if the person not entered the sensing space for a predetermined time.

Safety for Elderly People

In one example, the described system is part of the Internet of Things (IoT). In this case the processing device 100 of the system is integrated with a building power and can interact with, and affect a change of lighting, the turning of light(s) on and off, the closing of window shutters etc. For example, if the user is detected as falling asleep, but an oven, stove or other heating appliance is left on, such an integrated system can automatically turn down the heat, turn off the appliance, or optionally wake the user with an alarm sound and/or voice with increasing volume.

The system may be used to detect potential safety/health issues. For example, if a person is detected in a horizontal position in a room other than bedroom, it may be used to assume that the person has fallen. This may trigger questions/answers session with the person and/or measuring further parameters such as breathing rate, heart rate etc. A combination of elevated breathing/heart rate and non-responsiveness, may trigger a warning, such as sending an SMS, email or other communication to a pre-determined recipient. This mode of operation may be implemented as a part of the general monitoring, or as a specialized mode for monitoring elderly people. A variation of this mode may include monitoring only the health parameters and sensing a warning when the parameters are outside a normal range or a predetermined range, even if the person is detected as siting in a chair and not lying on the floor (meaning—there has not been a fall).

Detecting Sleep Walking

Sleepwalking is more likely to occur during deep slow wave sleep (SWS) early in the night, but can still occur during REM sleep near the morning. The sleep staging algorithm of the processing device 100 of the system that detects the user's sleep stages, can detect the wake-type movement as the person gets out of bed (or back in to bed) with paradoxical respiratory patterns that are consistent with REM or deep sleep (e.g., based on the standard deviation of normalized running median filtered breathing rate estimate and other features). Where the absence periods are greater than a sleep walking threshold (e.g., >5 mins), the processing device 100 of the system can flag an area of suspected sleep walking. The user can then be asked for subjective feedback in the morning to see if they remember getting out of bed. If not, a possible sleep walking event has been detected. As a sleep walker may turn on and off lights or open and close locks, such feedback from IoT sensors cannot be considered to be conclusive. However, lights, locks, and motion detections (including any video capture in the living space) can be used to detect the possible path of a person (particularly if the person lives alone) during a suspected sleep walking event. Incidence of sleep walking can be correlated with increases in stress (e.g., derived from changes in heart rate variability—such as reduction in this variability), increases in respiration rate, and changes in inspiration/expiration waveform timing from a normal baseline.

People with Untreated Depression

The processing device 100 of the system can keep track of cardiac parameters such as resting heart rate, and heart rate variability can be used as inputs into a depression classification system. A reduction in HRV spectral parameters, an indication of a decrease in parasympathetic and increase in sympathetic innervation, can be used and optionally combined with answers to questions asked from the user in order to risk stratify for depression.

System for Providing Advice to a User

The approach to delivering personalized advice can be via text in an application of the processing device 100 of the system, or via voice or video. For example, in the case of a voice assistant, a very interactive approach is possible—i.e., sleep advice is delivered in a conversational tone. The system delivers advice based on objective and subjective data, delivered as voice (or text), and user can respond via voice or text.

An example would be a processing device 100 of the system that notes that actual recorded deep sleep percentage has decreased for a user for the last night's sleep. The voice assistant can report this, check the user's daily monitoring device (a step counter with Bluetooth) and sees a drop in exercise duration and intensity, and ask the user if they can take more exercise today (to bring them closer to their ongoing trend). The user replies that they are very busy on a stressful project in work, and have no time for their usual lunchtime jog. The audio voice of the processing device 100 of the system reassures them it's perfectly OK, and offers to provide a relaxation program before bedtime. The user accepts, and the system sets an alarm to remind the user an hour before their anticipated bed time.

Another example would be where the sensing system detects the breathing waveform pattern (shape) throughout the night, detects the location of the person in the room, and also performs audio snoring analysis. The changes in respiration waveform morphology are cross referenced to snoring events, in order to classify the snoring as being from the sensed person at a location, or from a partner. This is an advantage over traditional snoring analysis that cannot distinguish snoring between users (when one or other—or indeed both—may be snoring). The system may be implemented to synchronize the local breathing signal with the audio sound signal of a snore, and hence determine/confirm if the monitored person is the one that is snoring (i.e., distinguish between who is making the sound and who is not as we the system has access to both sound and movement signals). For example, a person cannot breathe and snore at a different cadence (on/off period of the snore, inspiration/expiration time) or rate. There are other characteristics of both signals such as amplitude, and/or envelope that can be processed.

In addition, by utilizing the distance metric, and sensitivity characteristics of the microphone(s) of the device, it is possible for the system to check the snoring amplitude against distance to calibrate snore parameters, such as to produce a snore score. This snore score can include number of snores, duration, intensity, and impact on sleep stages. Depending on the severity of snoring, the system can use voice feedback to ask the user about alcohol intake, their subjective tiredness (to rate their feeling of tiredness), discuss their body position during the night and type of pillow, ask the user (and/or interrogate other sensors such as body temperature, resting respiration rate trends, SDB parameters, acoustic cough detection) if they have a cold/flu symptoms. Depending on the spectrum of input data and user responses, the system can determine whether one or more product recommendation(s) relating to medical treatment or medicine such as whether decongestants or nasal sprays would be appropriate, and provide relevant information to the user or relevant reference to a medical practitioner.

5.2 Other Remarks

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the present technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilized to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

The invention claimed is:

1. A non-transitory processor-readable medium, having stored thereon processor-executable instructions which, when executed by a processor, cause the processor to detect physiological movement of a user by controlling a mechanical production of a sound signal by a speaker and processing a transduced reflection of the sound signal obtained with a microphone, the processor-executable instructions comprising:
    instructions to electronically control mechanically producing, via a speaker coupled to an electronic processing device, the sound signal in a vicinity of the electronic processing device, wherein the electronic control comprises generating concurrent modulating frequency signals to the speaker with a first ramp of frequencies comprising a speaker frequency upsweep, and a second ramp of frequencies comprising another speaker frequency upsweep, whereby a change in frequency of the concurrent modulating frequency signals from an end of a ramp to a next ramp avoids an audible click from the speaker;
    instructions to electronically control sensing, via a microphone coupled to the electronic processing device, a reflected sound signal from the vicinity of the electronic processing device, wherein the sensed reflected sound signal is the transduced reflection of the sound signal produced by the speaker; and
    instructions to electronically generate, by the processor, an electronic data signal representative of physiological movement comprising the detected physiological movement, from at least a portion of the sensed reflected sound signal and a signal representative of at least a portion of the sound signal,
    wherein the sound signal comprises a dual tone frequency modulated continuous wave signal that is created from the speaker with dual overlapped tones.

2. The non-transitory processor-readable medium of claim 1 wherein:
    (a) at least a portion of the produced sound signal is in an inaudible sound range; or
    (b) at least a portion of the produced sound signal is in an inaudible sound range, wherein the portion of the produced sound signal is a low frequency ultrasonic acoustic signal.

3. The non-transitory processor-readable medium of claim 1 wherein the processor-executable instructions to generate the electronic data signal comprise instructions for demodulation of the portion of the sensed reflected sound signal with the signal representative of the portion of the sound signal.

4. The non-transitory processor-readable medium of claim 3 wherein the demodulation comprises a multiplication of the signal representative of at least the portion of sound signal and the portion of the sensed reflected sound signal.

5. The non-transitory processor-readable medium of claim 1 wherein demodulation to derive generate the electronic data signal comprises a multiplication of a received signal with itself, the received signal including the portion of the sensed reflected sound signal and direct path sound from at least the portion of the sound signal.

6. The non-transitory processor-readable medium of claim 1, further comprising:
(a) wherein the generated electronic data signal further comprises detection of one or more of respiration, cardiac and gross movement; and/or
(b) processor-executable instructions to evaluate the generated electronic data signal representative of the physiological movement to determine one or more physiological parameters; and/or
(c) processor-executable instructions to generate an output based on an evaluation of the physiological movement represented by the generated electronic data signal.

7. The non-transitory processor-readable medium of claim 1, wherein the signal representative of at least the portion of the sound signal is an internally generated oscillator signal or a measured direct path sound signal.

8. The non-transitory processor-readable medium of claim 1, wherein the signal representative of at least the portion of the sound signal is an oscillator signal and the instructions to generate the electronic data signal representative of the physiological movement are configured to multiply the oscillator signal with at least the portion of the sensed reflected sound signal.

9. The non-transitory processor-readable medium of claim 1 further comprising any one or more of:
(a) processor-executable instructions to filter the portion of the sensed reflected sound signal with an adaptive filter configured to change a passband of the adaptive filter based on any one of a timing of at least a portion of the produced sound signal and a timing of the portion of the sensed reflected sound signal;
(b) processor-executable instructions to generate an ultra-wide band (UWB) sound signal as audible white noise, and wherein the processor-readable medium comprises instructions to detect user motion with the UWB sound signal.

10. The non-transitory processor-readable medium of claim 1 further comprising:
(a) processor-executable instructions to sum the sound signal and audible audio content to produce the sound signal and the audible audio content simultaneously via the speaker; or
(b) processor-executable instructions to sum the sound signal and audible audio content to produce the sound signal and the audible audio content simultaneously via the speaker, and further comprising processor-executable instructions to filter the audible audio content based on frequencies of the sound signal before summing the sound signal and audible audio content.

11. The non-transitory processor-readable medium of claim 1 further comprising:
(a) processor-executable instructions to control a variation of a detection scheme of the sound signal depending on detected presence of a subject in the vicinity, wherein the processor-executable instructions vary waveform parameters of at least a portion of the sound signal; and/or
(b) processor-executable instructions to generate a continuous wave sound signal for motion detection, and to initiate, upon detection of user motion in the vicinity, producing the dual tone frequency modulated continuous wave signal via the speaker.

12. The non-transitory processor-readable medium of claim 1, wherein the dual tone frequency modulated continuous wave signal comprises a first sawtooth frequency change overlapped with a second sawtooth frequency change in a repeated waveform.

13. The non-transitory processor-readable medium of claim 1 wherein the produced sound signal provides a cosine-like functional time domain shape including zero crossings.

14. The non-transitory processor-readable medium of claim 1, further comprising processor-executable instructions to generate an output based on an evaluation of the physiological movement of the generated electronic data signal, and wherein the output comprises:
(a) output data representing any one or more of:
a human presence state;
presence or absence of motion in the physiological movement signal;
a sleep state;
sleep walking;
a breathing characteristic;
a cardiac characteristic;
a gross movement characteristic;
a sleep characteristic;
an event of sleep disordered breathing;
an event of periodic breathing;
a respiratory condition;
a fatigue condition;
a wellness score;
a chronic disease condition;
a sleepiness condition; and
a fatigue condition;
or
(b) initiating an event based on any of the output data.

15. The non-transitory processor-readable medium of claim 14 wherein the initiated event includes turning a device, or a process associated with the device, on or off; and/or introducing an adjustment to an operation of a device, or a process associated with the device.

16. The non-transitory processor-readable medium of claim 15 wherein the device is a respiratory therapy device, and the process is associated with the respiratory therapy device.

17. The non-transitory processor-readable medium of claim 1 further comprising any one or more of:
(a) processor-executable instructions to bin search in fast Fourier transform windows derived with the generated electronic data signal to select a range associated with user motion;
(b) processor-executable instructions to detect and recognize an audible sound of a respiratory pressure therapy device sensed by the microphone;
(c) processor-executable instructions to detect a cardiac variability and correlate the cardiac variability with respect to a present and absent respiratory therapy; and
(d) processor-executable instructions to play an audible query through the speaker in response to an analysis of the physiological movement signal.

18. The non-transitory processor-readable medium of claim 1 further comprising processor-executable instructions to chirp filter sound sensed by the microphone to isolate the portion of the sensed reflected sound signal.

19. The non-transitory processor-readable medium of claim 18 wherein, to chirp filter, the processor digitally filters with a pass band in a frequency range of the produced sound signal.

20. The non-transitory processor-readable medium of claim 1 further comprising processor-executable instructions to selectively change modulation parameters of production of at least a portion of the sound signal to sense motion in the vicinity of the electronic processing device with different sound signal modulation characteristics.

21. The non-transitory processor-readable medium of claim 20 wherein the different sound signal modulation characteristics comprise any two or more of continuous wave (CW), frequency modulated continuous wave (FMCW), ultra-wide band (UWB), frequency-shift keying (FSK) and phase-shift keying (PSK).

22. The non-transitory processor-readable medium of claim 1, wherein the electronic processing device comprises a smart phone or a smart watch.

23. The non-transitory processor-readable medium of claim 1, further comprising:
(a) processor-executable instructions related to synchronization including a cross-correlation of a sensed reflected signal with a sensed direct path signal; and/or
(b) processor-executable instructions for a synchronization process comprising multiplying a reference template with at least a portion of the sensed reflected sound signal.

24. A server with access to the non-transitory processor-readable medium of claim 1, wherein the server is configured to receive requests for downloading the processor-executable instructions of the non-transitory processor-readable medium to the electronic processing device over a network.

25. An electronic processing device comprising: one or more processors; a speaker coupled to the one or more processors; a microphone coupled to the one or more processors; and the non-transitory processor-readable medium of claim 1.

26. The electronic processing device of claim 25 wherein the electronic processing device is one of a mobile phone or a smart speaker.

27. The electronic processing device of claim 25 wherein the electronic processing device is a respiratory pressure therapy device.

28. A method of a server having access to the non-transitory processor-readable medium of claim 1, the method comprising receiving, at the server, a request for downloading the processor-executable instructions of the non-transitory processor-readable medium to an electronic processing device over a network; and transmitting the processor-executable instructions to the electronic processing device in response to the request.

29. A method of a processor for detecting physiological movement using an electronic processing device, comprising:
electronically controlling producing, via a speaker coupled to the electronic processing device, a sound signal in a vicinity of the electronic processing device wherein the electronic controlling via the speaker comprises generating concurrent modulating frequency signals to the speaker with a first ramp of frequencies comprising a speaker frequency upsweep, and a second ramp of frequencies comprising another speaker frequency upsweep, whereby a change in frequency of the concurrent modulating frequency signals from an end of a ramp to a next ramp avoids an audible click from the speaker;
electronically controlling sensing, via a microphone coupled to the electronic processing device, a reflected sound signal from the vicinity of the electronic processing device; and
electronically controlling, in the processor, generating of an electronic data signal representative of the physiological movement comprising the detected physiological movement, with at least a portion of the sensed reflected sound signal and a signal representative of at least a portion of the sound signal,
wherein the sound signal comprises a dual tone frequency modulated continuous wave signal that is created from the speaker with dual overlapped tones.

30. The method of claim 29 wherein:
(a) at least a portion of the produced sound signal is in an inaudible sound range; or
(b) at least a portion of the produced sound signal is in an inaudible sound range and wherein the portion of the produced sound signal is a low frequency ultrasonic acoustic signal.

31. The method of claim 29 wherein the generating of the electronic data signal representative of the physiological movement comprises demodulation of the portion of the sensed reflected sound signal with the signal representative of the portion of the sound signal.

32. The method of claim 31 wherein the demodulation comprises a multiplication of the signal representative of at least the portion of the sound signal and the portion of the sensed reflected sound signal.

33. The method of claim 29 wherein the demodulation comprises a multiplication of a received signal with itself, the received signal including the portion of the sensed reflected sound signal and direct path sound from at least a portion of the sound signal.

34. The method of claim 29 further comprising:
(a) wherein the generating of the electronic data signal further comprises detecting one or more of respiration, cardiac and gross movement; and/or
(b) evaluating the generated electronic data signal to determine one or more physiological parameters; and/or
(c) generating an output based on an evaluation of the generated electronic data signal.

35. The method of claim 29 wherein the signal representative of the portion of the sound signal is an internally generated oscillator signal or a direct path measured sound signal.

36. The method of claim 29 wherein generating the electronic data signal representative of the physiological movement comprises multiplying an oscillator signal with the portion of the sensed reflected sound signal.

37. The method of claim 29 further comprising any one of more of:
(a) filtering the portion of the sensed reflected sound signal with an adaptive filter configured to change a passband of the adaptive filter based on any one of a timing of at least a portion of the produced sound signal and a timing of the portion of the sensed reflected sound signal; and
(b) generating an ultra-wide band (UWB) sound signal as audible white noise, and detecting user motion with the UWB sound signal.

38. The method of claim 29 further comprising:
(a) combining the sound signal and audible audio content to produce the sound signal and the audible audio content simultaneously via the speaker; or
(b) combining the sound signal and audible audio content to produce the sound signal and the audible audio content simultaneously via the speaker, and filtering the audible audio content based on frequencies of the sound signal before summing the sound signal and the audible audio content.

39. The method of claim 29 further comprising:
(a) controlling a variation of a detection scheme of the sound signal depending on detected presence of a subject in the vicinity, wherein the variation comprises changing waveform parameters of at least a portion of the sound signal; and/or
(b) generating a continuous wave sound signal for motion detection, and upon detection of user motion in the vicinity with the continuous wave sound signal, initiating producing the dual tone frequency modulated continuous wave signal via the speaker.

40. The method of claim 29 wherein the dual tone frequency modulated continuous wave signal comprises a first sawtooth frequency change overlapped with a second sawtooth frequency change in a repeated waveform.

41. The method of claim 29 wherein the produced sound signal provides a cosine-like functional time domain shape including zero crossings.

42. The method of claim 29 further comprising generating an output based on an evaluation of the generated electronic data signal, wherein the generated output comprises:
(a) output data comprising any one or more of:
a human presence state;
presence or absence of motion in the physiological movement signal;
a sleep state;
a breathing characteristic;
sleep walking;
a cardiac characteristic;
a gross movement characteristic;
a sleep characteristic;
an event of sleep disordered breathing;
an event of periodic breathing;
a respiratory condition;
a fatigue condition;
a wellness score;
a chronic disease condition;
a sleepiness condition; and
a fatigue condition;
or
(b) initiating an event based on any of the output data.

43. The method of claim 42 wherein: (a) the initiated event includes turning a device, or a process associated with the device, on or off; and/or (b) introducing an adjustment to an operation of a device, or a process associated with the device.

44. The method of claim 43 wherein the device is a respiratory therapy device, and the process is associated with the respiratory therapy device.

45. The method of claim 29 further comprising any one or more of:
(a) bin searching in fast Fourier transform windows derived with the generated electronic data signal to select a range associated with user motion;
(b) in the processor, detecting and recognizing an audible sound of a respiratory pressure therapy device sensed by the microphone;
(c) detecting a cardiac variability and correlating the cardiac variability with respect to a present and absent respiratory therapy; and
(d) playing an audible query through the speaker in response to an analysis of the physiological movement signal.

46. The method of claim 29 further comprising chirp filtering sound sensed by the microphone to isolate the portion of the sensed reflected sound signal.

47. The method of claim 46 wherein the chirp filtering digitally filters with a pass band in a frequency range of the produced sound signal.

48. The method of claim 29 further selectively changing modulation parameters of production of at least a portion of the sound signal to sense motion in the vicinity of the electronic processing device with different sound signal modulation characteristics.

49. The method of claim 48 wherein the different sound signal modulation characteristics comprise any two or more of continuous wave (CW), frequency modulated continuous wave (FMCW), ultra-wide band (UWB), frequency-shift keying (FSK) and phase-shift keying (PSK).

50. The method of claim 29 wherein the electronic processing device comprises a smart phone or a smart watch.

51. The method of claim 29 further comprising:
(a) in a synchronization process, multiplying a reference template with at least a portion of the sensed reflected sound signal; and/or
(b) in a synchronization process, cross-correlating the sensed reflected sound signal with a sensed direct path signal.

* * * * *